US009973484B2

(12) United States Patent
Reid et al.

(10) Patent No.: US 9,973,484 B2
(45) Date of Patent: *May 15, 2018

(54) SYSTEM AND METHOD FOR SECURELY STORING AND SHARING INFORMATION

(71) Applicant: REID CONSULTING GROUP LLC, Athens, OH (US)

(72) Inventors: Thomas Alan Reid, Athens, OH (US); Dennie Guy, Crawford, CO (US)

(73) Assignee: Reid Consulting Group, Inc., Athens, OH (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/170,981

(22) Filed: Jun. 2, 2016

(65) Prior Publication Data

US 2016/0277374 A1    Sep. 22, 2016

Related U.S. Application Data

(63) Continuation-in-part of application No. 14/539,614, filed on Nov. 12, 2014, now Pat. No. 9,390,228.
(Continued)

(51) Int. Cl.
*H04L 29/06* (2006.01)
*G06F 19/00* (2018.01)
(Continued)

(52) U.S. Cl.
CPC .......... *H04L 63/061* (2013.01); *G06F 19/322* (2013.01); *G06F 21/602* (2013.01);
(Continued)

(58) Field of Classification Search
CPC ..... G06Q 50/00; G06F 19/322; G06F 19/324; G06F 19/327; G06F 21/6218;
(Continued)

(56) References Cited

U.S. PATENT DOCUMENTS 8,566,578 B1   10/2013  Banerjee
9,246,676 B2   1/2016   Leavy et al.
(Continued)

FOREIGN PATENT DOCUMENTS

CN          102014133 A     4/2011

OTHER PUBLICATIONS

International Search Report and Written Opinion dated Feb. 2, 2016; International Application No. PCT/US2015/059717; International File Date Nov. 9, 2015.
(Continued)

*Primary Examiner* — John B King
*Assistant Examiner* — Arya Golriz
(74) *Attorney, Agent, or Firm* — Tarolli, Sundheim, Covell & Tummino LLP

(57) ABSTRACT

The present application generally relates to systems, devices, and methods to conduct the secure exchange of encrypted data using a three-element-core mechanism consisting of the key masters, the registries and the cloud lockboxes with application programming interfaces providing interaction with a wide variety of user-facing software applications. Together the mechanism provides full lifecycle encryption enabling cross-platform sharing of encrypted data within and between organizations, individuals, applications and devices. Control of the private key required for decryption is maintained by the information owner. More specifically, the mechanism establishes unique identities, verifies authenticity, generates and securely exchanges asymmetric encryption key pairs, encrypts, transmits, receives and decrypts data to/from cloud lockboxes; creates and appends metadata specific to the applications and retrieves and/or act upon metadata.

59 Claims, 26 Drawing Sheets

Related U.S. Application Data which is a continuation-in-part of application No. 13/665,861, filed on Oct. 31, 2012, now Pat. No. 9,378,380.

(60) Provisional application No. 61/553,883, filed on Oct. 31, 2011.

(51) Int. Cl.
 G06F 21/60 (2013.01)
 G06F 21/62 (2013.01)

(52) U.S. Cl.
 CPC ........ G06F 21/6209 (2013.01); H04L 63/045 (2013.01); H04L 63/0428 (2013.01); H04L 63/0435 (2013.01); H04L 63/101 (2013.01)

(58) Field of Classification Search
 CPC ............... G06F 21/60; G06F 17/30233; H04L 63/0815; H04L 63/0435
 See application file for complete search history.

(56) References Cited

U.S. PATENT DOCUMENTS

| | | |
|---|---|---|
| 9,270,663 B2 | 2/2016 | Kravits et al. |
| 2004/0078593 A1 | 4/2004 | Hind et al. |
| 2007/0192836 A1 | 8/2007 | Shiran et al. |
| 2008/0104705 A1 | 5/2008 | Hasbun |
| 2009/0228950 A1 | 9/2009 | Reed et al. |
| 2010/0122120 A1 | 5/2010 | Lin |
| 2011/0055202 A1 | 3/2011 | Heimendinger |
| 2011/0066863 A1 | 3/2011 | Katzenbeisser et al. |
| 2012/0257759 A1 | 10/2012 | Nick et al. |
| 2013/0275470 A1 | 10/2013 | Cao et al. |
| 2013/0297662 A1* | 11/2013 | Sharma ............... H04L 63/0815 707/827 |
| 2014/0046708 A1 | 2/2014 | Werner |
| 2014/0068202 A1 | 3/2014 | Goddard |
| 2014/0082749 A1* | 3/2014 | Holland ................ G06F 21/645 726/29 |
| 2014/0129047 A1 | 5/2014 | Barrett |
| 2014/0245012 A1 | 8/2014 | Arya et al. |
| 2015/0074409 A1 | 3/2015 | Reid et al. |

OTHER PUBLICATIONS

International Search Report and Written Opinion dated Aug. 23, 2017; International Application No. PCT/US2017/035695; International File Date Jun. 2, 2017.

\* cited by examiner

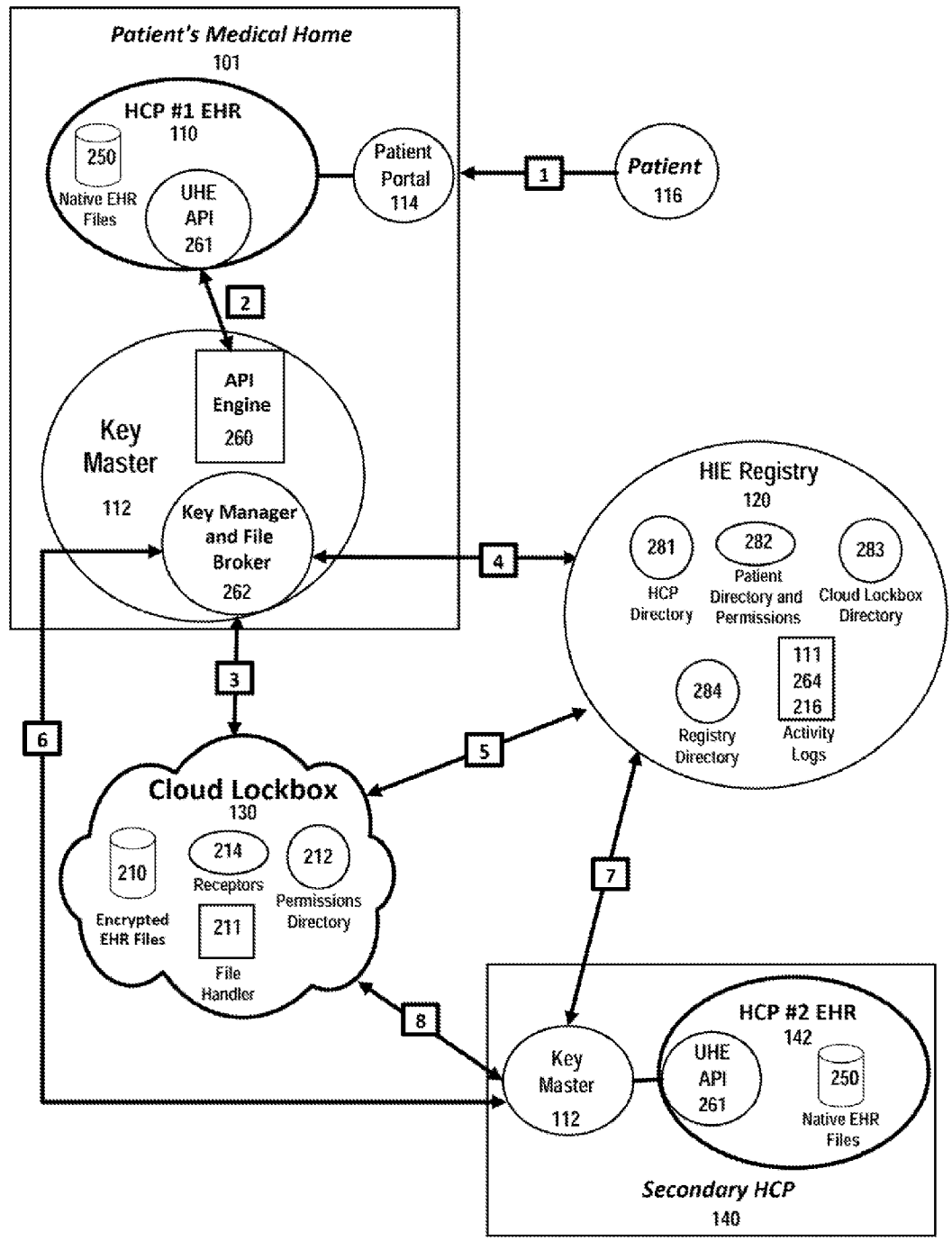
Figure 2: UHE in Action

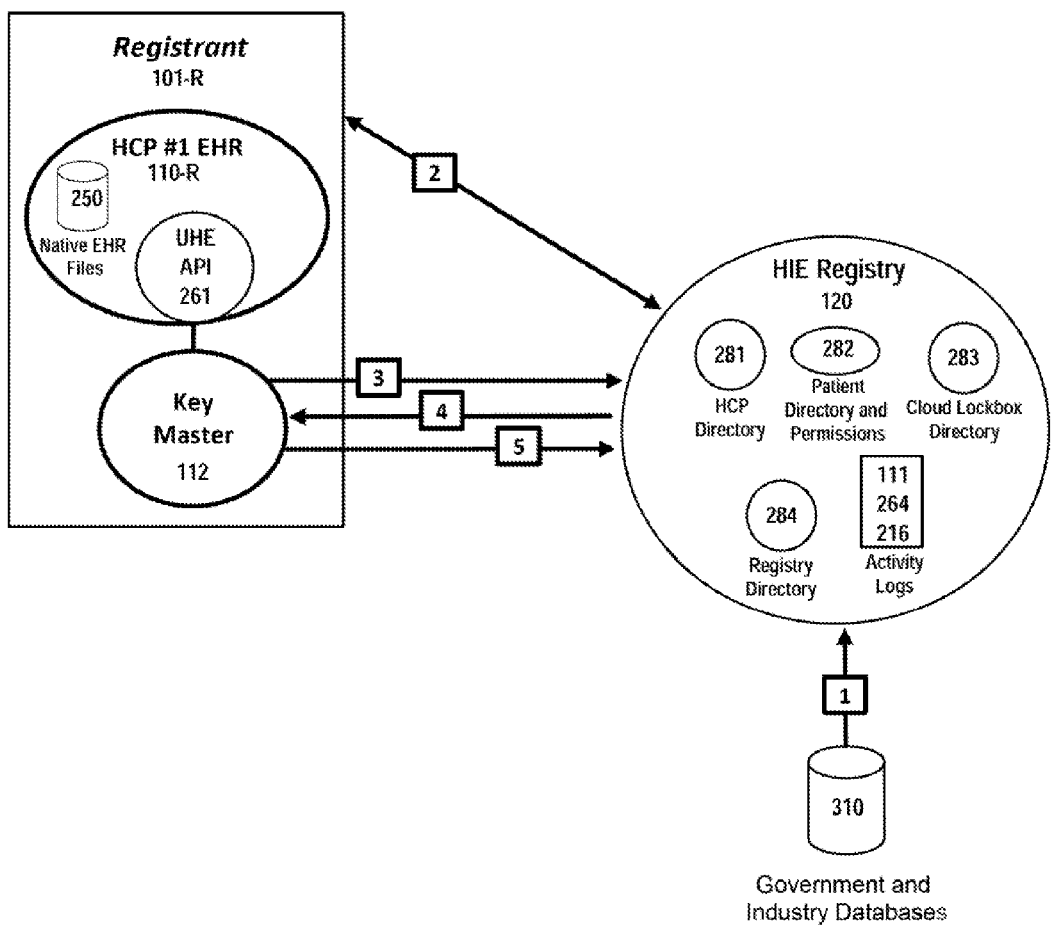
Figure 3: HCP Registration

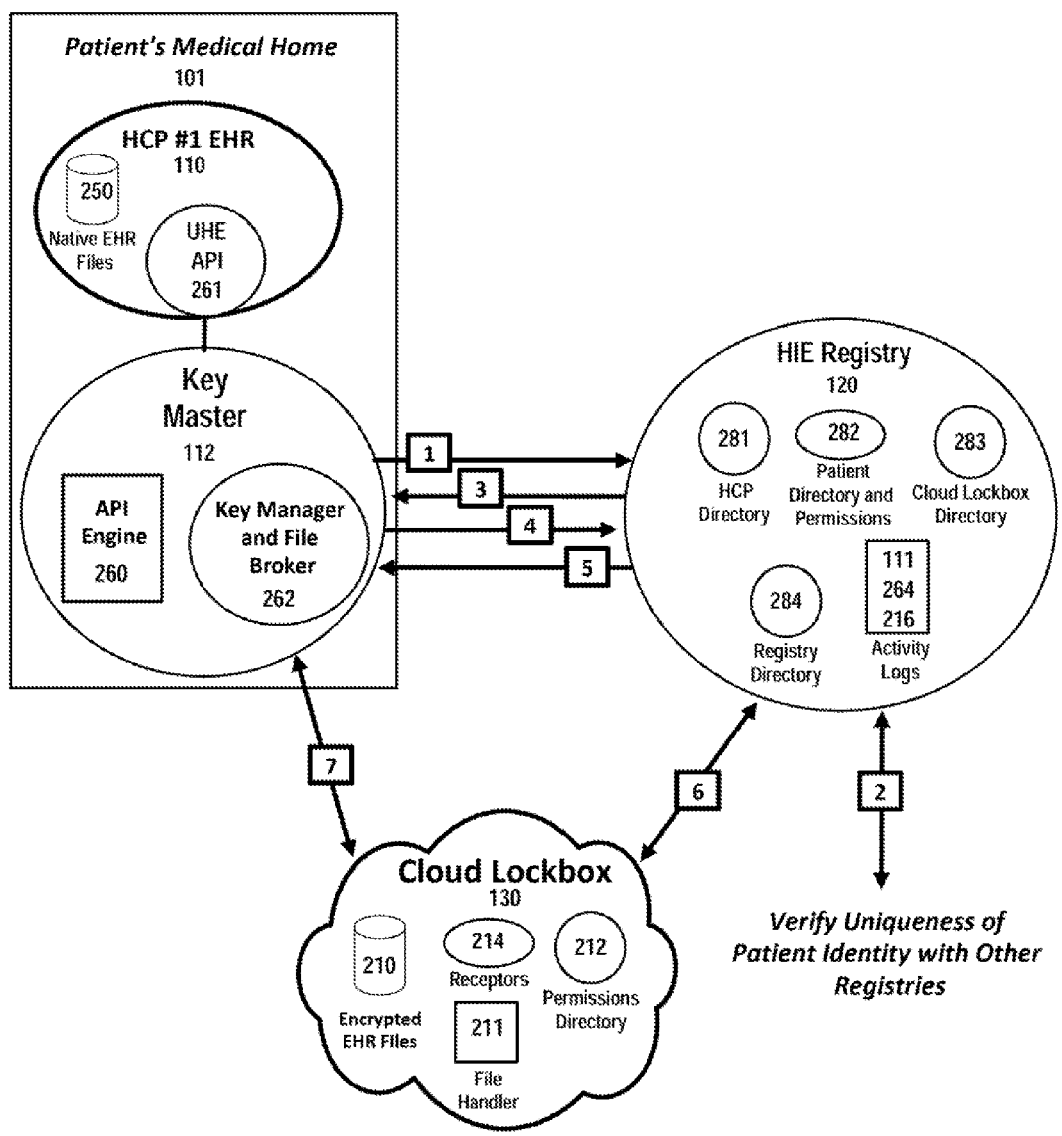
Figure 4: Registration of a Patient

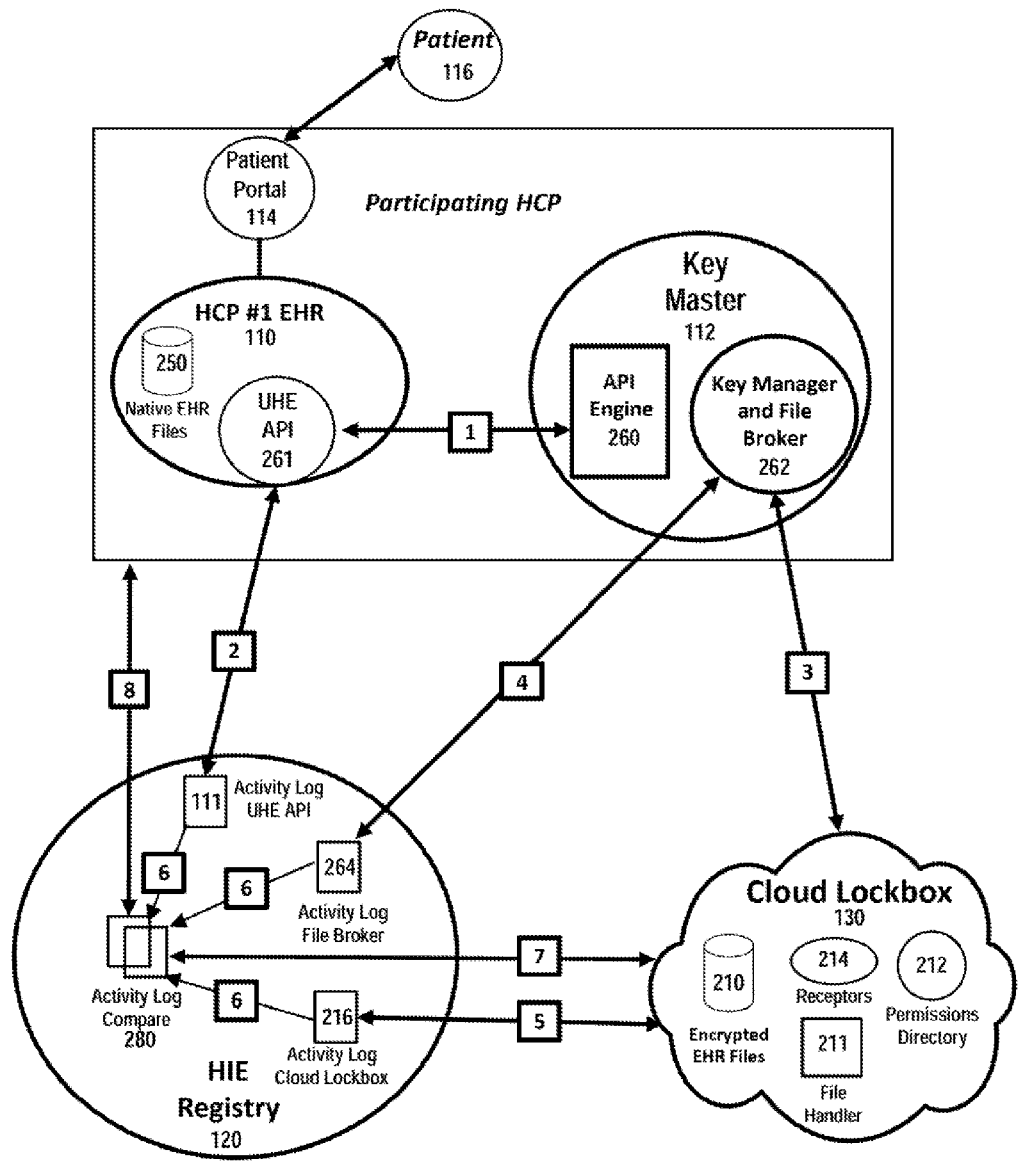
Figure 5: Activity Logs

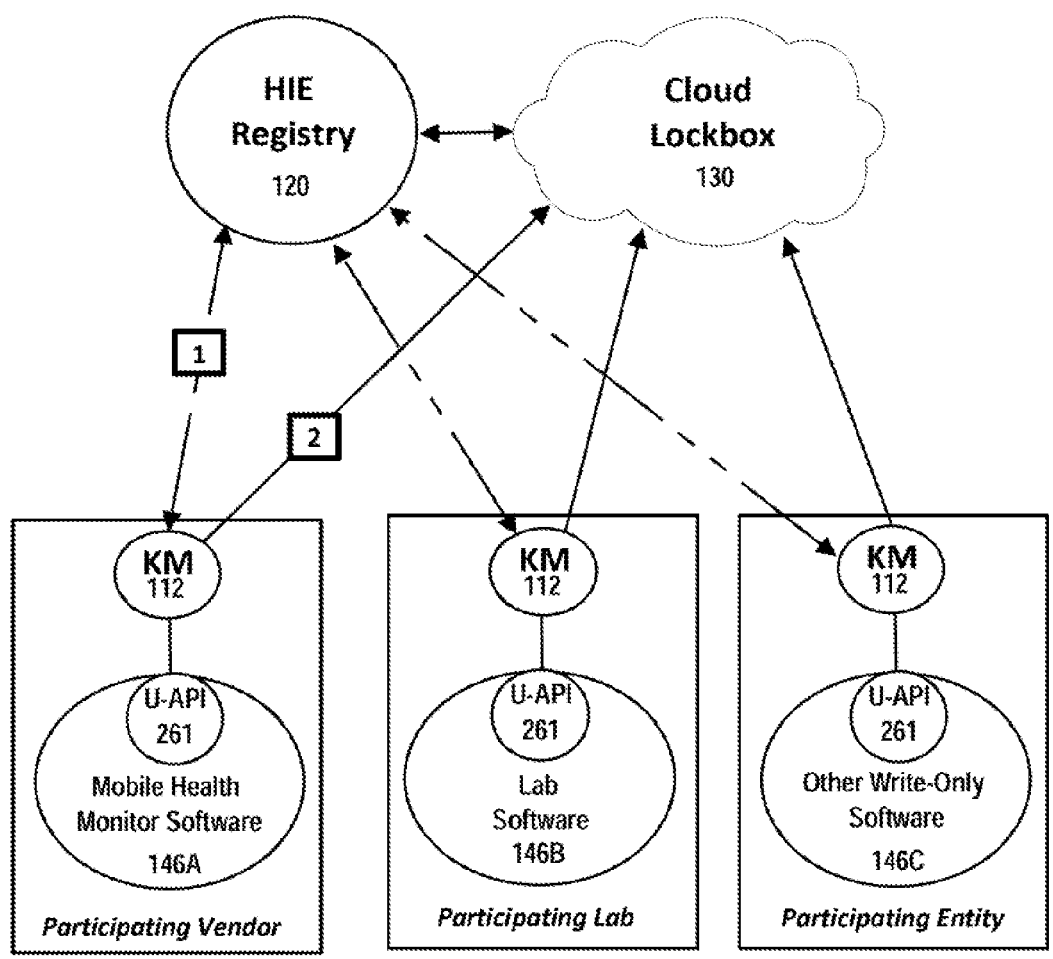
Figure 6: Write-Only Members

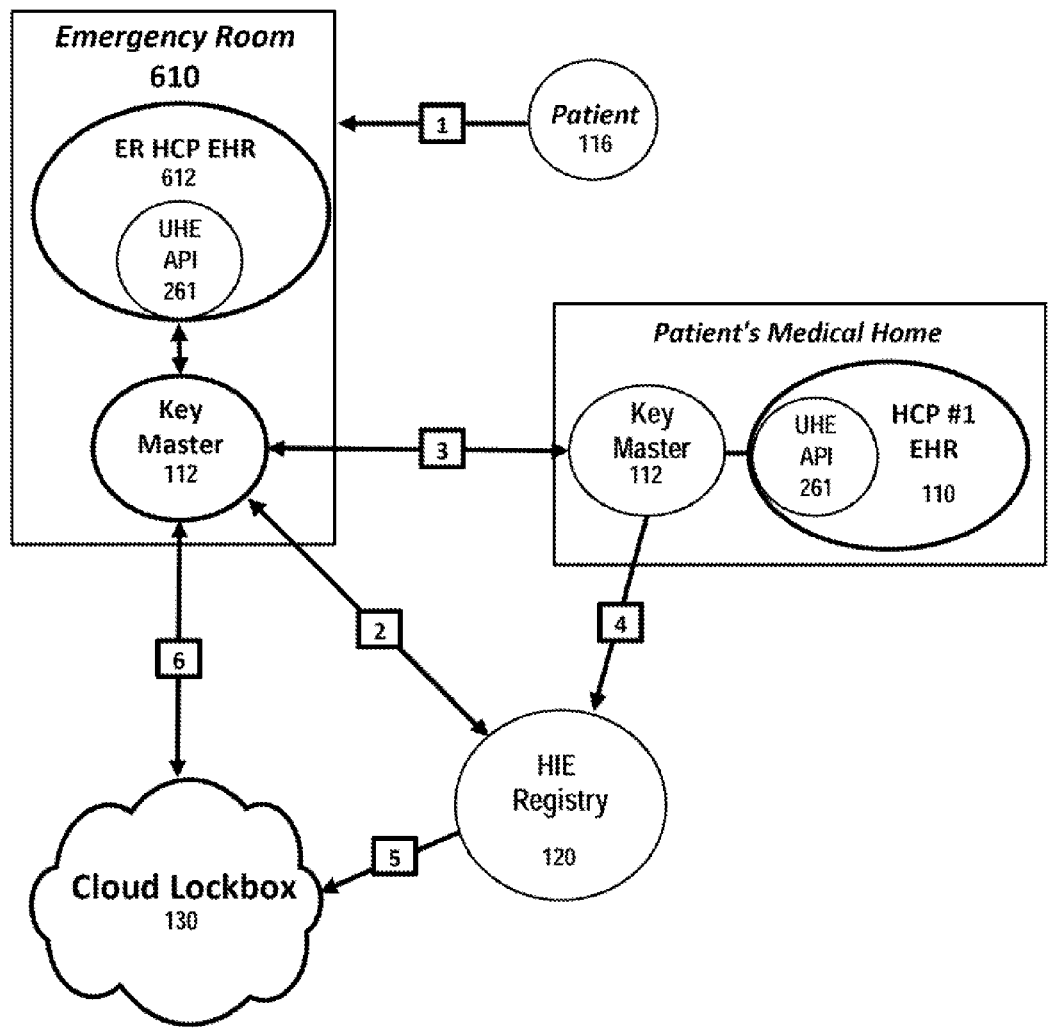
Figure 7: "Glass Break" Scenario

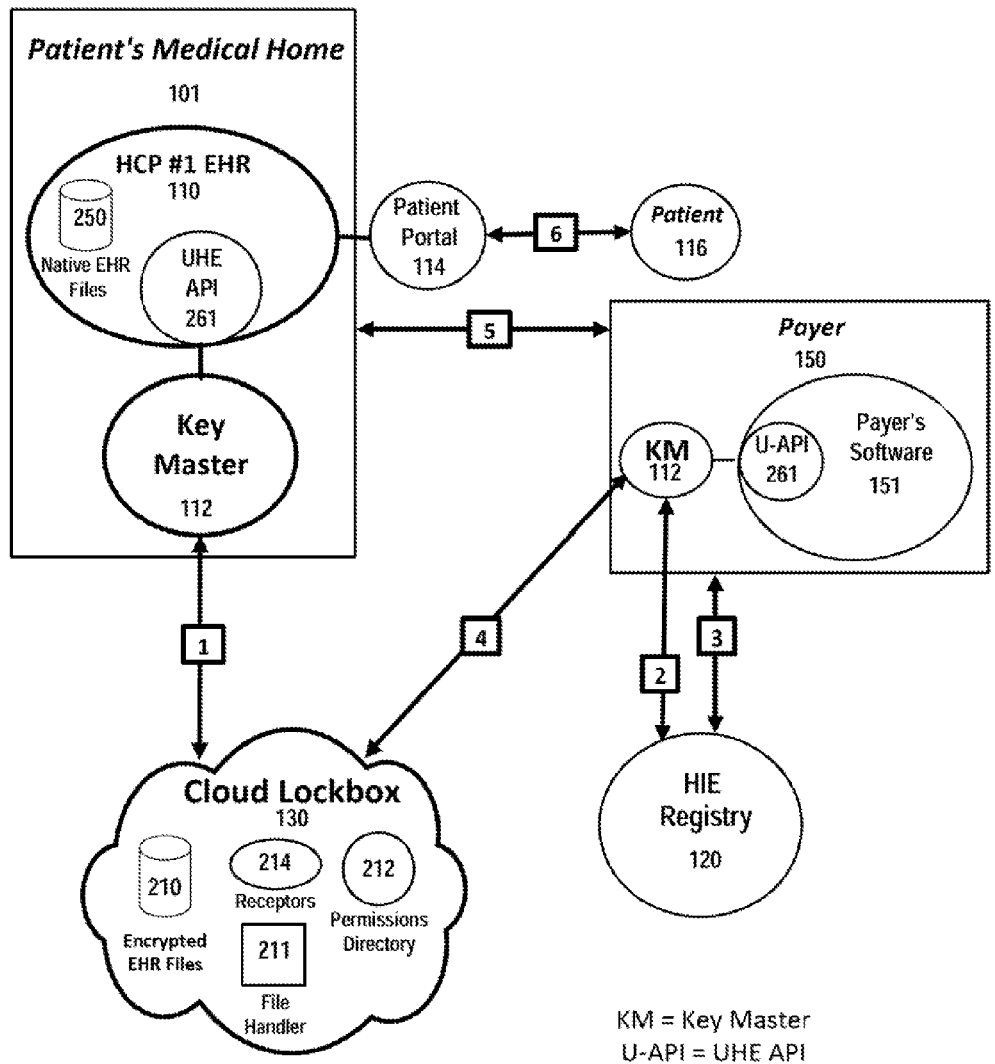
Figure 8 : Waste Fraud and Abuse Prevention

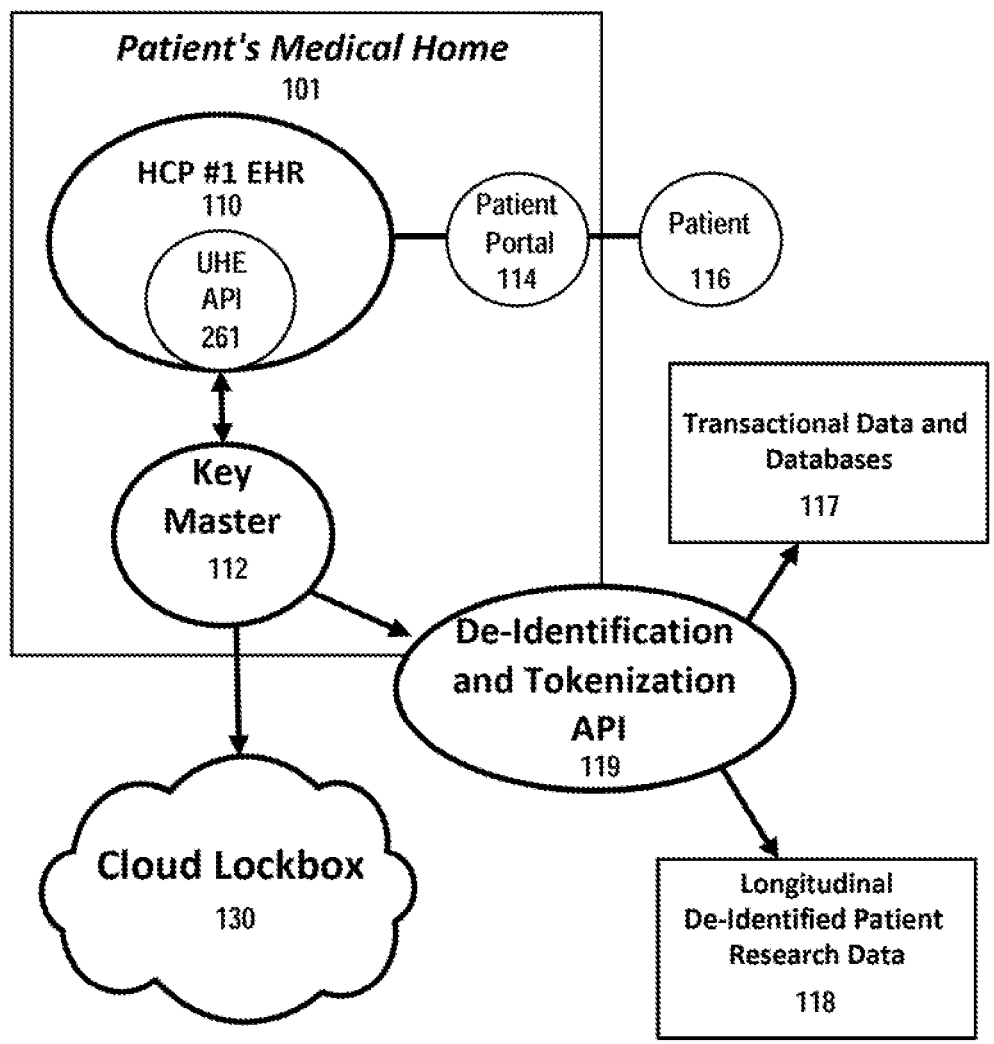
Figure 9: De-Identification and Tokenization

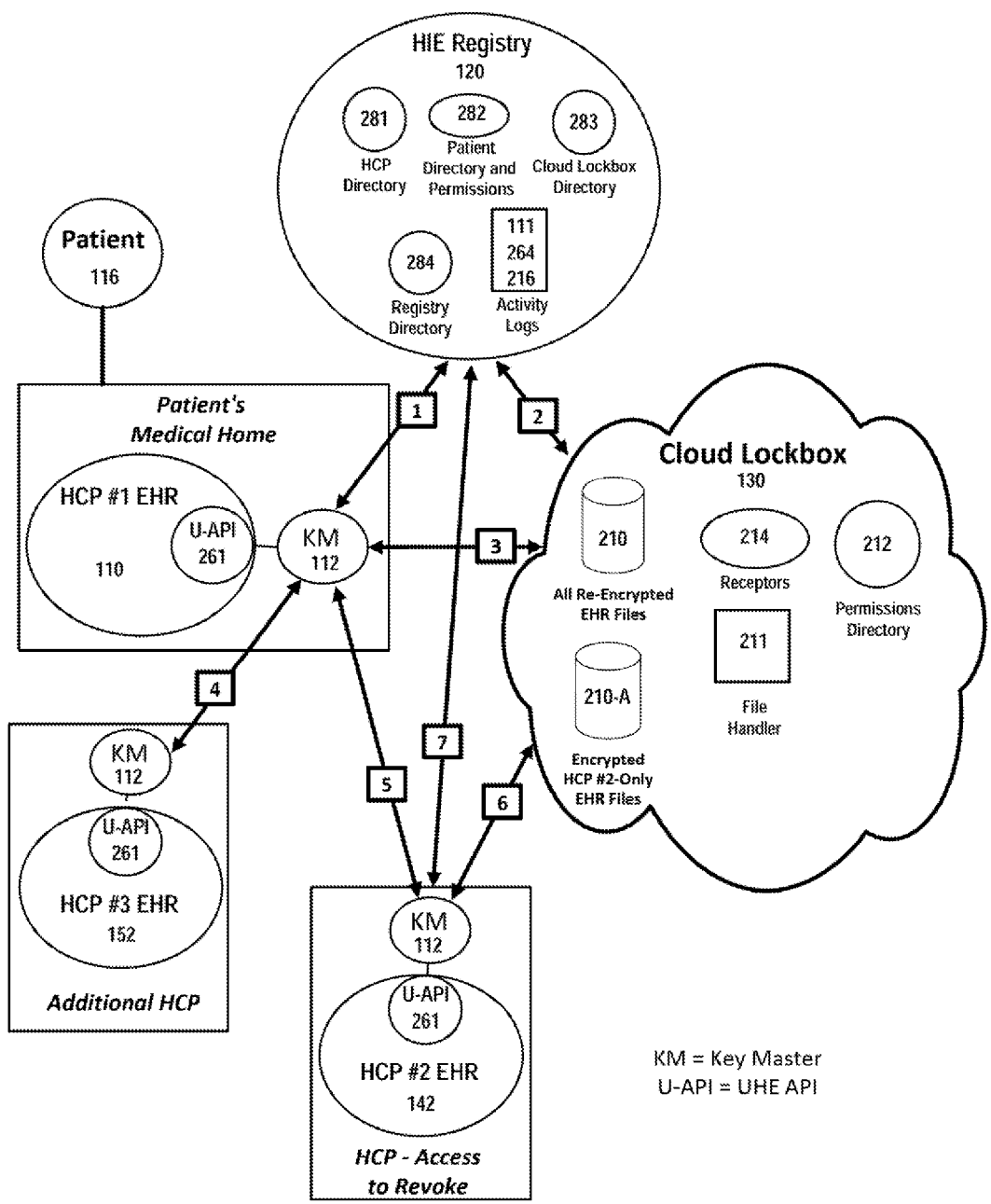
Figure 10: Key Change and/or Revoking Access

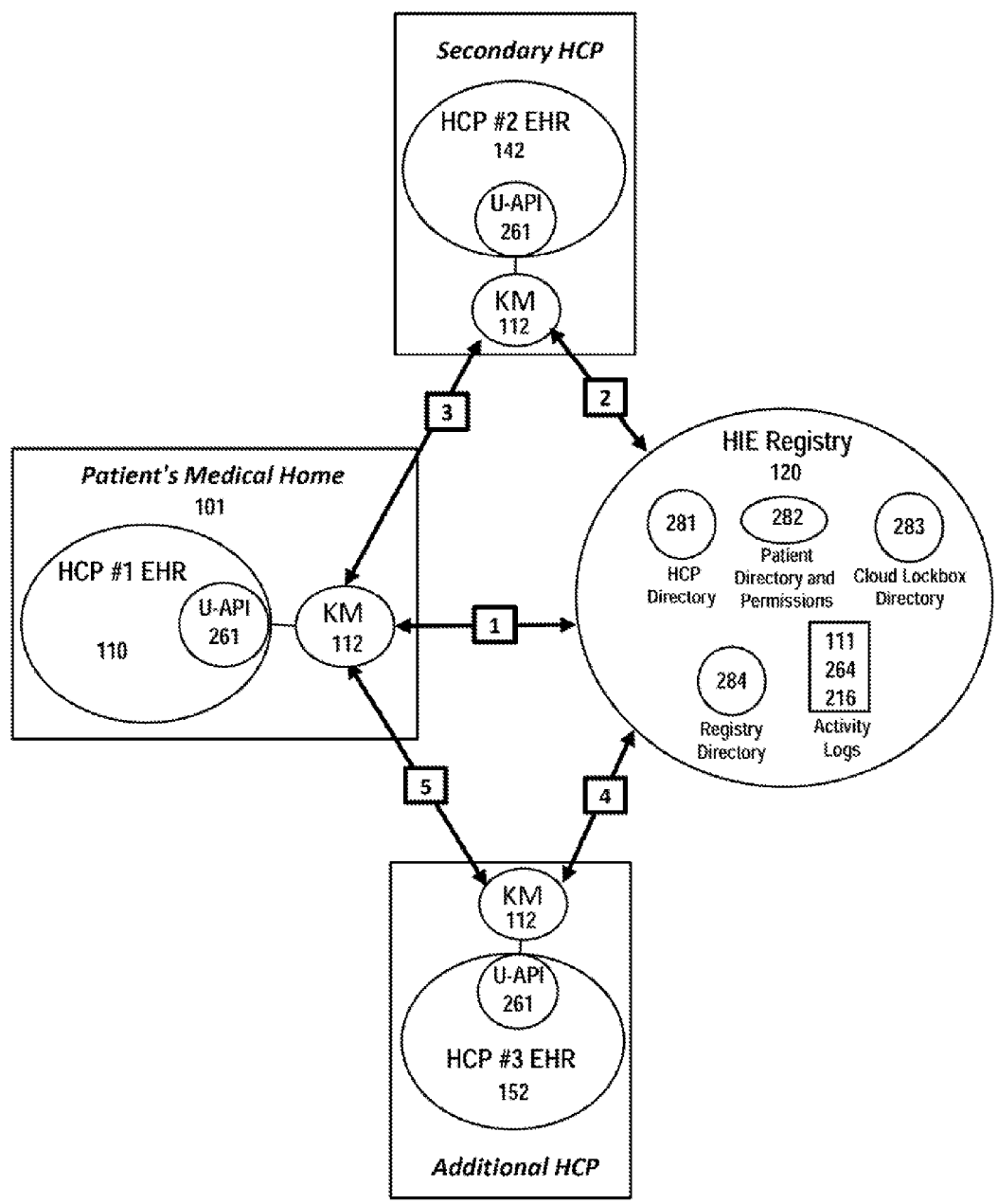
Figure 11: Key Recovery Processes

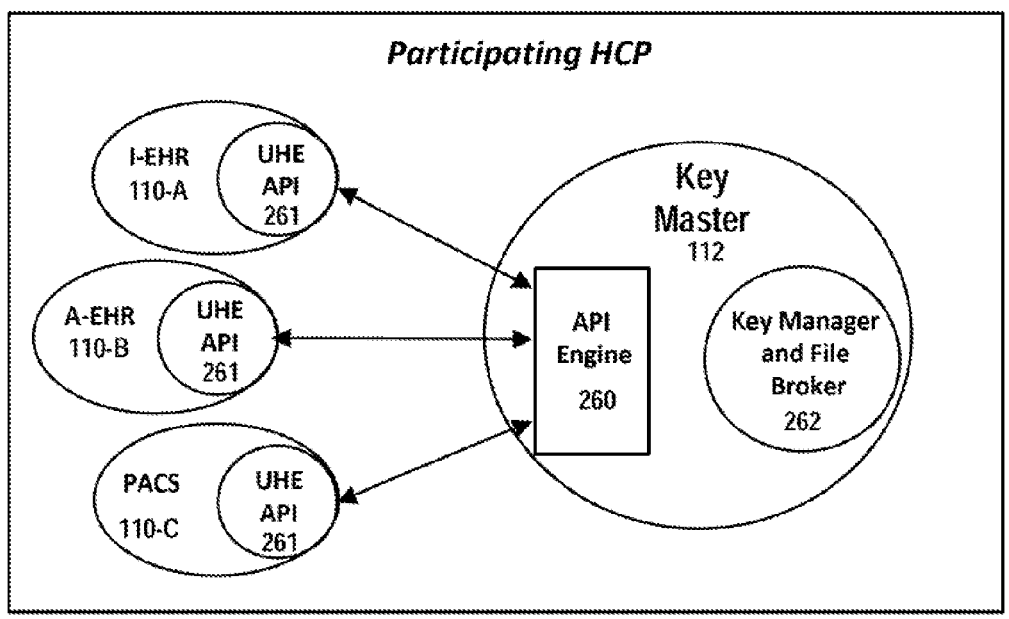
Figure 12: Multiple Software EHRs to a Single Key Master

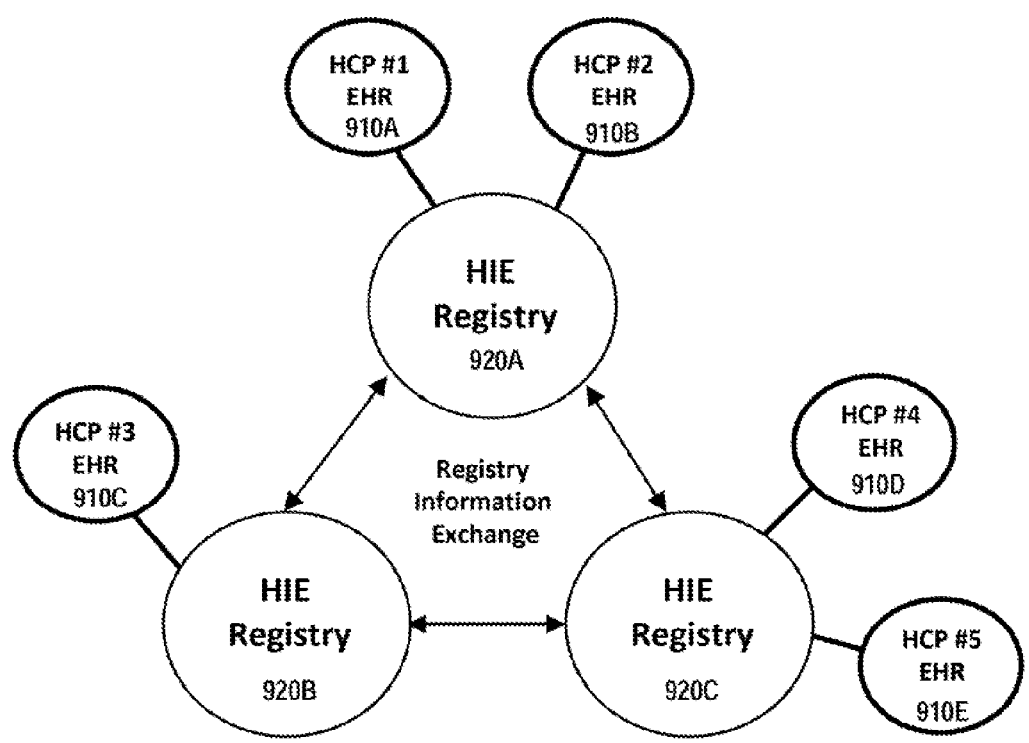
Figure 13: Registry-to-Registry Communications

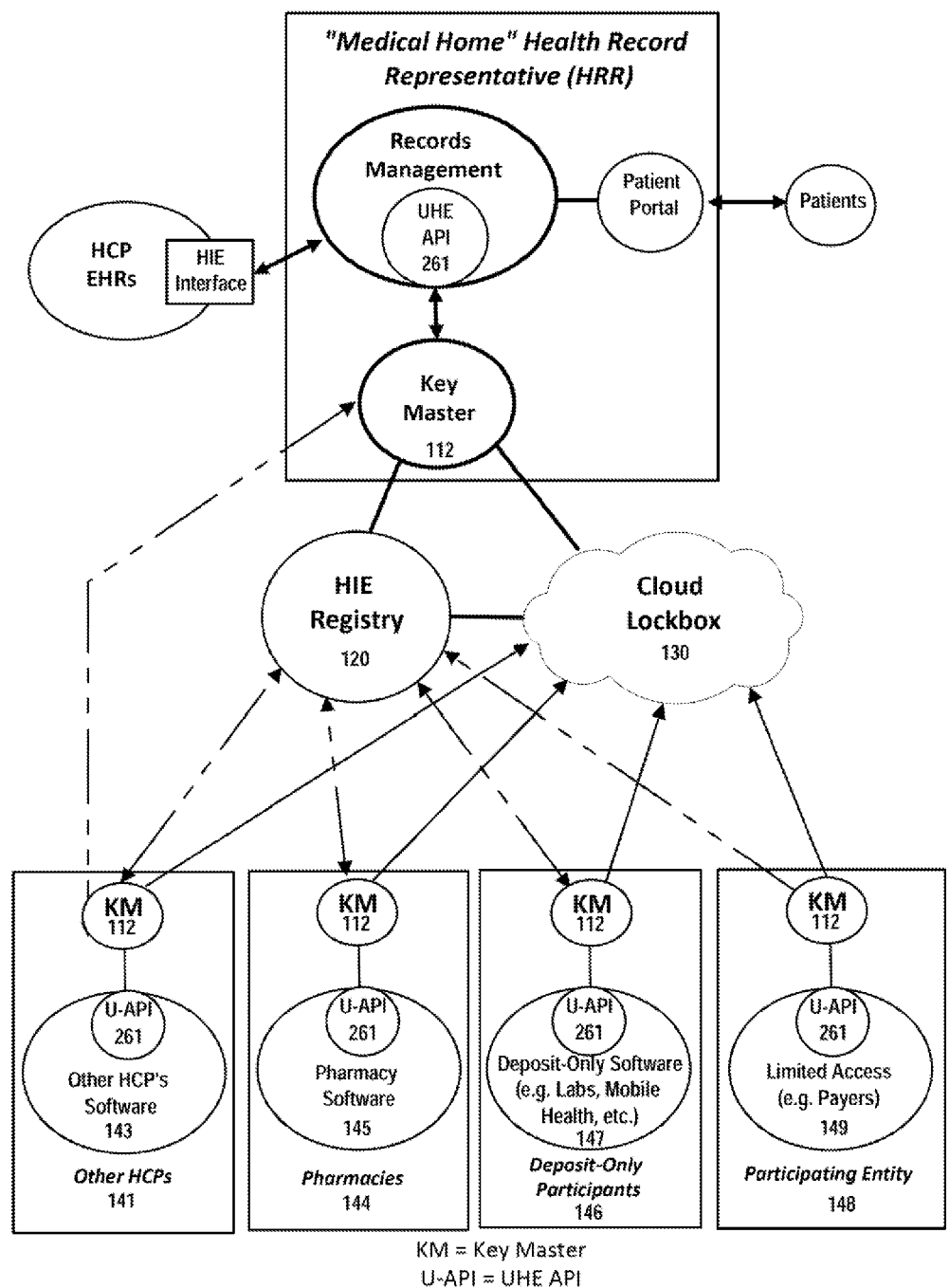
Figure 15: Health Record Representative Model

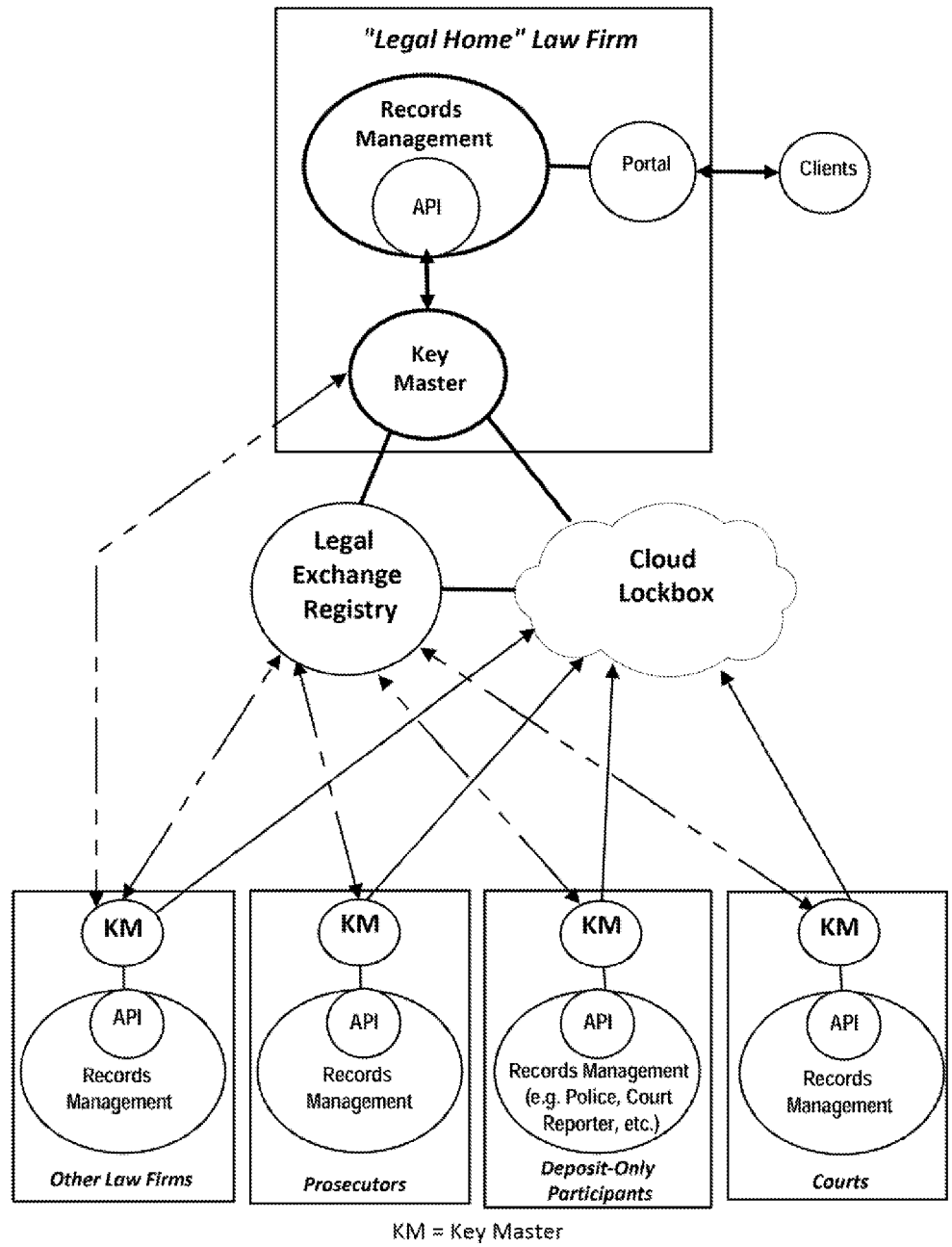
Figure 16: Legal Industry Model

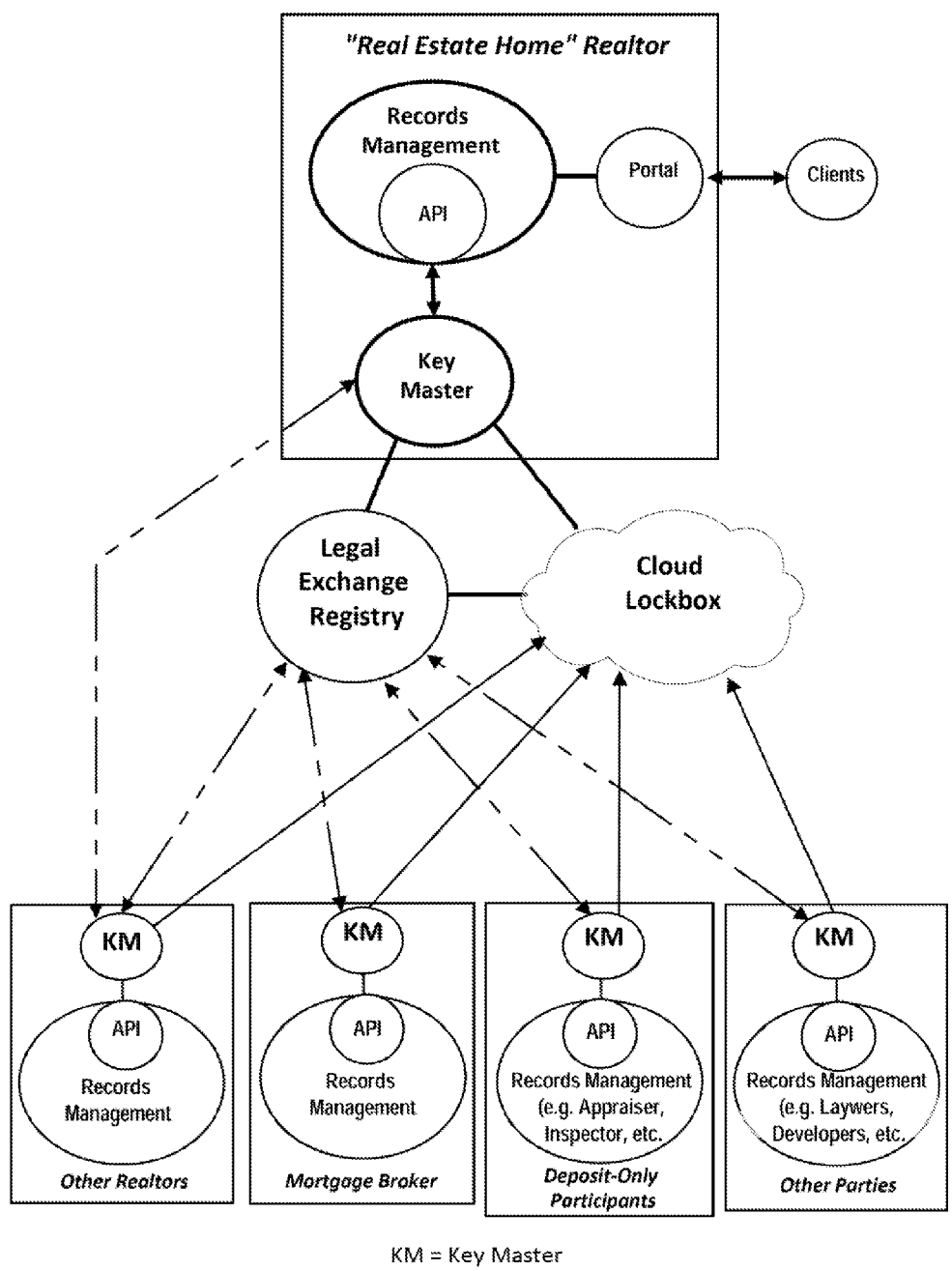
Figure 17: Real Estate Industry Model

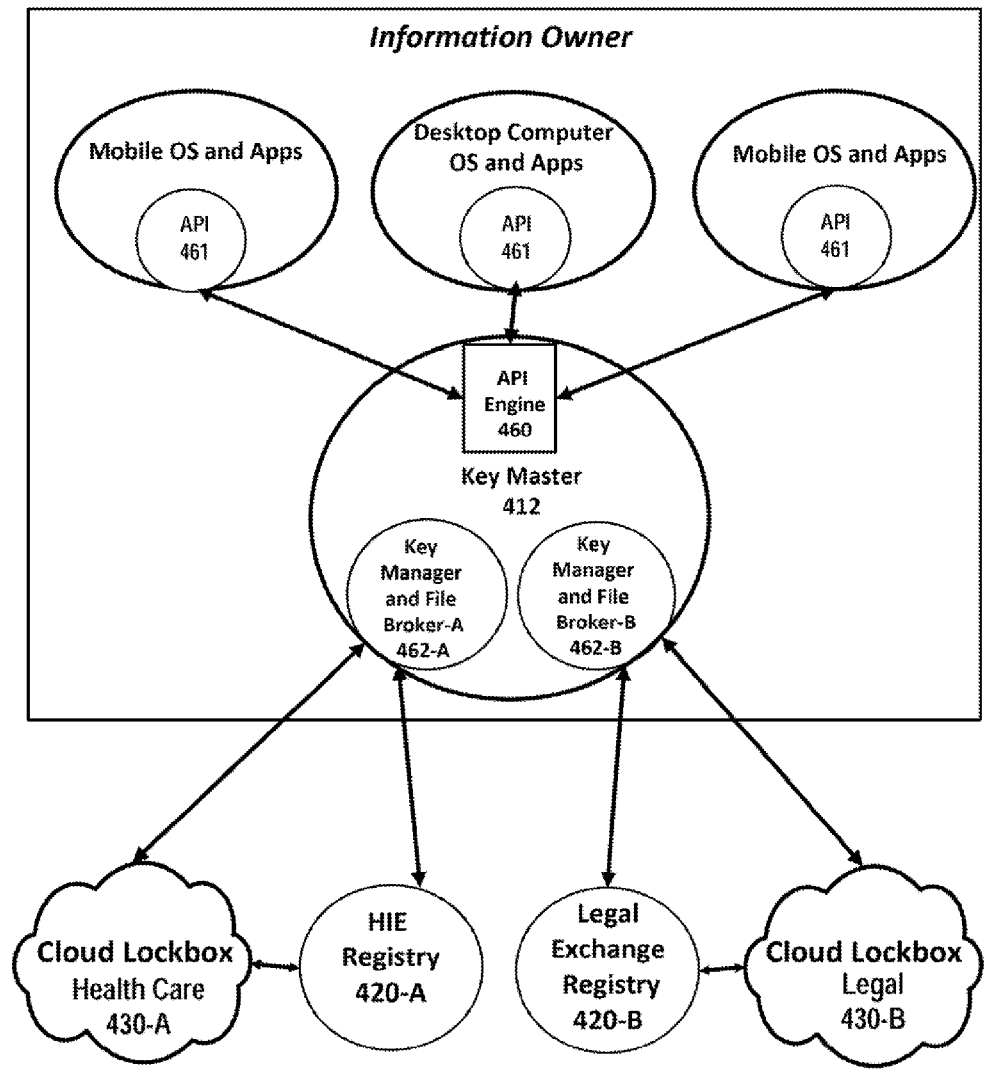
Figure 18: Information Owner Hosted and
Multiple Encryption Algorithms

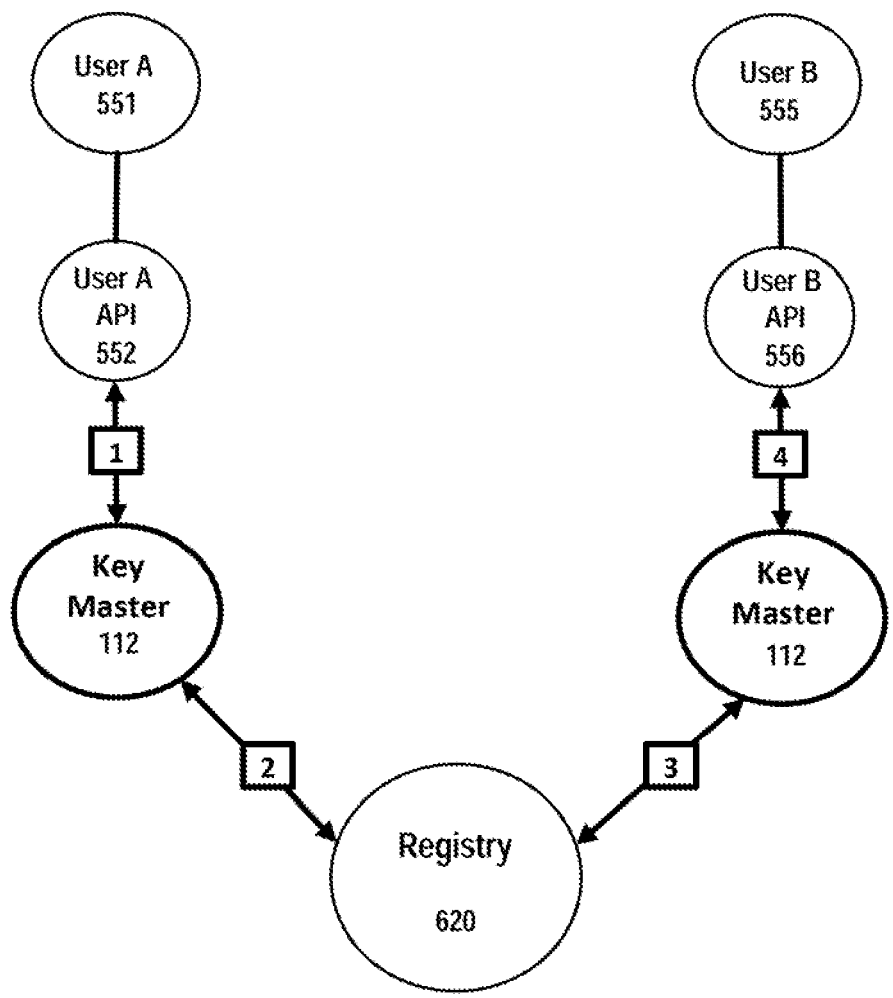
Figure 19: Key Master "Phone Home" Operations

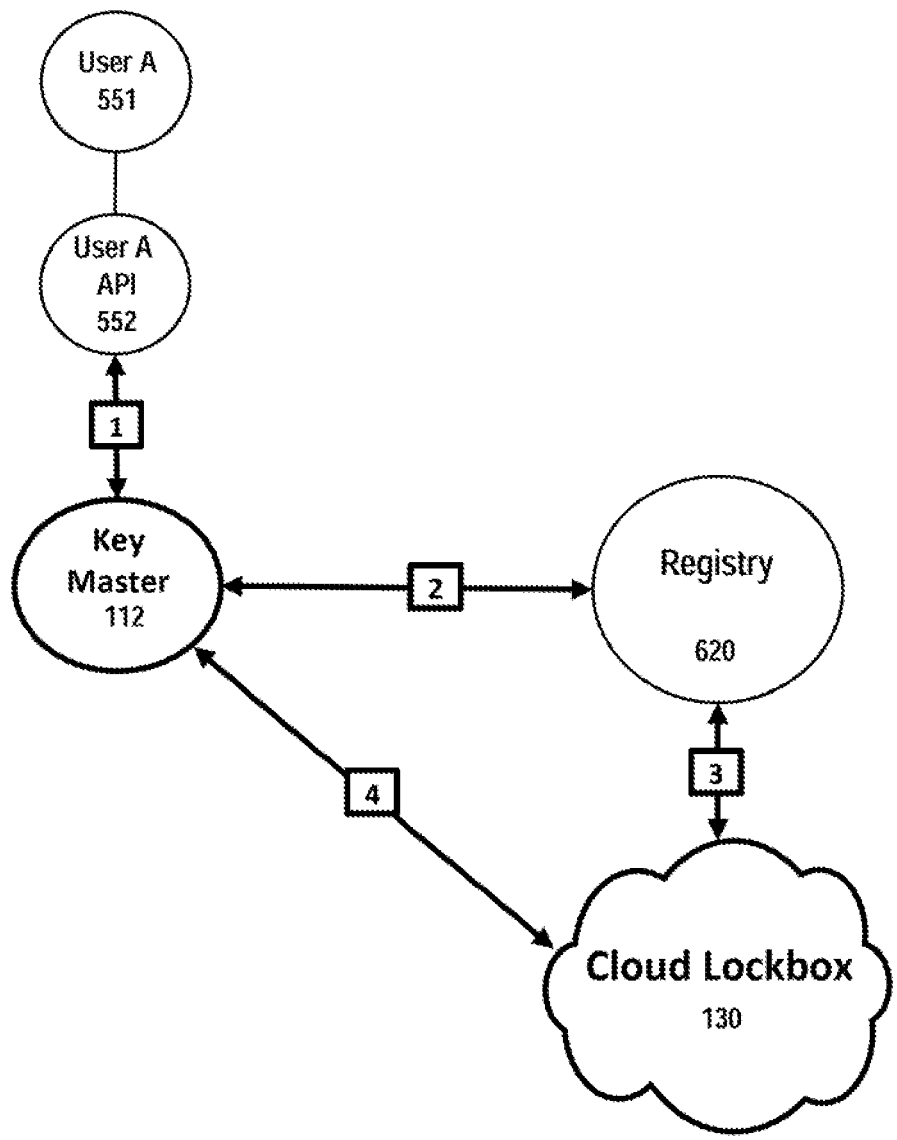
Figure 20: Deposit and Retrieve Alternative

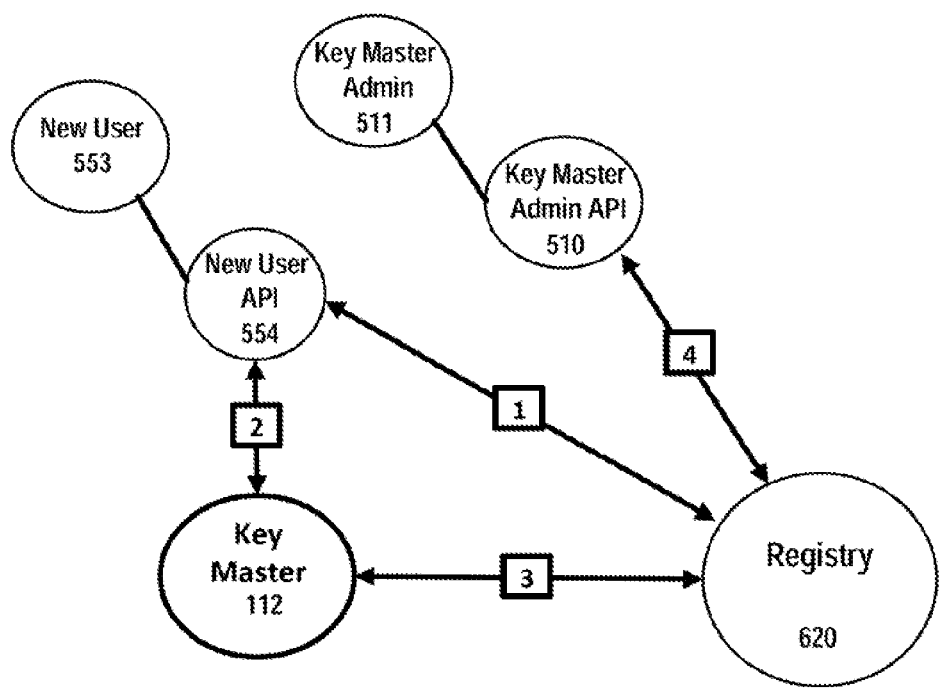
Figure 21: Adding A New User to Existing Key Master with a Key Master Admin API

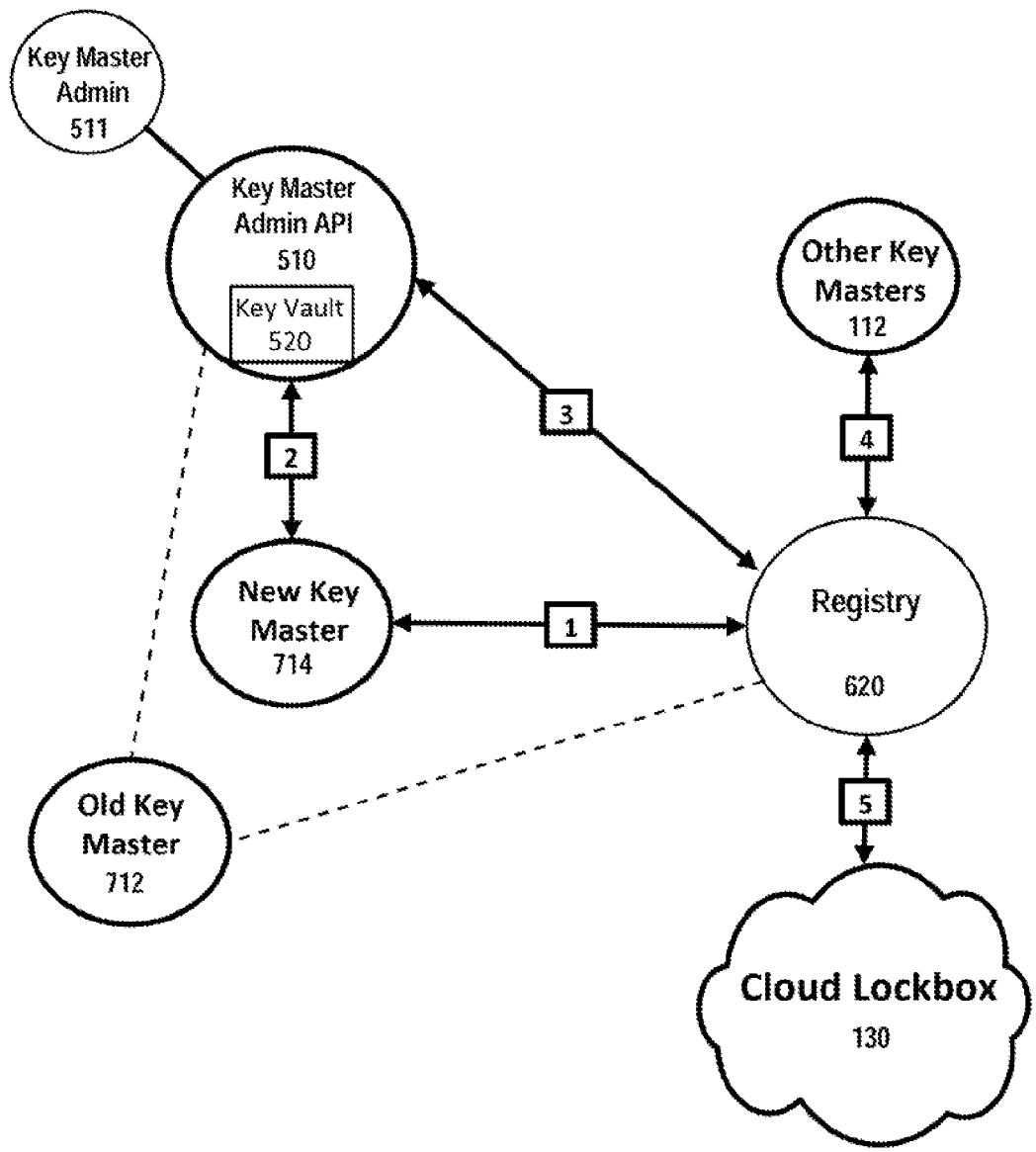
Figure 22: Key Vault

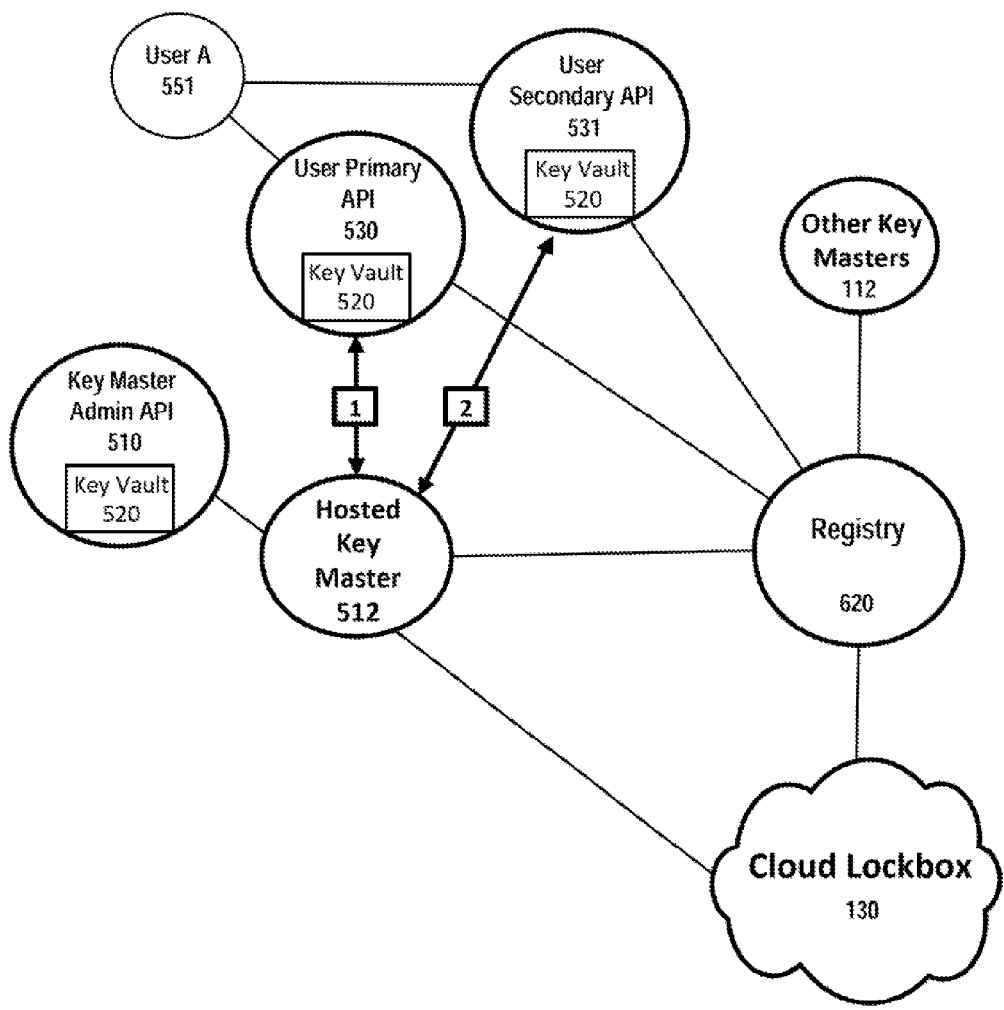
Figure 23: Hosted Key Master and Key Vaults

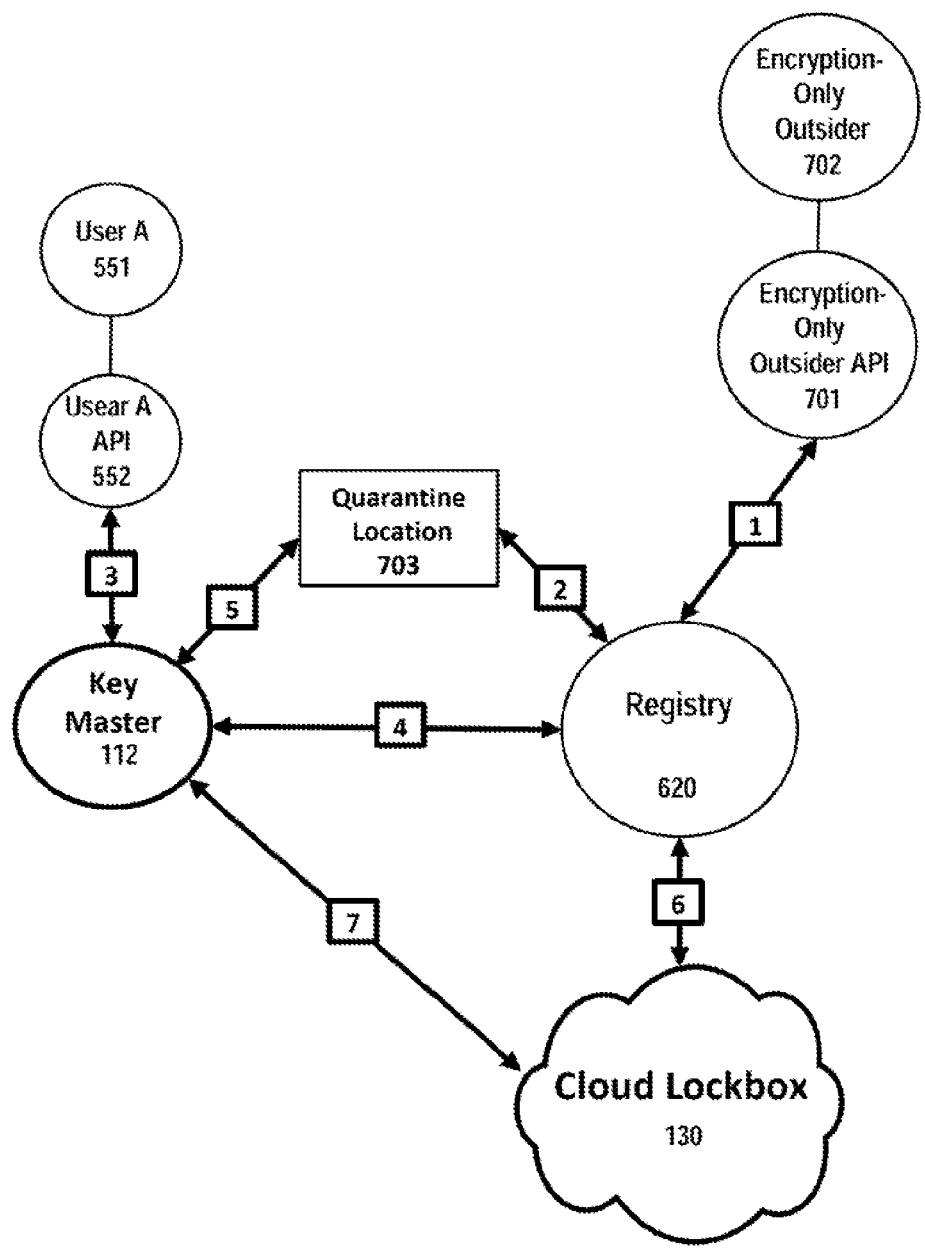
Figure 24: Deposit-Only Access for Parties Outside Community of Interest

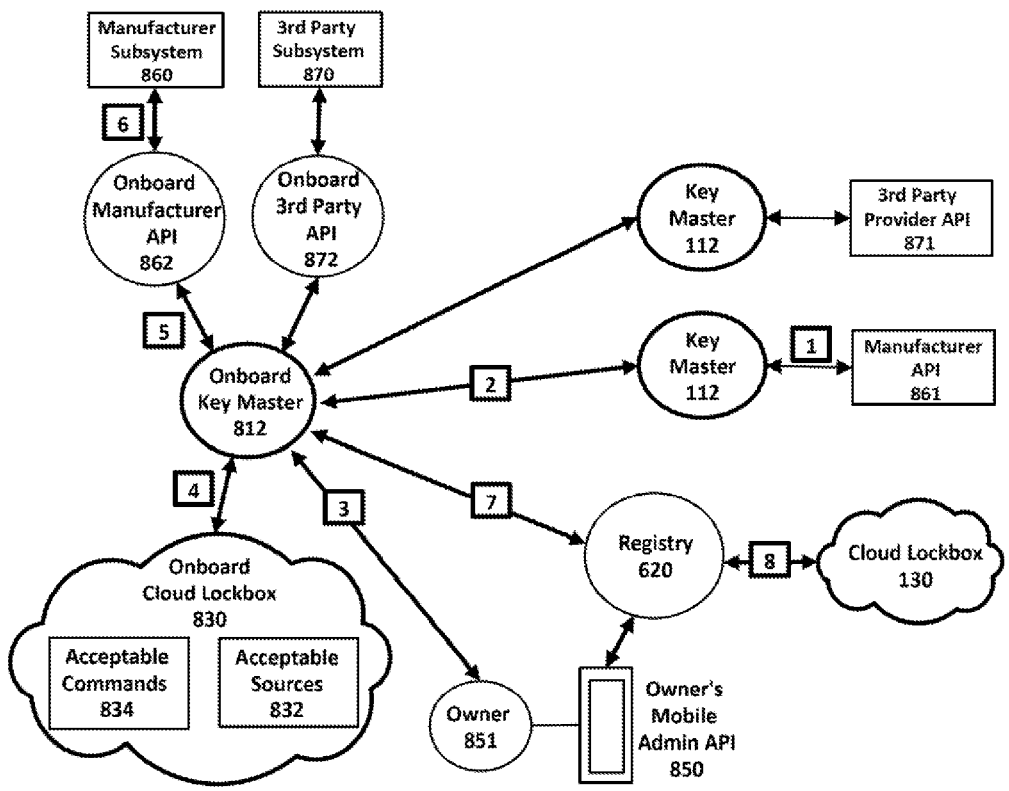
Figure 25: Modification of Mechanism to Secure the
Internet of Things

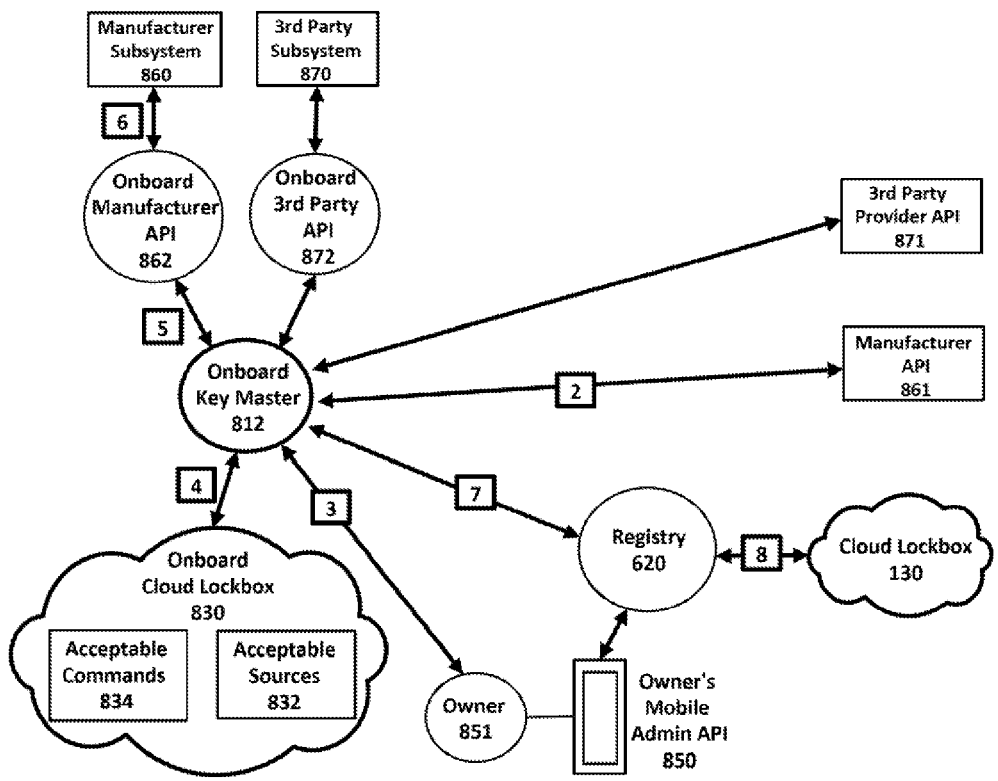
Figure 26: Truncated Mechanism to Secure the Internet of Things

SYSTEM AND METHOD FOR SECURELY STORING AND SHARING INFORMATION

CROSS-REFERENCE TO RELATED APPLICATIONS

This application is a continuation-in-part of U.S. application Ser. No. 14/539,614 filed on Nov. 12, 2014, which is a continuation-in-part of U.S. application Ser. No. 13/665,861 filed on Oct. 31, 2012, which claims priority to U.S. Provisional Patent Application Ser. No. 61/553,883 entitled "System and Method for Securely Storing and Sharing Information" filed Oct. 31, 2011, all of which are incorporated by reference in its entirety as if fully set forth herein.

TECHNICAL FIELD

The present application generally relates to systems, devices, and methods to conduct the secure exchange of encrypted data using a tightly coupled, distributed three-element-core consisting of the key masters, the registries and the cloud lockboxes. Application programming interfaces integrate the three-element-core with a wide variety of user-facing software applications. Together the three-element-core combined with the application programming interfaces provide full lifecycle encryption enabling cross-platform information sharing within and between organizations and individuals, applications and devices. A variation of the mechanism provides real-time protection for intelligent embedded systems such as those described as the Internet of Things.

More specifically, the registries verify the identity of, and the key masters assign a unique asymmetric key pair for, each individual, organization and device. Control of the private key required for decryption is maintained by the information owner's key master or key vault. The mechanism establishes unique identities, verifies authenticity, generates and securely exchanges asymmetric encryption key pairs, encrypts, transmits, receives and decrypts data to/from cloud lockboxes; creates and appends metadata specific to the applications and retrieves and/or act upon metadata. The related application programming interfaces support multiple levels of integration and generate metadata specific to the needs of the application. A community of interest establishes operating parameters including: selecting an encryption algorithm, establishing identity verification processes and selecting a security level. The design supports several other key features using operating protocols and/or metadata.

BACKGROUND

Certain methods and systems previously been used for securely storing and sharing confidential information. Some such systems employ cryptography, such as asymmetric encryption using public-private key pairs, to protect information.

Cryptography can provide strong protection, but the key exchange process makes sharing encrypted data clumsy and sometimes insecure. Weak, absent or disconnected identity verification also degrades the effectiveness. Existing practices for deployment of asymmetric public-private cryptography has hampered adoption and application of this useful encryption technology. The prevalent orthodoxy against sharing private keys constrains asymmetric encryption to being a point-to-point solution, one often too complex for the average user to engage.

Accordingly, there is a need for systems, methods and devices that provides a tightly coupled, distributed mechanism that splits the elements of control across three separate but interlocking computing envelopes achieving high security and integration flexibility to provide full lifecycle and cross-platform encryption within and between organizations, individuals, applications and devices.

In addition, a modification of the mechanism provides real-time protection for intelligent embedded systems.

SUMMARY

According to a first aspect of the present application, a method to conduct secure exchange of encrypted data using a tightly coupled, distributed three-element-core mechanism consisting of the key masters, the registries and the cloud lockboxes with the core mechanism integrating with a wide variety of user-facing application programming interfaces. The registries establish unique identities, verify authenticity, and create directories of individuals, members, organizations, key masters, cloud lockboxes and other registries. These directories may include public keys of all associated identities. The registries manage permissions lists for access to encrypted files and catalog locations of files. The registries also receive activity records from other elements of the mechanism and the application programming interfaces to provide an audit trail; and to detect and halt anomalous activity. The key master software instances, preferably provisioned as appliances, create and manage key pairs for itself, all other devices, individuals and organizations; perform encryption and decryption; and conduct key exchanges with the key masters of other members, a process that may utilize a secure relay. The cloud lockboxes manage encrypted files at rest, supporting any file system, with stored files located in one or more physical locations; create receptors for retrieval of stored files; utilize access controls of the mechanism as well as the underlying file system; and retrieve and deliver files in response to properly authorized file access requests. The related application programming interfaces support multiple levels of integration and generate metadata specific to the needs of the application.

According to the second aspect of the present application, a method for creating a community of interest is disclosed. Any community of interest can establish its own operating parameters including: selecting an asymmetric encryption algorithm, selecting a registry or registries, establishing related membership requirements and identity verification processes, selecting a cloud storage provider or providers, selecting the optional security features, and determining the minimum application integration levels.

According to the third aspect of the present application, a method for creating features through protocols operating among the three-element-core, application programming interfaces, parties and metadata is disclosed. The protocols and metadata enable features including: detection and halting of anomalous access, time-to-live settings on the sharing of data; key change and access revocation processes; key and file recovery processes, tokenization of personal identifiers for use in transactional data and databases, de-identification of data to feed research databases, and emergency access protocols. The design supports addition of features by leveraging existing design elements and expanding operating protocols and metadata.

According to the fourth aspect of the present application, a method for minimizing the exposure of data to system administrators is disclosed. The protected data is encrypted by the key master, prior to reaching the registry or cloud lockbox; and the registry and cloud lockbox never have access to the decryption keys; thus the system administrators performing duties for optimization and maintenance of the cloud lockboxes have access to the encrypted data but do not have the decryption keys, nor do they know the identities of the owners of the data. Similarly, the system administrators performing duties for optimization and maintenance of the registry do not have access to the decryption keys nor persistent access to the encrypted data. Further when application owners elect to integrate the present application into their native file systems, the benefits of this aspect extend into the premise-based, private cloud-based or public cloud-based storage of the application itself.

According to the fifth aspect of the present application, a method for managing key masters is disclosed. An administrative application programming interface operated by the owner or administrator of the key master that communicates with both the key master and the registry will support key master activation; approval of new users of the key master; and receiving alerts regarding operations of the key master.

According to the sixth aspect of the present application, a method for backing up and restoring private keys is disclosed. Using an administrative application programming interface or a user application programming interface, private keys may be securely stored in a key vault for restoration of keys in the event of corruption or loss of private keys.

According to the seventh aspect of the present application, a method for integrating with applications and creation of hybrid cloud and on-premise data storage solutions is disclosed. The invention provides robust approaches for the integration of an application into the community of interest by providing both published and unpublished application programming interfaces supporting multiple levels of application integration ranging from native integration to the use of industry-standard interfaces to simple archiving solutions. The method facilitates the creation of hybrid cloud and on-premise storage solutions with predictive caching; and provides a method to integrate disparate applications within a single enterprise or across multiple enterprises.

According to the eighth aspect of the present application, a method for providing real-time protection to intelligent embedded systems is disclosed.

According to the ninth aspect of the present application, a method for offering a variety of security levels is disclosed. The invention can be deployed in various ways to achieve the security level desired by the community of interest ranging from:
  a. the stringent Federal Information Processing Standards 140-2 Level 4;
  b. rigorous civilian standards for protecting confidentiality such as Health Information Portability and Accountability Act;
  c. relatively low level security required for non-sensitive information.

The design traverses these various security levels based on:
  a. Deploying the key masters as appliances thus keeping critical processes such as key management, encryption and decryption within a hardened environment rather than running this software in a general purpose operating system;
  b. Use of multi-factor authentication including biometric measures;
  c. Use of messaging to/from mobile devices in multi-factor authentication;
  d. Depth of integration with the applications;
  e. Optional registered IP address restrictions.

BRIEF DESCRIPTION OF THE FIGURES

The accompanying figures, which are incorporated in and constitute a part of the specification, illustrate various example systems, devices methods, and so on, and are used merely to illustrate various example embodiments. It should be noted that various components illustrated in the figures may not be drawn to scale, and that the various assemblies and designs illustrated in the figures are presented for purposes of illustration only, and should not be considered in any way as limiting.

FIG. 2 is a schematic block diagram further illustrating operation of the UHE of FIG. 1.

FIG. 3 is a schematic block diagram illustrating an HCP registration process using the UHE of FIG. 1.

FIG. 4 is a schematic block diagram illustrating a patient registration process using the UHE of FIG. 1.

FIG. 5 is a schematic block diagram illustrating the use of activity logs using the UHE of FIG. 1.

FIG. 6 is a schematic block diagram illustrating sharing deposit-only data using the UHE of FIG. 1.

FIG. 7 is a schematic block diagram illustrating communications in an emergency situation using the UHE of FIG. 1.

FIG. 8 is a schematic block diagram illustrating mechanisms for identifying fraud, waste and abuse using the UHE of FIG. 1.

FIG. 9 is a schematic block diagram illustrating the de-identification and tokenization of patient data using the UHE of FIG. 1.

FIG. 10 is a schematic block diagram illustrating the key change and/or revocation of access using the UHE of FIG. 1.

FIG. 11 is a schematic block diagram illustrating the key recovery process using the UHE of FIG. 1.

FIG. 12 is a schematic block diagram illustrating the ability to support multiple participant software modules using the UHE of FIG. 1.

FIG. 13 is a schematic block diagram illustrating the operation of multiple registries within a community of interest.

FIG. 15 is a schematic block diagram illustrating other alternate environments for the systems, devices and methods of the present application.

FIG. 16 is a schematic block diagram illustrating an alternate environment for the systems, devices and methods of the present application for use in the legal industry.

FIG. 17 is a schematic block diagram illustrating an alternate environment for the systems, devices and methods of the present application for use in the real estate industry.

FIG. 18 is a schematic block diagram illustrating individual information owner control and use of multiple encryption algorithms to participate in multiple communities of interest from a single key master.

FIG. 19 is a schematic block diagram illustrating an alternative method for communications of the Key Masters using a "phone home" function thus using the Registry as a secure relay.

FIG. 20 is a schematic block diagram illustrating an alternative file deposit and retrieve methodology using the Registry as a secure relay.

FIG. 21 is a schematic block diagram illustrating use of a key master administrative application programming interface for adding a user to an existing key master.

FIG. 22 is a schematic block diagram illustrating the creation and use of a key vault in conjunction with the key master administrative application programming interface.

FIG. 23 is a schematic block diagram illustrating the use of a hosted key master and key vaults managed by a user's application programming interface.

FIG. 24 is a schematic block diagram illustrating a method for providing deposit-only access to individuals or entities outside of the community of interest.

FIG. 25 is a schematic block diagram illustrating the modification of the mechanism to provide real-time protection for intelligent embedded systems.

FIG. 26 is a schematic block diagram illustrating a truncated version of the modified mechanism to provide real-time protection for intelligent embedded systems.

FIGURE REFERENCE NUMERALS

Figure 1:
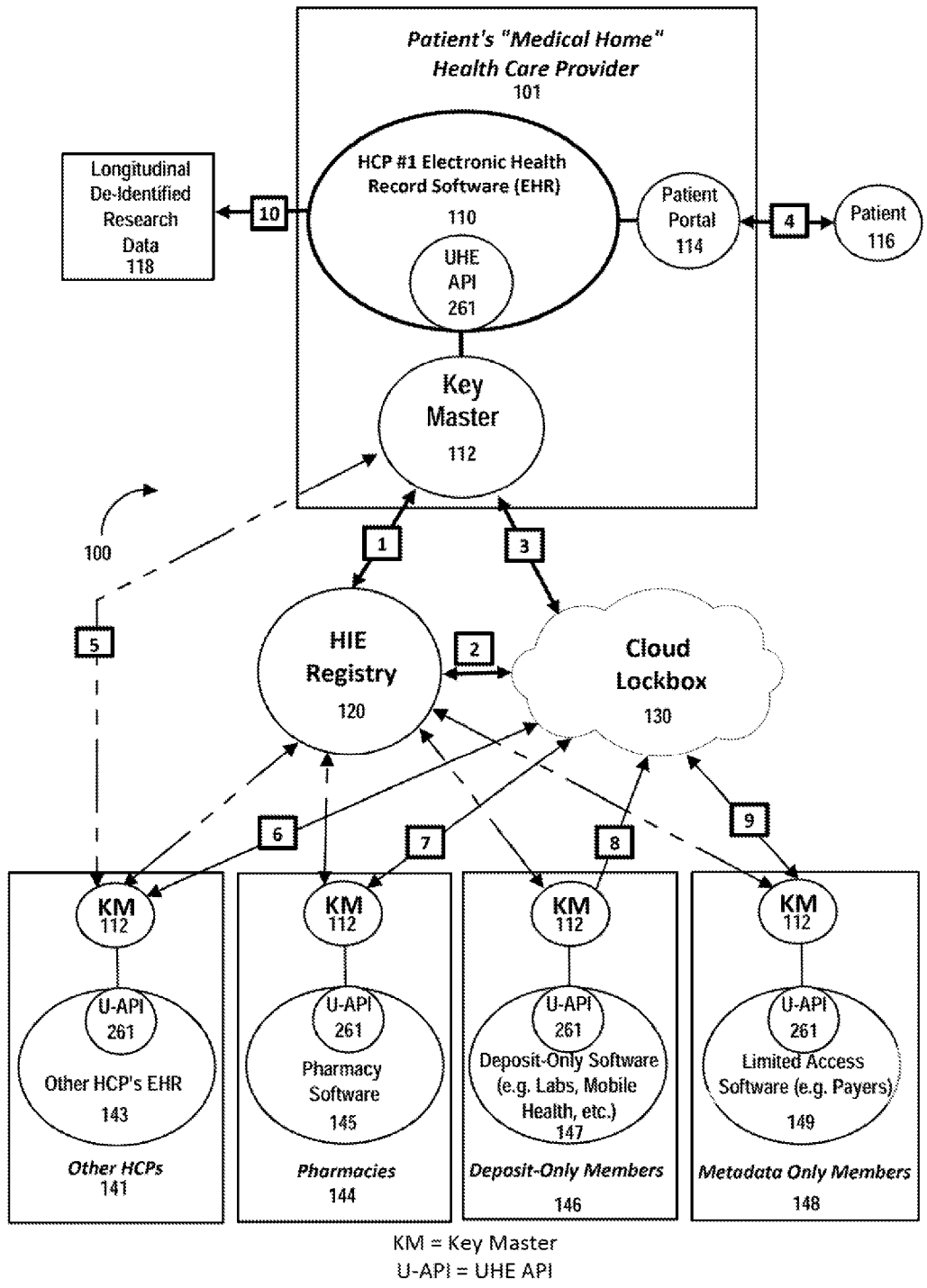
FIG. 1 is a schematic block diagram illustrating an example environment for the systems, devices and methods of the present application.

The following reference characters identify the associated elements depicted in the figures describing the present invention.

| | |
|---|---|
| 100 | Exemplary environment |
| 101 | Medical Home HCP |
| 101-R | HCP Registrant |
| 110-R | EHR Software of HCP Registrant (HCP#1 EHR) |
| 110 | HCP #1 Electronic Health Record Software |
| 110-A | Inpatient Electronic Health Record Software (I-EHR) |
| 110-B | Ambulatory Electronic Health Record Software (A-EHR) |
| 110-C | Picture Archiving Software (PACS) |
| 111 | Activity Log UHE API |
| 112 | Key Master (KM) |
| 114 | Patient Portal |
| 116 | Patient |
| 117 | Transactional Data and Databases |
| 118 | Longitudinal De-Identified Research Data |
| 119 | De-Identification and Tokenization API |
| 120 | HIE Registry |
| 130 | Cloud Lockbox |
| 140 | Secondary HCP |
| 141 | Other HCPs |
| 142 | HCP #2 EHR |
| 143 | Other HCP's EHR |
| 144 | Pharmacies |
| 145 | Pharmacy Software |
| 146 | Deposit-Only-Members |
| 147 | Deposit-Only Software (e.g. Labs, Mobile Health, etc.) |
| 146A | Mobile Health Monitor Software |
| 146B | Lab Software |
| 146C | Other Deposit-Only Software |
| 148 | Metadata-Only Members |
| 149 | Metadata-Only Software (e.g. Payers) |
| 150 | Payer |
| 151 | Payer's Software |
| 152 | HCP #3 EHR |
| 210 | Encrypted EHR Files |
| 210-A | Encrypted HCP #2 Files |
| 211 | File Handler |
| 212 | Permissions Directory |
| 214 | Receptors |
| 216 | Activity Log Cloud Lockbox |
| 250 | Native EHR Files |
| 260 | API Engine |
| 261 | Unified Health Exchange (UHE) Application Programming Interface (UHE-API) (U-API) |
| 262 | Key Manager and File Broker |
| 264 | Activity Log File Broker |
| 281 | HCP Directory |
| 282 | Patient Directory and Permissions |
| 283 | Cloud Lockbox Directory |
| 284 | Registry Directory |
| 310 | Government and Industry DBs |
| 412 | Information Owner Key Master |
| 420-A | HIE Registry—Health Care Community-of-Interest |
| 420-B | Legal Exchange Registry—Legal Community-of-Interest |
| 430-A | Cloud Lockbox for Health Care Community-of-Interest |
| 430-B | Cloud Lockbox for Legal Community-of-Interest |
| 460 | API Engine |
| 461 | Application Programming Interface |
| 462-A | Key Manager and File Broker-A |
| 462-B | Key Manager and File Broker-B |
| 510 | Key Master Admin API |
| 511 | Key Master Admin |
| 512 | Hosted Key Master |
| 520 | Key Vault |
| 530 | User Primary API |
| 531 | User Secondary API |
| 551 | User A |
| 552 | User A API |
| 553 | New User |
| 554 | New User API |
| 555 | User B |
| 556 | User B API |
| 610 | Emergency Room HCP |
| 612 | Emergency Room HCP HER |
| 620 | Registry |
| 701 | Encryption-Only Outsider API |
| 702 | Encryption-Only Outsider |
| 703 | Quarantine Location |
| 712 | Old Key Master |
| 714 | New Key Master |
| 812 | Onboard Key Master |
| 830 | Onboard Cloud Lockbox |
| 832 | Acceptable Sources |
| 834 | Acceptable Commands and States |
| 810 | Owner's Mobile Admin API |
| 851 | Owner |
| 860 | Manufacturer Subsystem |
| 861 | Manufacturer API |
| 862 | Onboard Manufacturer API |
| 870 | $3^{rd}$ Party Subsystem |
| 871 | $3^{rd}$ Party Provider API |
| 872 | Onboard $3^{rd}$ Party API |
| 910A-910E | HCPs |
| 920A-920C | HIE Registries |
| 1010 | HCP #1 |
| 1011 | HCP #2 |
| 1048 | Deposit-Only Member(s) |
| 1030A | Cloud Lockbox #1 |
| 1030B | Cloud Lockbox #2 |

DETAILED DESCRIPTION

This present application describes systems, devices and methods for conducting secure exchange of encrypted data using a three-element-core mechanism consisting of the key masters, the registries and the cloud lockboxes with the core mechanism integrating with any of numerous applications and administrative functions using application programming interfaces. A variation of the mechanism provides real-time protection for intelligent embedded systems such as those described as the Internet of Things.

This three-element-core and related application programming interfaces allow the mechanism to securely share the private keys of individuals among select key masters while keeping the private keys of all key masters only within the devices. This approach expands the uses for asymmetric encryption and creates a user-friendly multipoint solution. The distributed control of keys and encryption functions simplifies the user experience and enables features including private key revocation. Tightly coupling the three core elements of the mechanism mitigates the risk of sharing the private keys as access to the encrypted files remains controlled outside access to the keys. Managing the encryption keys separately from the encrypted information limits access to underlying information to only those: who are authorized through integrated identity management in the registry and verification in the cloud lockbox to access the encrypted files; and with whom the relevant private keys have been shared.

One with ordinary skill in the art will recognize that the mechanism may be configured in a variety of ways while retaining the primary characteristics, capabilities and benefits of the overall design. The present application provides in-depth explanation of some of the variations, but the presented variations are not meant to be exhaustive but rather provide examples.

General characteristics of the mechanism and the components of the mechanism follow.

A member may be an individual directly participating in a community of interest, an organization participating in a community of interest for its own purposes, or an organization participating in a community of interest to represent multiple individuals in which case the individual is participating by proxy.

A variation of the mechanism may add a case-based orientation to the individual-based orientation of the mechanism.

The key master software (preferably provisioned as a appliances) to:
  Generate individual public-private key pairs for itself, each individual being served by the key master, the organization (if applicable) and the case (if applicable);
  Receive an individual's data and related metadata from the application programming interface;
  Encrypt the data with the individual's public key;
  In some uses, encrypt some or all of the metadata with public key of individual or of metadata-only recipient;
  Transfer non-sensitive transactional metadata appended to the file and/or create non-sensitive transactional metadata and append to the file.
  Transmit the encrypted data and encrypted metadata to cloud lockbox, a process that may involve a secure relay;
  Control of the individual's private key (required for decryption) retained by the member's key master;
  Retrieve encrypted files from cloud lockbox, a process that may involve a secure relay, and decrypt with an individual's private key;
  With authorization by the individual or the individual's proxy:
    Securely transmit, either directly or through a secure relay, an individual's private key to another member's key master to permit decryption of the individual's files by another member's key master;
    Update permissions lists at registries to control access to files in cloud lockboxes;
    Transmit activity records to registry of key creation, file retrieval requests, private key exchanges and other activities;

The registries:
  Establish the identity and verify authenticity of individuals, members, organizations, other registries, cloud lockboxes and key masters;
  Establish unique identities for each individual represented in a community of interest, a process which may include:
    Communications with additional registries if more than one registry operational for the community of interest;
    Multi-step, multi-factor identity verification including biometrics, a process that may include use of mobile smart phones or similar devices;
    Use of an application programming interface;
    An in-person identification step;
  Maintain directories of individuals, members, organizations, cloud lockboxes, key masters and other registries;
  Function as a clearinghouse for members to retrieve public keys of other individuals, members, devices, organizations and cloud lockboxes;
  Manage individual-level, group level, file-level and file group-level access control lists for controlling access to data files;
  Receive activity records from the key masters, the cloud lockboxes and the application programming interfaces in order to;
    Provide activity list to individual members;
    Analyze activity logs to detect and halt anomalous access;
    Provide the members with alerts regarding anomalous access and with routine access to activity logs;

The cloud lockboxes:
  Store encrypted data;
  Operate as adapted on any file system in one or more physical locations;
  In some variations of the mechanism
    Generate unique file identification numbers;
    Control access to retrieve files;
    Control access to deposit files.

The related application programming interfaces offer flexibility in adapting to the needs of the specific community of interest and/or of the application owner.

The application programming interfaces:
  Consist of both publically published and private proprietary methods to integrate to the applications being used by members of a community of interest;
  Support multiple levels of application integration ranging from native integration, in which this mechanism's encryption and protocols are extended into the data stores of the application, to the use of industry-standard interfaces, and to simple archiving solutions and many gradations in between;
  May support a standalone service such as a file sharing interface on a desktop computer;
  Convert data to/from proprietary to industry standard formats;
  Convert data between key-value data stores to/from relational databases;
  Generate metadata specific to the application that can either be:
    Appended to the data and encrypted;
    Encrypted separately from the data so a member could be granted metadata only access;
    Left unencrypted and added to the transactional metadata created by key master;
  Map individuals' identification numbers in applications to community of interest identification numbers for the same individuals;
  Enable the creation of hybrid cloud and on-premise storage solutions;
  Transmit log records of file retrieval requests, access revocations and other activities to the registries;
  De-identify sensitive aspects user data and create tokens for substitution in transactional data and databases.

Support user registration and activation and management of key masters;

Operate key vaults for backup and restoration of private keys;

Create interfaces for tokenization and de-identification to mask sensitive or personally identifiable information.

Digital signatures may be used to verify the identity of members, registries, cloud lockboxes and key masters for communications and feature protocols. Encryption protects all sensitive data both in motion and at rest. Optional IP address restrictions add another level to the security model.

Any community of interest can establish its own operating parameters including:

Selecting a public key encryption algorithm;

Selecting a registry or registries;

Establishing related membership requirements and identity verification thresholds;

Selecting a cloud storage provider or providers at which to establish Cloud Lockboxes;

Selecting from among the optional security measures;

Determining the minimum application integration levels.

The method also provides protocols and metadata to enable features such as:

Time-to-live settings to limit the duration of a member's access to the data of an individual's data;

Key change and file access revocation processes;

Key and file recovery processes;

Tokenization to replace sensitive or personally identifiable information in transactional data and databases;

Ability to de-identify the individual's files to facilitate academic or business research.

Emergency access.

Key vault for backup and restoration of private keys.

The design supports addition of features by leveraging existing design elements and expanding operating protocols and related metadata.

The method minimizes the exposure of data to system administrators because:

The protected data is encrypted prior to reaching the registry or cloud lockbox;

The cloud lockbox has access to the encrypted files but never has the decryption key nor knows the identity of the files' owners;

The registry never has access to the decryption keys nor persistent access to the encrypted files;

Thus the system administrators performing duties for performance optimization and maintenance of the cloud lockboxes and registries cannot decrypt the data;

The method can be deployed in various ways to achieve the security level desired by the community of interest ranging from:

The stringent Federal Information Processing Standards 140-2 Level 4;

Rigorous civilian standards for protecting confidentiality such as Health Information Portability and Accountability Act;

The relatively low level security required for non-sensitive information:

And many levels in between.

The design traverses these various security levels based on:

Deploying the key master as an appliances thus keeping critical processes such as key management, encryption and decryption within a hardened environment rather than running this software on a general purpose computer;

Depth of integration with the applications;

Depth of identity verification applied;

Use of multi-factor authentication including potential biometrics, a process which may include use of mobile smart phones or similar devices;

Optional registered IP address restrictions.

The method provides a solution to integrate disparate applications within a single enterprise or across multiple enterprises by converting data in the application programming interfaces to either industry standard representations or proprietary common formats.

The design supports an approach for storing unstructured data in a key-value (object) data stores to simplify sharing and reduce the need for a relational database, yet retain the ability to transfer such information to/from relational databases.

The design supports the ability for the individual to review the contents and audit activity on his/her files.

The design provides the capability to provide a holistic view of the individual's files for individual or authorized member.

The design supports existence of multiple registries, multiple cloud lockboxes and distributed cloud lockboxes in which a single member's files are stored in multiple physical storage locations or types;

The design supports use of multiple encryption algorithms simultaneously from a single key master for participation in multiple community-of-interest networks.

The systems, devices and methods of the present application are well suited to operate in any industry requiring secure storage and exchange of information. The present application will describe an exemplary embodiment in the health care industry. Of course, one of ordinary skill in the art will appreciate that the systems, devices and methods of the present application have applicability in other industries, such as the legal service industry and the real estate industry, for example.

Recently, the storage requirements with respect to patient files and the Federal mandates to share records with other health care providers and with patients have presented daunting problems for those in the health care industry. The exemplary systems and methods described herein, generally referred to as a unified health exchange ("UHE"), may be used to solve many of the problems created by the increased storage and usage demands in the industry. The operation of the overall mechanism of the UHE will be described with particular applicability to the health care industry. In the health care application of the design consider the correspondence in the following Table I.

TABLE I

| Generalized | | Health Care Specific |
|---|---|---|
| System and Method for Securely Storing and Sharing Information | = | Unified Health Exchange |
| Registry | = | Health Information Exchange (HIE) Registry |
| Member | = | Health Care Provider, Pharmacy, Payer, Patient, etc. |
| Individual | = | Patient |
| Individual's Proxy | = | Health Care Provider serving as Patient's "Medical Home" |

Problems in the Health Care Industry

The UHE described herein solves critical and previously intractable challenges in the health care industry while simultaneously providing efficient use of resources and generating cost-savings. Health care providers ("HCPs") face mounting expenses and downward pressure on reimbursements. Federal mandates require layers of expensive technology that increase the cost of doing business.

Increased Storage Demands

Storage demands for electronic health records ("EHR") continue to expand rapidly, driven by factors including high resolution imaging data, genomics, wide variety of unstructured data, longitudinal care needs and regulatory retention requirements. The combination of increased demand and high cost storage results in rapidly growing IT costs for the HCPs.

Cloud services can dramatically reduce this cost, but cloud providers have been wary of the liability of storing health care records. HCPs have been concerned about the security of their data stored in cloud services. The Unified Health Exchange solution encrypts records prior to moving them to the cloud lockboxes and the cloud lockboxes and underlying cloud providers never possess the decryption key. This combination eliminates the need for the cloud providers to conduct breach notifications, greatly diminishing their HIPAA exposure.

By relying on the cloud lockboxes for long-term record retention, the HCPs can dramatically reduce the volume and thus the cost for on-premise computer storage. By leveraging intelligent archiving, the HCPs may elect to retain on-site only the records needed in the short-term. With deployment of a UHE appliance providing predictive caching, the HCPs could eliminate storage of patient files in their EHRs instead linking the underlying EHR file management to the UHE model. Further, the UHE approach can eliminate duplication of records within a single HCP as well as the duplication of records received from other health care providers.

Financially Sustainable HIE

Existing models for health information exchange involve cumbersome hierarchies of regional, state and national exchanges that have failed to gain traction. The financial models underpinning most HIE's do not offer a sustainable path, primarily because the current HIEs add incremental costs for HCPs at a time of great budget pressure. Health Care Providers are under increasing deadline pressure to achieve "meaningful use" of health information exchanges.

The Unified Health Exchange design enables HIE by default as a byproduct of the cost-saving storage arrangement with the cloud lockbox combined with the coordination functions of the HIE Registry. Thus the HCP saves money on storage and avoids the cost of supporting a separate HIE infrastructure.

Support for the Medical Home

The emerging "medical home" concept offers tremendous promise for coordination of care to improve wellness and reduce costs. The lack of health information exchange continues to hamper implementation of the "medical home" and other innovations such as accountable care organizations (ACOs). Unified Health Exchange consolidates patient records, offering the "medical home" a holistic picture of the patient. A "patient dashboard" may provide an easy overview of the patient's medical history and quick review of recent activity and condition.

Providers and payers struggle to identify fraud, waste and abuse. The disparate sources of information make compiling a complete view of a patient's care difficult. Once widely adopted, Unified Health Exchange can provide a single source of information for a comprehensive utilization review.

Personal health records ("PHR") have been envisioned as a key technology enabling patient education and involvement. Unfortunately, early PHR efforts have failed to:

Win support from health care providers.

Gain the trust of wary consumers over privacy concerns.

The Unified Health Exchange gives patients and/or their "medical home" unprecedented control over their medical records. Because the records are encrypted with individual keys, no one can decrypt the records until authorized for that specific individual.

Computer savvy consumers are able to directly authorize an HCP to access records and also exercise the granularity to only provide permission for specific classes of information. For instance, a podiatrist may not be allowed access to a patient's cardiac records. With Unified Health Exchange, the patient decides who sees what. Further, an audit log of access gives the patient complete visibility regarding who has accessed what and when.

For patients unable or not interested in controlling their own health records, the patient's "medical home" can serve as the patient's proxy by obtaining written sign-off similar to existing HIPAA forms to manage the access on behalf of the client.

The HIPAA and HITECH rules regarding the privacy of health records have created confusion and additional costs across the US health care industry. Unified Health Exchange reduces HIPAA responsibility for cloud lockboxes by encrypting the records. For HCPs, the more of their data they move to UHE the less vulnerability they retain.

For the EHR vendors, each of the many HIEs utilize unique interfaces to their software. UHE offers a single interface through industry standard methods to connect to what could serve as a global HIE platform.

UHE Operating Environment

This application now embarks on a detailed explanation of one particular implementation of the mechanism, focused on healthcare. One of ordinary skill in the art will recognize that the detailed example provides one of many ways to implement the mechanism.

Referring now to FIG. 1, there is illustrated an example operating environment 100 of the UHE. Example environment 100 may comprise a medical home HCP 101, an EHR system 110, a patient portal 114, a Key Master 112, an HIE Registry 120, a Cloud Lockbox 130, and various HCPs 144-148. As illustrated, a unified health exchange application programming interface, UHE API 261, and a Key Master 112 may be integrated with medical home's HCP #1 EHR 110 to facilitate communication with HIE Registry 120.

Further, a patient 116 may communicate with Medical Home's EHR 110 via patient portal 114. In addition, the Patient Portal 114 could utilized mobile interfaces to provide convenient interface to the Patient 116 via web or mobile app.

In a typical operation, medical home's HCP #1 EHR 110 using the UHE API 261 and the Key Master 112 assigns a unique public-private key pair and registers patient 116 with HIE Registry 120. The public key is provided to HIE Registry 120, and the private key is retained by medical home 101 in the Key Master 112 as the only entity initially authorized to decrypt patient files. This activity is depicted by reference numeral 1.

The HIE Registry 120 updates permissions directory at Cloud Lockbox 130 to authorize medical home's HCP #1 EHR 110 to write files for patient 114. This activity is depicted by reference numeral 2.

Medical Home's HCP #1 EHR 110 using the UHE API 261 and the Key Master 112 writes patient files encrypted with the public key to the Cloud Lockbox 130, retaining onsite only what is needed in the short term. HCP 110 using the UHE API 261 and the Key Master 112 can retrieve files as needed for longitudinal patient care scenarios. Medical Home HCP 110 using the UHE API 261 and the Key Master 112 can also access, retrieve and decrypt files written for patient 116 by other participating entities, such as HCPs 142-148. This activity is depicted by reference numeral 3.

Patient 116 authorizes Other HCP 141 to access files as depicted by reference numeral 4. Medical home HCP 110 using the UHE API 261 and the Key Master 112 updates permissions in HIE Registry 120 as depicted by reference numeral 1. HIE Registry 120 updates permissions at Cloud Lockbox 130 in routine synchronization process as depicted by reference numeral 2. Patient 116 can also audit access to his/her files as depicted by reference numeral 4.

Medical home's HCP #1 EHR 110 using the UHE API 261 and the Key Master 112 sends private key of patient 116 directly to Other HCP's EHR 143 using Other HCP's 141 Key Master 112 and the UHE API 261. This exchange of private key is conducted via encrypted transmission verified with digital signatures using the respective organizations public/private key pairs. The key exchange bypasses both the HIE Registry 120 and the Cloud Lockbox 130. This activity is depicted by reference numeral 5.

Other HCP's EHR 143 can now retrieve, decrypt and read files for the specific patient 116 using the patient's unique public/private key combination. Other HCP's EHR 143 can now also write files for patient 116 to same Cloud Lockbox 130 encrypted using the patient's public key. These activities are depicted by reference numeral 6.

Participation by pharmacies 144, depicted by reference numeral 7, add a useful function for coordination of medication regimens.

Other entities such as labs and patient telemetry providers 146 can write files encrypted with the patient's public key, but cannot retrieve or decrypt files. This reduces HIPAA liability for these entities, and such activities are depicted by reference numeral 8.

Patient-authorized payers 148 are provided limited access to patient files. For example, payers 148 may to review metadata but not detailed file information. Further, patient-authorized payers 148 and patient's health care providers could exchange and process claims forms as a particular class of data. This activity is depicted by reference numeral 9.

Further, patients' medical homes HCP #1 EHR 110 may securely contribute records to de-identified research databases 118, as depicted by reference numeral 10.

The exemplary system 100 provides a number of useful features including:

- Neither Cloud Lockbox 130 nor HIE Registry 120 ever have decryption keys, reducing HIPAA liability for these entities.
- HCPs 101, 141, 144, 146 and 148 save resources through intelligent archiving, enabling them to retain only the files needed in the short term in expensive on-premise storage.
- Reductions in record duplication within and between HCP EHRs 110, 143 and related software 145, 147 and 149 also saves resources.
- Design supports multiple cloud lockboxes 130, the split of a member's records across multiple storage types and locations, and multiple HIE Registries 120.
- Design supports a "glass break" scenario for emergency access to patient files.
- Design support key change process, key recovery process, file recovery process, waste/fraud/abuse detection, use of multiple encryption algorithms, and other features.

Unified Health Exchange Components

Referring now to FIG. 2, there is illustrated a schematic block diagram further depicting operation of the UHE of FIG. 1. Each HCP accessing the storage of Cloud Lockbox 130 may comprise or access an HIE Registry 120. In the illustrated example, medical home's HCP #1 EHR 110 utilizes UHE API 261 and Key Master 112 and secondary HCP #2 142 utilizes UHE API 261 and Key Master 112. The HIE Registry 120 provides the mechanisms and trust relationships for verifying unique identities, creating and updating patient-to-HCP and patient-to-cloud lockbox associations, and modifying permissions tables. Each HCP communicates with its associated HIE Registry 120 for patient identity matching to minimize duplication. Each HIE Registry 120 also retains mappings of public keys for patients, HCPs, payers and any other entities involved in UHE. Each HIE Registry 120 also catalogs authorized IP addresses for participating components for all participants.

Although a single Cloud Lockbox 130 is depicted in the example embodiment, it should be clear to those of ordinary skill in the art that multiple cloud lockboxes and/or multiple cloud storage servers may be employed. The cloud lockboxes, such as Cloud Lockbox 130, offer low cost yet responsive storage for the HCPs Encrypted EHR files 210, which may include file metadata used for the indexing, searching and features. The cloud lockboxes also retain a Permissions Directory 212 derived from the HIE Registry 120 for determining the mapping of which HCPs can read files for specific patients.

Each the UHE API 261 comprises software integrated with the HCPs' Electronic Health Record ("EHR") system. The UHE API 261 communicates with the API Engine 260 in the Key Master 112. In turn, the API Engine 260 communicates with the Key Manager and File Broker 262, also a component of the Key Master 112. The API Engine 260 provides a variety of interface options and policy enforcement function. Together these software modules cooperate with the HCP EHRs for issuing and/or managing patient public-private key combinations, interacting with the HIE registries and for reading/writing of files to the cloud lockbox(s). Each Key Master 112 also manages private key exchanges with the Key Masters 112 of other HCPs.

The UHE API 261 and the API Engine 260 may also convert proprietary data formats into standards-based formats. Likewise, when reading files from the cloud storage, the key master would convert standardized formats into proprietary formats for local EHR use.

It should be appreciated that the Key Master 112 can be implemented as hardware, software, or a combination of both hardware and software. For example, the Key Master 112 can be implemented, preferably, as a standalone appliance that can be inserted and integrated into an existing system architecture. In another example, the Key Master 112 can be implemented or installed onto a computer or other hardware identified and configured by a user. Such a computer may be a dedicated computer, for example, or may share resources between two or more applications or computing processes. A computer may be a suitable computing device having memory and a processor, and capable of storing program instructions in memory and executing the program instructions stored in memory using the processor.

Public Key Enervation and Digital Signatures

In a proxy operation of the design, the patient 116 selects one HCP, HCP 101 in the illustrated embodiment, to serve as his/her "medical home." This medical home HCP #1 EHR 110 using UHE API 261 and Key Master 112 generates a unique pair of encryption keys using a public-private key combination for the patient. The public key is shared with the HCP #1 EHR 110 but the private key is retained only in the Key Manager and File Broker 262 component of the Key Master 112. This activity is depicted by reference numeral 2.

The "public key" would not actually be shared with the general public, but rather it would be shared among HCPs participating in the HIE for file encryption.

The private key, retained by the medical home's Key Master 112, would be used to decrypt the data. The Cloud Lockbox would not have the ability to decrypt the files. Only the Key Masters 112 of HCPs authorized by the patient would receive the patient's private key, Each Key Master 112 also generates its own public-private keys utilized for secure communications and digital signatures but never shares its own device private key.

All communications and updates among entities may be secured through digital signatures and encryption including exchanges between Cloud Lockbox 130 and HIE Registry 120, exchanges between Cloud Lockbox 130 and Key Master 112, between Key Masters 112 of different HCPs, between UHE API 261 and API Engine 260.

IP Address Restrictions

In one example, within a given HCP, communications among components of the UHE and EHRs are restricted to known machine IP addresses to further increase security. Between HCPs, cloud lockboxes, and HIE registries, all communications may also be restricted to know machine IP address to further increase security. In particular, an accepted IP addresses list is maintained by the HIE Registry 120 and distributed along with public keys for these entities. When an individual patient elects to own and operate his/her own Key Master 112 as depicted in FIG. 18, IP restrictions may also be utilized to provide one method to control access.

Unified Health Exchange Operation

The flow of the following permissions and file accesses are depicted in FIGS. 1 and 2:

1. HCP EHR 110, the medical home EHR of patient 116, writes encrypted files to Cloud Lockbox 130 using UHE API 261 and Key Master 112. This includes the UHE API 261 converting the file into a UHE-compatible format and transmitting it to the APT Engine 260 in the Key Master 112. The file may include metadata such as, but not limited to, Patient's 116 unique identifier, type of file, and format of file (e.g. what type of reader might be required such as for PACS images). This activity is depicted by reference numeral 2.

2. The API Engine 260 transfers the file within the Key Master 112 to the Key Manager and File Broker 262. The Key Manager and File Broker 262 encrypts the patient's 116 file with patient's public key and transmits it to the Cloud Lockbox 130, thus already protected in motion. The files remains encrypted at rest on cloud server of Cloud Lockbox 130. This activity is depicted by reference numeral 3.

3. The Key Manager and File Broker 262 within the Key Master 112 is the sole location at the Patient's Medical Home 101 where the patient's 116 private key is maintained. Neither Cloud Lockbox 130 nor HIE Registry 120 nor HCP #1 EHR 110 have the patient's private key, thus cannot decrypt files, reducing HIPAA liability. HCP EHR #1 110 has the authority to retrieve and decrypt the Patient's 116 files, but in order to do so must process the request through the Key Master 112 in which the private keys are retained in the Key Manager and File Broker 262. Further the permission to read and write files for the Patient 116 was initially established in the HCP and Patient registration processes detailed in sections describing FIG. 3 and FIG. 4.

4. Upon receipt of Patient 116 file from HCP #1 110 by Cloud Lockbox 130, File Handler 211 creates a HCP #1 110 specific Receptor 214 for the file. The Receptor 214, encrypted with HCP #1's public key, includes a unique file ID, Patient's 116 public key, time-to-live settings (infinity for creator of file) and other metadata. The file ID is used by the File Handler 211 as a storage location pointer of the file in Encrypted EHR Files 210 store. The file ID will not provide a mapping to Patient 116 identity.

5. Creation by Cloud Lockbox 130 of Receptor 214 and writing of EHR File 210 is recorded in Activity Log 216 at the HIE Registry 120 for review by Patient 116 at will. This activity is depicted by reference numeral 5. FIG. 5 explains the operation of the activity logs in detail.

6. Patient 116 authorizes Medical Home's HCP #1 EHR 110 to release records to Secondary HCP #2 EHR 142. Authorization granted via e-signature using patient portal 114 or via signed paper form. The Patient 116 also has the option of granting access to metadata only. This activity is depicted by reference numeral 1.

7. The Patient 116 also has the option of setting a time-to-live for files retrieved by HCP #2 142. The time-to-live feature limits the period of time that HCP #2 is authorized to retain the Patient's 116 files. The time-to-live setting provides another layer of privacy protection that is included in the hierarchy of levels of integration of UHE into the EHR described later. Patient 116 may be made aware of compliance with time-to-live by HCP #2 142 or by HCP #1 110. Time-to-live settings for entities originating files will be set to infinity to enable use of UHE for archiving and for minimization or eventual elimination of local EHR files.

8. HCP #1 110 using UHE API 261 and Key Master 112 updates HIE Registry 120 with additional access rights of HCP 142 to read specific patient's files. Updates may be secured through digital signature based exchanges between HCP #1 110 and HIE Registry 120. Selections by patient 116 of level of access, i.e. metadata only vs. full file access, time-to-live settings and other variables, also transmitted to HIE Registry 120 by HCP #1 110. This activity is depicted by reference numeral 4.

9. HIE Registry 120 updates Permissions Directory 212 of Cloud Lockbox 130 granting access to Patient's 116 files to HCP #2 142. Selections by patient 116 of level of access, i.e. metadata only vs. full file access, time-to-live settings and other variables, also transmitted to Cloud Lockbox 130 by HIE Registry 120. This activity is depicted by reference numeral 5.

10. Cloud Lockbox 130 using File Handler 211 creates HCP #2 142 specific Receptor 214 for each file of Patient 116 to which HCP #2 has been granted access. The Receptor 214, encrypted with HCP #2's public key, includes a unique file ID, Patient's 116 public key, time-to-live settings and other metadata. The Receptor 214 includes whether the Patient 116 granted the HCP #2 142 full access or metadata only access to the file.

11. HCP #1 110 using UHE API 261 and Key Master 112 sends patient's private key encrypted using public key of HCP #2 142 to HCP #2's Key Master 112. The private key exchange process bypasses Cloud Lockbox 130 and HIE Registry 120, thus only HCPs possess private keys. This activity is depicted by reference numeral 6.
12. The transmission of the Patient's 116 private key is recorded to the Activity Log 111 for review by patient at will. Patient notification triggers would also be supported. This activity is depicted by reference numeral 4.
13. In some situations, the Patient 116 may only want the HCP #2 142 to have access to the metadata. In this case, a variation of the permission process would authorize access to the Receptors 214 but not share the Patient's private key.
14. HCP #2 EHR 142 can now write their own generated content to Cloud Lockbox 130 for the same patient 116. For files written by HCP #2 142, time-to-live settings are set to infinite. This activity is depicted by reference numeral 8.
15. HCP #2 EHR 142 can now retrieve existing patient files written by HCP #1 EHR 110. Using the UHE API 261 and the Key Master 112, HCP #2 EHR transmits a request, that may be digitally signed, for list of Receptors for Patient 116 identifying individual based on public key of Patient 116. Cloud Lockbox 130 responds with package of Receptors 214 for Patient 116 if authorization for access by HCP #2 142 is already in Permissions Directory 212. This activity is depicted by reference numeral 8.
16. HCP #2 EHR 142, using the UHE API 261 and the Key Master 112, decrypts the Receptors with its own private key. HCP #2 EHR 142 can then decide which files to download based on the Receptor metadata. HCP #2 EHR 140, using the file ID from the Receptor 214, requests the pertinent Encrypted EHR Files 210 for Patient 116. This activity is depicted by reference numeral 8.
17. Access by HCP #2 142 of Patient's 116 Receptors 214 and/or Encrypted EHR Files 210 for files written by any other entity, as well as instance of HCP #2 writing files to Cloud Lockbox 130 for Patient, are written to the Activity Log 216 at HIE Registry 120 for review by patient at will. Patient notification triggers would also be supported. This activity is depicted by reference numeral 5.
18. HCP #2 142 using UHE API 261 and Key Master 112 updates HIE Registry 120 with additional access rights of HCP #1 110 to read patient files written by HCP #2 142 for patient 116. This activity is depicted by reference numeral 7.
19. HIE Registry 120 updates permissions directory 212 of Cloud Lockbox 130, adding access for HCP #1 110 to files written by HCP #2 142 for Patient 116. Updates may be secured through digital signature based exchanges between Cloud Lockbox 130 and HIE Registry 120. This activity is depicted by reference numeral 5.
20. Cloud Lockbox 130 using File Handler 211 creates HCP #1 110 specific Receptor 214 for each file for Patient 116 to which HCP #1 has been granted access by HCP #2 EHR 142. The Receptor 214, encrypted with HCP #1's 110 public key, includes a unique file ID, Patient's 116 public key, time-to-live settings and other metadata.
21. HCP #1 EHR 110 also able to retrieve the files generated by HCP #2 EHR 142. This activity is depicted by reference numeral 3.
22. Access by HCP #1 EHR 110 of Patient's 116 Receptors 214 and/or EHR File 210 for files written by any other entity are written to the Activity Log 216 at HIE Registry 120 for review by patient at will. Patient notification triggers would also be supported. This activity is depicted by reference numeral 5.

Encryption Algorithm Flexibility

The UHE environment 100 described herein is designed to protect the privacy and confidentiality of electronic health records and other forms of sensitive information while also allowing such information to be securely shared with others. As such, the UHE environment 100 does not include a central key authority governing the UHE encryption. Rather, each independent Key Master 112 operates a Key Manager and File Broker 262 that generates public-private key pairs and retains the private keys.

Given the modularity and isolation of key creation, encryption, and decryption within the Key Manager and File Broker 262, a given community-of-interest electing to use the UHE mechanism could elect to use any suitable public key encryption algorithm of its choosing without impacting the operation of the UHE environment. For example, a first key master may operate a key master and file broker using a first public key encryption algorithm while a second key master may operate a key master and file broker using a second and different public key encryption algorithm.

In one example, as illustrated in FIG. 18, a Key Master 112 may operate multiple Key Manager and File Broker 262 modules in order to participate in multiple community-of-interest networks utilizing different encryption algorithms.

Details of the HIE Registry

Listed below are examples of the types of information which may be maintained by HIE Registry 120. Of course, the examples listed below are not meant to be exhaustive or prescriptive, but rather merely examples of the ways in which the underlying mechanism may operate.

TABLE B

| HCP Listings |
| --- |
| HCP Listings |
| Name of HCP |
| Type of HCP |
| Public Key of HCP |
| Date Registered |
| Authorization Method |
| Cloud Lockbox |
| IP Addresses |

TABLE C

| HCP Types |
| --- |
| HCP Types |
| Medical Center/Hospital |
| Outpatient Clinic |
| Physician Practice |
| Home Health/Hospice |
| Pharmacy |
| Health Department |
| Lab |
| Mobile/Home Telemetry |

TABLE D

Patient Listings
Patient Listings

Public Key of Patient
Public Key of Medical Home
Date Registered
Authorization Method
Public Keys of HCPs Authorized to Read and/or Write Records
Key Demographic Information for Identity Matching
Payer(s)

TABLE E

Directory of Registries
Directory of Registries

HCP-Registry Associations
Public Keys of Other Registries
IP Addresses

The activity logs contain transactional information to monitor access to patient's files. These include the Activity Log UHE API 111, Activity Log File Broker 264 and Activity Log Cloud Lockbox 216. The activity logs provide an essential cross check of file access for security purposes and also provide a rich source of information to inform the patient regarding access to and sharing of the EHR files, private key, etc.

The Cloud Lockbox

Listed below are examples of the types of information that may be stored by the Cloud Lockbox 130. The list is not meant to be exhaustive or prescriptive, but rather an example of one way in which the underlying mechanism may operate.

Encrypted EHR Files 210 may comprise unstructured key-value data store.

Metadata which may be used as key for granular permissions, searching and batch retrievals may include, but is not limited to:
Patient's Unique Identifier
HCP's Unique Identifier
Date of Activity
File Type
Registry Unique Identifier Such metadata and related functions could alternatively reside with the Registry.

HCPs may write encounter summaries to Cloud Lockbox 130 that include pertinent information such as date(s) of encounter, orders, vital signs, medications, history and physical, radiology report, physicians, discharge summary and links to image files also written to Cloud Lockbox 130. These files may adhere to industry standard formats such as HL7 and be in easily processed formats such as XML.

The Permissions Directory 212 of patients' public keys mapped to HCPs allowed to retrieve information provides an additional level of security to the mechanism beyond the data encryption. All HCP access may be verified via digital signature.

Receptors 214 are created for each file that an HCP is authorized to access. The Receptors 214 are encrypted with the specified HCPs public key. The Receptors include file ID, patient's public key, time-to-live settings, permissions settings, type of file, format of file (e.g. what type of reader might be required such as for PACS images) and other metadata.

File Handler 211 provides the mapping of file ID in the Receptor to the actual storage location of the file at the Cloud Lockbox 130. Thus the physical file location has been obfuscated, requiring the use of the File Handler 211 to retrieve files.

HCP Registration Process

Referring now to FIG. 3, there is a schematic block diagram illustrating an HCP registration process using the UHE of FIG. 1 and FIG. 2. An entity seeking to participate in the UHE network as a HCP Registrant 101-R may be registered as depicted in FIG. 3.

The HIE Registry 120 maintains database of HCPs, labs, telemetry providers, payers and any other entities that may have permission to read and/or write patient files (Registrant). As shown by reference numeral 1, HIE Registry 120 utilizes government sources and other trusted databases to assemble and verify entries in the HIE registry database. HIE Registry 120 may also generate its own public/private key combination for itself as a corporate entity.

As shown by reference numeral 2, a Registrant 101-R may verify its identity and authority with the HIE Registry 120 through multi-factor identity verification and may include exchange of authorized IP addresses.

Once verification is completed, the Registrant 101-R using HCP #1 EHR 110-R, UHE API 261 and Key Master 112 generates its own public/private key combination to identify itself as a corporate entity.

As shown by reference numeral 3, the Registrant 101-R transmits its public key to HIE Registry 120 which may be encrypted using the HIE Registry's 120 public key using the UHE API 261 and the Key Master 112. HIE Registry 120 decrypts as needed with own private key.

As shown by reference numeral 4, HIE Registry 120 replies with an acknowledgement that may be encrypted with its own private key. The Registrant 101-R verifies HIE Registry 120 transmission by decrypting with HIE registry's public key as needed using the UHE API 261 and the Key Master 112.

As shown by reference numeral 5, the Registrant completes registration with an acknowledgement to the HIE Registry 120 that may be encrypted with its own private key using the UHE API 261 and the Key Master 112. HIE Registry 120 verifies the registrant transmission by decrypting as needed with the registrant's public key.

Patient Registration Process

Referring now to FIG. 4, there is a schematic block diagram illustrating a patient registration process using the UHE of FIG. 1 and FIG. 2. Once an entity is registered, as described above, it can then serve as a "Patient's Medical Home" 101 for the patient and conduct the registration process as depicted in FIG. 4.

First, an HCP EHR #1 110 using UHE API 261 and Key Master 112 sends identifying patient demographic information to HIE Registry 120 as shown by reference numeral 1. The payload may be encrypted with the private key of the HCP, decrypted by the HIE Registry 120 with the HCP's public key, confirming the identity of the HCP.

Second, the HIE Registry 120 communicates to its network of HIE Registries if applicable, to verify uniqueness of patient 116 identity as shown by reference numeral 2.

Third, the HIE Registry 120 has three possible replies as shown by reference numeral 3:
  a. EXISTS: In registry, returns patient public key, medical home public key and cloud lockbox.
  b. NEW: Created listing, requests public key of patient.
  c. MORE: Indicating that additional information on patient required to determine whether unique identity.

In all three cases, the response may be encrypted with the HIE's private key for decryption by the HCP with the HIE registry's public key as needed, confirming identity of the HIE registry.

Fourth, the HCP replies as shown by reference numeral 4 depending on response in received in step 2:
  a. ACKNOWLEDGE: HCP acknowledges receipt and session terminates.
  b. REGISTER: HCP generates public/private key combination for patient. Transmits public key, ID of cloud lockbox and Payer(s) to HIE registry.
  c. Identity confirmation process continues.

In all three cases, the response may be encrypted with the HCP's private key for decryption by the HIE registry with the HCP's public key as needed, confirming identity of the HIE registry.

Fifth, the HIE Registry 120 replies as shown by reference numeral 5 depending on response received in step 3:
  a. Session completed in step 3.
  b. HIE registry acknowledges receipt and session terminates.
  c. Identity confirmation process continues.

In all three cases, the response may be encrypted with HIE's private key for decryption by the HCP with the HIE registry's public key as needed, confirming identity of the HIE registry.

Sixth, if the Patient 116 is a new patient to the HIE Registry network, then the HIE Registry 120 updates Cloud Lockbox 130 regarding registration of new Patient 116 as shown by reference numeral 6.

Seventh, the Patient's Medical Home 101 is now able to write and read files to the Cloud Lockbox 130 for Patient 116 using the HCP #1 EHR 110, the UHE API 261 and the Key Master 112.

Activity Logs Mechanism for Patient Information and for Detecting and Halting Unauthorized Access Referring now to FIG. 5, a schematic block diagram illustrates creating and comparing Activity Logs using the UHE of FIG. 2. Creation and comparison of Activity Logs are also supported by the example UHE environment.

An Activity Log UHE API 111, an Activity Log File Broker 264 and an Activity Log Cloud Lockbox 216 capture information representative of writing and reading of UHE files as well as information representative of changes to access by different members. For improved security, the Activity Logs are maintained at the HIE Registry 120 separate from the sources of Activity Log records. For example, Activity Logs may be maintained in a first data store while UHE files may be maintained in a second distinct data store. An Activity Logs Compare module 280 at the HIE Registry 120 provides a method for detecting and halting unauthorized access to files. The Activity Logs also provide a record of actions for review by the Patient 116.

Activity Log data may be obtained from one or more of a variety of sources. For example, when the UHE API 261 that is integrated with HCP #1 EHR 110 sends a file write or read request to the API Engine 260 in the Key Master 112 as depicted by reference numeral 1, the UHE API 261 simultaneously sends a report of the request to the Activity Log UHE API 111 at the HIE Registry 120 as depicted by reference numeral 2.

In one example, when the Key Manager and File Broker 262 in the Key Master 112 sends a file write or read request to the Cloud Lockbox 130 as depicted by reference numeral 3, the Key Manager and File Broker 262 simultaneously sends a report of the request to the Activity Log File Broker 264 at the HIE Registry 120 depicted by reference numeral 4.

In one example, when the File Handler 211 in the Cloud Lockbox 130 responds to a file write or read request depicted by reference numeral 3, the File Handler 211 simultaneously sends a report of the request to the Activity Log Cloud Lockbox 216 at the HIE Registry 120 depicted by reference numeral 5.

Periodically the HIE Registry 120 will analyze activity logs, using Activity Log Compare module 280, to detect anomalies that could indicate unauthorized access to Encrypted EHR Files 210 stored at the Cloud Lockbox 130 depicted by reference numeral 6. If such an anomaly is detected, then the HIE Registry 120 may alter the Permissions Directory 212 of the Cloud Lockbox 130 in order to halt file retrieval from the suspect Key Master 112 depicted by reference numeral 7. In one example, a Permission Directory 212 setting may indicate to the Key Manager and File Broker 262 the reason for the denial of file retrieval depicted by reference numeral 3. In one example, the HIE Registry 120 may also notify responsible members at the Participating HCP about the detected anomaly and denial of file retrieval. The notification may be performed via a suitable method established at the time of registration depicted by reference numeral 8. For example, a notification may include an email message, a text message, a telephone call, a pager alert, and so on.

Even in a proxy situation, the patient 116 could also receive notification of the anomalous access and the actions taken to halt such access.

In one example, the File Handler 211, Key Manager and File Broker 262, and the UHE API 261 may send periodic "heartbeat" messages to HIE Registry 120 to confirm ability to communicate. In such an example, the Activity Log Compare module 280 is able to detect the absence of heartbeat entries and generate a notification accordingly.

Inclusion of Deposit-Only-Members

Referring now to FIG. 6, there is a schematic block diagram illustrating sharing deposit-only data using the UHE of FIG. 1 and FIG. 2. Receiving and sharing lab results and home/mobile telemetry is also supported by the example UHE environment.

Certain providers in the health care field provide patient data without being allowed to receive patient data. Such providers, generally referred to generally as Deposit-Only-Members, may include participating vendors providing home or Mobile Health Monitor Software 146A, participating labs running Lab Software 146B and other participating entities with Deposit-Only Software 146C.

Like other HCPs, these Deposit-Only-Members may also associate to and register with an HIE Registry 120 in the UHE network by following the entity registration process described above in reference to FIG. 3.

By following a process similar to patient registration described in reference to FIG. 4, the deposit-only Mobile Health Monitor Software 146A, using the UPI API 261 and the Key Master 112, may retrieve a patient's public key and the ID of Cloud Lockbox 130 from the HIE Registry 120 as depicted by reference numeral 1. The Deposit-Only Participant 146A could then commence writing files encrypted with patient's public key to Cloud Lockbox 130 as depicted by reference numeral 1.

Only HCPs authorized by the patient would have the private key to decrypt the files written by Deposit-Only-Members. Deposit-Only-Members 146A, 146 B and 146 C would not possess any patients' private keys nor would such participants be authorized to retrieve files from the Cloud Lockbox 130.

The deposit-only mechanism could also be used to support person-to-person simplex exchange of encrypted data.

"Glass Break" Emergency Care Scenario

Referring now to FIG. 7, there is a schematic block diagram illustrating communications within the UHE environment in an emergency situation.

It is important for an HIE solution to provide emergency rooms with access to patient data in the event of an emergency that occurs outside of the patient's normal care community. The so-called "glass break" scenario outlined in the FIG. 7, shows how such functionality may work within the UHE framework.

1. Patient 116 presents to an emergency room 610, unable to provide authorization for access to his/her medical records depicted by reference numeral 1. The emergency room 610 is not one of the patient's normal HCPs.
2. Emergency room 610 using ER HCP EHR 612, UHE API 261 and Key Master 112 attempts to register patient 116 with HIE Registry 120 and, as a result, receives patient's medical home 101 public key and Cloud Lockbox 130 depicted by reference numeral 2.
3. Emergency room 610 sends request to HCP #1 EHR 110 for emergency-based release of private key using UHE API 261 and Key Master 112. Message to HCP 110 is encrypted with emergency room's private key. HCP 110 is able to decrypt message with emergency room's public key, verifying identity. Encrypted key exchange proceeds. These activities are depicted by reference numeral 3.
4. HCP 110 using UHE API 261 and Key Master 112 updates permission directory 220 at HIE Registry 120 allowing access to Patient's 116 EHR files 210 stored at Cloud Lockbox 130 for ER HCP EHR 612 depicted by reference numeral 4.
5. HIE Registry 120 updates permissions directory 220 at Cloud Lockbox 130 This activity is depicted by reference numeral 5.
6. Emergency room 610 using ER HCP EHR 612, UHE API 261 and Key Master 112 can now retrieve and decrypt patient files from Cloud Lockbox 130. Emergency room 610 also writes encounter summary and other files generated during encounter to the Cloud Lockbox 130 for later review by HCP 110. This activity is depicted by reference numeral 6.

If Emergency room 610 has not yet joined an applicable community of interest, then a similar mechanism would support emergency access to the records through the use of existing methods for sharing records such as the Direct Project or Blue Button.

Detecting and Preventing Waste, Fraud and Abuse

In addition to the coordination of care and HIE benefits of UHE, the mechanisms also support analytical methods to detect and prevent waste, fraud and abuse as illustrated in FIG. 8.

1. HCP 101, medical home of patient 116, using HCP #1 EHR 110, UHE API 261 and Key Master 112, generates a summary digest of all files written to Cloud Lockbox 130 and of all other HCP reads of files for its patients. Such a summary supports coordination of care, and triggers alerts to duplicated prescriptions, and redundant tests, among other things. Further, HCP EHR #1 110 provides data for patient review of activity on his/her health records. These activities are depicted by reference numeral 1.
2. Payer 148 also registers with HIE Registry 120 in a process similar to registration of HCPs depicted by reference numerals 2 and 3.
3. Payer 148, identified by HIE Registry 120 as Payer for the Patient 116, is able to review metadata for patients' files stored by Cloud Lockbox 130 by using UHE API 261 integrated with the Payer's Software 149 and Key Master 112. Payer 148 is not able to decrypt the contents without further authorization and related private key exchange. Thus payer 148 can identify some utilization trends with minimized HIPAA exposure. These activities are depicted by reference numeral 4.
4. Payer 148 and Patient's Medical Home 101 may collaborate to identify cases of waste, fraud and abuse depicted by reference numeral 5.
5. Insurance form submittals may also be written to Cloud Lockbox 130 by HCP #1 EHR 110, encrypted with the payer's public key, providing a simple mechanism for securely submitting and cataloging the reimbursement paperwork. The same document may also be written to the Cloud Lockbox 130 encrypted with the patient's public key. These activities are depicted by reference numeral 1.
6. Payer 148 using Payer's Software 149, UHE API 261 and Key Master 112 may retrieve reimbursement paperwork and write updates to such paperwork for review by Patient's Medical Home 101 as depicted by reference numeral 4.
7. Patient 116 is able to review all access to their files via patient portal 114 depicted by reference numeral 6.

Support for Medical Research

Using the UHE environment 100 described herein, one or more HCPs may elect to generate coordinated and longitudinal de-identified patient care research databases 118. Permission to extract such information may be solicited at the time the patient 116 is authenticated at his/her medical home 101. The coordinated care benefits would ripple into the research database, providing a complete picture of the individual's health history without any personal identifiers remaining. The communication mechanisms that support the generation of de-identified patient data is illustrated in FIG. 9.

Patient's medical home 101 using the HCP #1 EHR 110, UHE API 261 and Key Master 112 provides a full view of the medical status and activities of patient 116.

Files may be written to a de-identified patient database 118 with a "scramble" of the patient's unique identifier by using a De-Identification and Tokenization API 119;

This "scrambled" identifier used to replace patient identity information in file names, fields in files;

This "scrambled" identifier or the UHE unique patient identifier can also be used to replace patient identity information in fields in databases providing a tokenization function.

All identity and demographic information required to be removed from files and database records to achieve de-identification and/or tokenization can be saved in a patient demographics file encrypted in the patient's Cloud Lockbox 130.

The relationship of the new "scrambled" identifier to the actual patient unique identifier may be known only to the Patient's medical home 101.

Patient's Medical Home 101 may retain the mapping so that additional data for the patient can be added over time for longitudinal studies.

Key Revocation Process

Circumstances may arise in which the need for a Patient's 116 private key pair to be revoked from a Key Master 112. This need could arise from circumstances such as: decisions to revoke decryption authority previously granted to one or more HCPs; or decision of Patient 116 to switch to a different HCP as its medical home. Regardless of the reason the mechanism to change or revoke a key remains the same and is illustrated in FIG. 10.

Upon receiving a request to revoke a previously shared private key, HCP #1 EHR 110 using UHE API 261 and Key Master 112 updates HIE Registry 120 with the revocation request specifying the Key Master 112 of HCP #2 EHR 142 and the Patient 116 for whom key revocation is requested depicted by reference numeral 1. HIE Registry 120 will acknowledge change of state of Patient 112 in relation to HCP #2.

If Key Masters are in direct communications, then Key Master 112 of HCP #1 EHR 110 will send a revocation request directly to Key Master 112 of HCP #2 EHR 142 including the public key of the Patient 116 for whom the private key revocation is requested as depicted in reference numeral 5. Key Master 112 of HCP #2 EHR 142 will respond with acknowledgement of deletion of private key for Patient 112 of HCP #1 as depicted in reference numeral 5.

If Key Masters are not in direct communications, then Key Master 112 of HCP #2 EHR 142 will receive notification of request from Registry 120 during the next routine polling of Registry 120 by Key Master 112 of HCP #2 EHR 142 as depicted in reference numeral 7. Key Master 112 of HCP #2 HER 142 will respond with acknowledgement to HIE Registry 120 of deletion of private key for Patient 112 of HCP #1 as depicted in reference numeral 7. Key Master 112 of HCP #1 EHR 110 will receive confirmation of request to delete private key of Patient 116 of EHR #1 during the next routine polling of HIE Registry 112 as depicted in reference numeral 1.

Key Change Process

Circumstances may arise in which the need for a change of the Patient's 116 public-private key pair is required. This need could arise from circumstances such as: compromise of the privacy of the public-private key pair; switch to a new encryption algorithm, etc. Regardless of the reason the mechanism to change or revoke access remains the same and is illustrated in FIG. 10.

Upon receiving a request to change a key or revoke access, HCP #1 EHR 110 using UHE API 261 and Key Master 112 generates a new key pair and updates HIE Registry 120 with the change including both the old and new public keys of Patient 116 depicted by reference numeral 1.

HIE Registry 120 updates Permissions Directory 212 with the change and with an indication that key change process is about to commence for Patient 116 depicted by reference numeral 2.

Permissions Directory 212 and File Handler 211, both at Cloud Lockbox 130, prepare a new set of Receptors for Patient's 116 files.

Patient's Medical Home 101, using HCP #1 110, UHE API 261 and Key Master 112, then transmits the digitally signed request for the current and new list of Receptors 214 for Patient 116. HCP #1 EHR 142 identifies Patient 116 based on both the old and new public keys of Patient 116. Cloud Lockbox 130 responds with two packages of Receptors 214 for the Patient 116, both the old and the new, each encrypted with HCP #1's 110 public key. These activities are depicted by reference numeral 3.

HCP #1 110 using Key Master 112 retrieves all Encrypted EHR Files 210 for Patient 116, decrypts the files with the Patient's 116 old private key and re-encrypts the files with the Patient's 116 new public key. HCP #1 EHR 110, using UHE API 261 and Key Master 112, then writes Encrypted EHR Files 210 for Patient 116 back to Cloud Storage 130 as managed by the File Handler 211. These activities depicted by reference numeral 3.

HCP #1 EHR 110, using the UHE API 261 and Key Master 112, erases the old version of the Patient's 116 Encrypted EHR Files 210. However, the files written to Cloud Storage 130 by HCP #2 EHR 142, now designated at 210-A, the entity whose access is being revoked, are not erased. This measure is necessary so that HCP #2's internal operations are not compromised in terms of retaining patient files. These activities depicted by reference numeral 3.

Cloud Lockbox 130 records the activity in the Activity Log Cloud 216 maintained at HIE Registry 120 as depicted by reference numeral 2.

HCP #1 EHR 110, using UHE API 261 and Key Master 112, notifies other HCPs still authorized to write to Patient's files such as HCP #3 EHR 152 of the Patient's new public key depicted by reference numeral 4. HCP #1 EHR 110, using Key Master 112, also notifies other HCPs still authorized to read and decrypt Patient's files such as HCP #3 EHR 152 of the Patient's 116 new private key depicted by reference numeral 4.

In one example, HCP #2 142, using UHE API and Key Master 112, can continue to retrieve and decrypt the files it wrote to Patient's 116 record using the old private key now shown as HCP #2 Encrypted EHR Files 210-A. This measure allows HCP #2 EHR 142 to continue to use the Cloud Lockbox 130 for archival purposes of its own activity. However, HCP #2 EHR 142 will no longer be able to retrieve or learn of the existence of other Encrypted EHR Files 210 for the Patient 116. These activities depicted by reference numeral 6.

File Revocation Process

Reversing the process of sharing files may be used to revoke files, including the ability to request and confirm deletion of previously downloaded and decrypted files as illustrated in FIG. 10.

HCP #1 EHR 110, using UHE API 261 and Key Master 112, issues a file revocation request to the Key Master 112 of HCP #2 EHR 142 for all files that HCP #2 142 has downloaded for Patient 116 other than those file written by HCP #2 EHR 142 depicted by reference numeral 5.

If Key Masters are in direct communications, then Key Master 112 of HCP #1 EHR 110 will send a revocation request directly to Key Master 112 of HCP #2 EHR 142 including the public key of the Patient 116 for whom the private key revocation is requested as depicted in reference numeral 5. Key Master 112 of HCP #2 EHR 142 will respond with acknowledgement of deletion of files for Patient 112 of HCP #1 as depicted in reference numeral 5.

If Key Masters are not in direct communications, then Key Master 112 of HCP #2 EHR 142 will receive notification of request from Registry 120 during the next routine polling of Registry 120 by Key Master 112 of HCP #2 EHR 142 as depicted in reference numeral 7. Key Master 112 of HCP #2 HER 142 will respond with acknowledgement to HIE Registry 120 of deletion of private key for Patient 112 of HCP #1 as depicted in reference numeral 7. Key Master 112 of HCP #1 EHR 110 will receive confirmation of request to delete files of Patient 116 of EHR #1 during the next routine polling of HIE Registry 112 as depicted in reference numeral 1.

If HCP #2 EHR 142 software is compliant with this feature of UHE, then it can acknowledge using Key Master 112 the destruction of Patient's 116 Encrypted EHR Files 210 that it had downloaded but not created as depicted by reference numeral 5.

HCP #1 EHR 110, using UHE API 261 and Key Master 112, writes to Activity Log 216 maintained at the HIE Registry 120 the outcome of revocation requests and the notification of HCPs still authorized to write and/or read files depicted by reference numeral 1.

Key Recovery and/or File Recovery

The UHE environment 100 described herein is designed to protect the privacy and confidentiality of electronic health records and other forms of sensitive information while also allowing such information to be securely shared with others. As such, there is no central key authority governing the UHE design. Each Key Master 112 operates a Key Manager and File Broker 262 that generates public-private key pairs and retains the private keys. Thus a complete loss of the private key(s) would render the information protected inaccessible without massive computational effort to recover the private key. Only files remaining in local EHR storage would be recoverable directly from within UHE.

This aspect of potential loss of private keys of UHE is a privacy-enhancing design feature but does call out the importance of sharing the private keys with at least one other member with its Key Master 112 operating at sufficient physical distance to provide for disaster recovery scenarios. Alternatively, HCP #1 EHR 110 may install and register a second Key Master 112 that is automatically granted read and write access for any Patient 116 selecting HCP #1 as its Medical Home 101.

In the event that a Key Master 112 becomes damaged, corrupted or otherwise loses private keys under its control, the key recovery process would in most cases resolve the loss of private keys as illustrated in FIG. 11.

In the worst case scenario, the Patient's Medical Home 101 has suffered a corruption of the Key Master 112 such that the private key of one or more patients has been lost. Thus, the entire operation of the Key Master 112 may have failed.

First the Patient's Medical Home 101 rectifies operational problem affecting the Key Master 112 and re-establishes registration of the new software instance with the HIE Registry 120 as depicted by reference numeral 1.

The U-API 261 initiates through the Key Master 112 the key recovery process using the public key of affected patients.

The Key Master 112 then initiates the key recovery process with the HIE Registry 120. HIE Registry replies with a private key holder, e.g. HCP #2 EHR, for one or more patients based on the Patient Directory and Permissions 282. These activities are depicted by reference numeral 1.

The HIE Registry 120 sends to the Key Master 112 of HCP #2 EHR 142 a list of patients for whom HCP #1 EHR 110 needs private key recovery as depicted by reference numeral 2. Alternatively, if Patient's Medical Home 101 had installed and registered a second Key Master 112, the HIE Registry 120 initiates the key recovery process with this backup Key Master 112 first. The remainder of the process would remain as follows.

Key Master 112 of HCP #2 EHR 142 transmits private keys for patients in a list from HIE Registry 120 to the Key Master 112 of HCP #1 EHR 110 as depicted by reference numeral 3. This communication would be further secured by digital signatures and optionally IP address restrictions.

Key Masters 112 HCP EHR #2 142 records this activity in the Activity Log File Broker 264 as depicted by reference numeral 2.

The HIE Registry 120 then sends to the Key Masters 112 HCP #3 EHR 152 a list of patients for whom the Key Masters 112 of HCP #1 EHR 110 needs private key recovery as depicted by reference numeral 4.

Key Master 112 of HCP #3 EHR 152 transmits private keys for patients in a list from HIE Registry 120 to the Key Master 112 of HCP #1 EHR 110 as depicted by reference numeral 5. This communication would be further secured by digital signatures and optionally IP address restrictions.

Key Masters 112 HCP EHR #3 152 records this activity in the Activity Log File Broker 264 as depicted by reference numeral 4.

The described process repeats until Patient's Medical Home retrieves private keys for all affected patients.

Should the key for a patient 116 be unrecoverable, the Patient's Medical Home 101 may initiate a file recovery process that seeks to restore to the UHE network whatever EHR files for the Patient 116 remain in local storage of the HCP EHR participating in the care of the given Patient 116. The key change process from FIG. 10 and a modification of the key recovery process from FIG. 11 that focuses on files instead of keys are then invoked.

Multiple UHE APIs at a Participating HCP

A Participating HCP will in most cases operate multiple EHR software systems as well as other auxiliary systems requiring data feeds from EHR systems. These software systems are likely to include but not be limited to an inpatient EHR, I-EHR 110-A; an ambulatory EHR, A-EHR 110-B; and a picture archiving and communication system, PACS 110-C as illustrated in FIG. 12. These various systems often function independently within a health care organization, requiring internal integration to create a unified view of a given patient.

Each of the EHR software systems will need to run an interface to participate in UHE called the UHE API 261. However only a single Key Master 112 would be required, with the API Engine 260 able to communication with multiple UHE APIs 261.

In such a configuration, UHE can support internal HCP integration efforts by providing the common interface among all systems. For vendors of EHR systems, UHE presents a single interface to develop that would serve HCPs with any blend of EHR systems.

Multiple HIE Registries

While it would be simpler to have a single HIE registry to serve all patients, this outcome seems unlikely in our highly competitive health care and IT markets. One of ordinary skill in the art will recognize that the UHE described herein may be embodied in alternate configurations, including an environment having multiple HIE registries as illustrated by FIG. 13.

In such an embodiment, each HCP 910A-910E associates with only one HIE registry 920A-920C. The HIE registries 920A-920C communicate with each other during:
  Patient registration process to confirm uniqueness.
  Exchange of HCP registrations.
  Exchange of patient record permissions changes, e.g. new HCP authorized by patient.

Multiple Cloud Lockboxes

While it would be simpler to have a single provider of cloud lockboxes to serve all HCPs, one of ordinary skill in the art will recognize that such a configuration may not accommodate the highly competitive health care and IT markets. Thus, the UHE design accommodates the existence of multiple providers of cloud lockboxes as illustrated in FIGS. 14A and 14B.

Figures 14A, 14B:
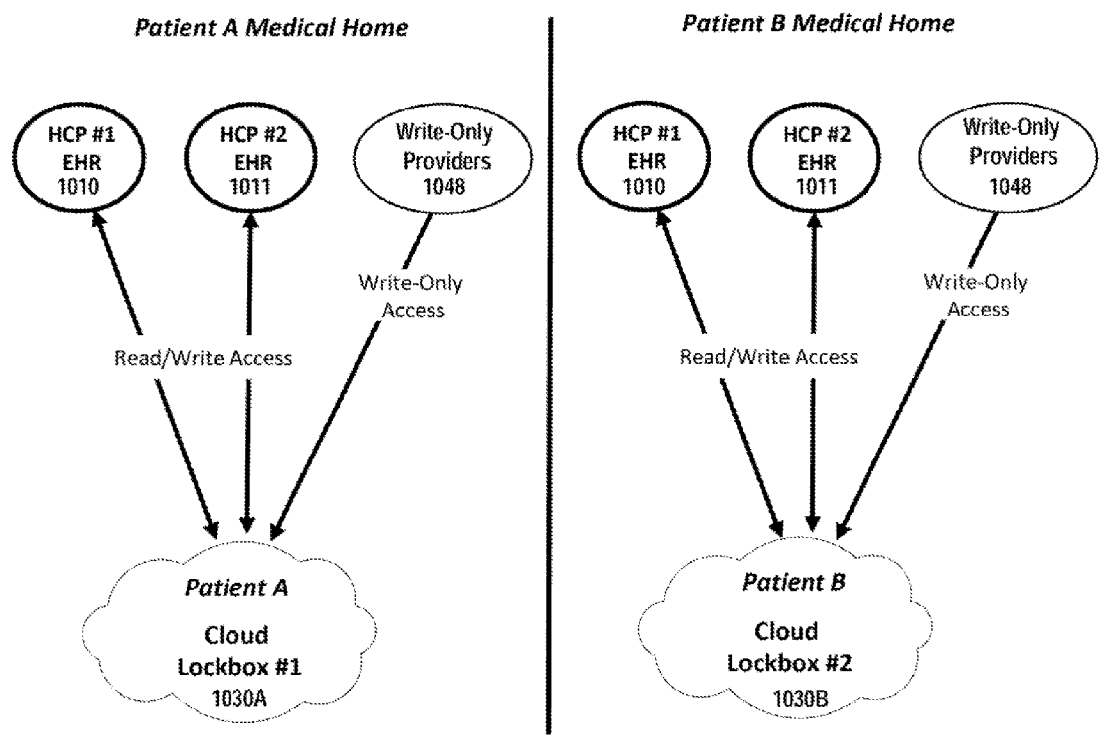
FIGS. 14A and 14B are a schematic block diagrams illustrating other alternate environments for the systems, devices and methods of the present application.

As illustrated in FIG. 14A, HCP 1010 is the medical home for patient A. HCP 1010 designates cloud lockbox 1030A for patient A. The association is identified during HIE registration of the patient. Patient A authorizes HCP 1011 to read/write files. HCP 1011 writes files for patient A to cloud lockbox 1030A to keep all patient files in one source. Similarly, deposit-only input for patient A, such as lab results from HCP 1048, are also written to cloud lockbox 1030A.

As illustrated in FIG. 14B, HCP 1011 is the medical home for patient B. HCP 1011 designates cloud lockbox 1030B for patient B. The association is identified during HIE registration of the patient. Patient B authorizes HCP 1010 to read/write files. HCP 1010 writes files for patient B to cloud lockbox 1030B to keep all patient files in one source. Similarly, deposit-only input for patient B, such as lab results from HCP 1048, are also written to cloud lockbox 1030B.

Split Cloud Lockboxes

While it would be simpler for a single provider of storage services to serve all the records for a given Patient 116, one of ordinary skill in the art will recognize that a Patient's 116 Cloud Lockbox 130 may be split across multiple storage services and multiple file systems by designating storage services in any of or a combination of the Receptors 214, and/or Registry's 120 Permissions Directory 212 or other aspects of the Registry 120.

The flexibility of the mechanism allows any file system to be integrated as a provider of storage services for Cloud Lockboxes 130.

Levels of Integration

It should be appreciated different levels of integration may be possible between EHRs and the UHE. For example, evolution and extension of the interfaces will progress over time. All levels of integration may be supported by a single API Engine 260 in the Key Master 112. An example delineation of the levels of integration is depicted in the following table.

TABLE 2

Levels of EHR Integration with UHE

| | |
|---|---|
| Level 1 | Method for backing up or archiving EHR files. |
| Level 2 | Engaged in a network of providers for health information exchange. |
| Level 3 | Honor incoming revocation requests. Honor time-to-live settings in meta data. |
| Level 4 | Retain full metadata in native EHR file storage. Provide identity of individual who accesses patient files for additional detail in activity logs. |
| Level 5 | Use of UHE with local caching as primary file store. |

Data Access Options

In some situations, it may not be necessary to access complete data records but rather to only access a partial record of a patient such as basic patient information. For example, an insurer may need to know that a certain diagnostic test was performed but the insurer does not need to have access to a full patient file. In another example, a physician specializing in one field such as podiatrist may not need to have access to patient information pertaining to another medical field such as the patient's records about a patient's heart condition. Thus, in one example, a partial data record such as metadata may be provided rather than the entire patient data file.

In some situations, it may be undesirable to provide data from which specific patient identities can be determined. For example, an organization performing research may be interested in patient outcomes in relation to a specific treatment of a disease. However, the organization performing the research may not be permitted to know the identities of the patients. Thus, in one example, patient data may be anonymized in order to eliminate information such as names, addresses, and social security numbers.

Patient Dashboard

In one example, the patient portal 114 may further provide patient 116 with a patient dashboard. In particular, the patient dashboard may provide an overview of the patient's 116 medical history as well as an overview of recent activity and medical conditions. Such a patient dashboard provides a single source of information from which a patient 116 may obtain a personal medical summary as well as a comprehensive medical review.

Alternative Business Models in Health Care

Given the flexibility of the described systems, devices and methods, the UHE business model could take other forms. FIG. 15 illustrates one such alternate embodiment. FIG. 15 depicts an environment similar to that of FIG. 1 except that an entity other than a health care provider may become a patient's medical home for the purposes of medical record aggregation, called a "Medical Home" Health Record Representative ("HRR").

The HCPs are or will soon be required by Federal mandate to be able to share patient records through a set of HIE standards. Thus, the HIE goals of UHE could be met even if the HCP did not directly participate in the UHE mechanism. Such an HCP would sacrifice the cost savings inherent in the UHE design in terms of reducing storage costs unless they transferred their long-term record retention responsibilities to the HRR.

The HRR could also operate a blended architecture offering a choice between the standards-based HIE-interface solutions and the full UHE implementation.

Other Industries

The systems, devices and methods of the present application have been described primarily in relation to an example health care system. The systems, devices and method are also applicable in a wide variety of other industries in which confidential information needs to be selectively and securely shared among multiple business entities.

Legal Industry

Referring now to FIG. 16, there is illustrated a schematic block diagram depicting a system supporting the legal industry, using a similar design as in FIG. 1 for the medical industry, but with different entities. Following the concept of the "medical home" this model addresses the creation of a "legal home" for the client. Such a "home" selection does not preclude the use of other lawyers, but the "home" lawyer does become the initial issuer and owner of the public/private key set. Similar to the health care industry, other business entities could provide the "legal home" other than law firms.

Other law firms, prosecutors and courts may be granted granular read-write access on a client-by-client basis. Deposit-Only participants such as court reporters and labs could securely write files to the client's case file without gaining the ability to retrieve and/or decrypt any other files related to the case. The client would have a complete view of all files related to his/her case and the ability to audit access.

Real Estate Industry

Referring now to FIG. 17, there is illustrated a schematic block diagram depicting a system supporting the real estate industry, using a similar design as in FIG. 1 for the medical industry, but with different entities. Once again following the concept of the "medical home" this model addresses the creation of a "real estate home" for the client. Such a "home" selection does not preclude the use of other realtors, but the "home" realtor does become the initial issuer and owner of the public/private key set. Similar to the health care industry, other business entities may provide the "real estate home" other than real estate firms.

Other realtors, mortgage brokers, lawyers, developers, etc. may be granted granular read-write access on a client-by-client basis. Deposit-Only participants such as appraisers and inspectors could securely write files to the client's file without gaining the ability to retrieve and/or decrypt any other files related to the business situation. The client may have a complete view of all files related to his/her business situation and the ability to audit access.

Information Owner Controlled

The preceding depictions of the system have assumed the presence of a proxy acting on the information owners request to manage the owner's information. However, as shown in FIG. 18, an example design also supports a standalone use of the mechanism operated by the owner to directly manage multiple types of information using a similar design as in FIG. 1. In this scenario there is no "medical home" or "legal home" with default access. Instead, the information owner originates the key-pairs and all permissions. In this scenario, all activities including registration, sharing of private keys, revocation requests and key pair changes would originate with the owner using his/her own Key Master 412.

The API Engine 460 could support multiple versions of APIs 461 for a variety of desktop and mobile applications running on any suitable operating system.

In one example, information owner may elect to run multiple Key Manager and File Broker modules 462 in the Key Master 412. In this way, the Information Owner can participate in multiple community-of-interest networks operating with different encryption algorithms. In this example, the Key Master 412 contains two Key Manager and File Brokers, 462-A and 462-B each operating a different encryption algorithm specific to the two specific communities-of-interest depicted. In particular, Key Manager and File Broker-A 462-A uses an encryption algorithm shared by all members of the community-of-interest participating in the health care network represented by Cloud Lockbox Health Care 430-A and HIE Registry 420-A. Key Manager and File Broker-B 462-B uses an encryption algorithm shared by all members of the community-of-interest participating in the legal network represented by Cloud Lockbox Legal 430-B and Legal Exchange Registry 420-B. Thus, a single Key Master 412 could support multiple Key Manager and File Broker 462 modules for participation in multiple community-of-interest networks.

Alternative Methods of Communications and Monitoring Using a Key Master "Phone Home" Operations One of ordinary skill in the art will recognize that the network environments hosting Key Masters 112 may make difficult inbound communications to the Key Masters 112. An alternative solution depicted in FIG. 19 illustrates the flexibility of the mechanism while maintaining the same level of security.

Key Masters 112 may maintain routine contact with Registry 620 in a type of polling process that both lets Registry 620 detect the status of Key Masters 112 as well as provide opportunities to transmit waiting files, keys, etc. to Key Masters 112 using the Registry 620 as a secure relay as depicted in reference numerals 2 and 3. This "phone home" feature of the Key Masters 112 avoids many of the complexities of the various network environments hosting Key Masters 112.

One of ordinary skill in the art will recognize that the secure relay function could be similarly facilitated by the Registry 620 even in the event that the secure relay utilizes some storage location other than the Registry 620.

The Key Masters 112 routine contact with the Registry 620 also enables optional security features, using the contact as a form of "heartbeat" for the Key Master 112. For instance, a Key Master 112 that goes offline for some set period of time may trigger the Registry 620 to disable that Key Master's 112 functions such as sharing keys and/or retrieving files until such time that the Key Master Admin 511 reactivates with the Registry 620 as depicted in reference numeral 4 of FIG. 21.

Similarly, a Key Master 112 that goes offline may, when appearing again online, report its IP address information and, if equipped with a GPS chip, report its physical location. These data points would provide additional information for the Registry 620 to act upon.

One of ordinary skill in the art will recognize numerous ways in which these "heartbeat," IP and location information about a Key Master 620 could be used to further improve the security of the mechanism.

Key Exchange Using Key Master "Phone Home" Feature

One of ordinary skill in the art will recognize that the "phone home" alternative method of communications may be used to facilitate key exchange in situations in which Key Masters 112 and/or the networks to which Key Masters 112 are connected, do not readily support direct Key Master 112-to-Key Master 112 communications. This approach also retains the benefit of the Registry 620 never knowing the decryption keys because the Registry 620 never has the respective operational Key Masters' 112 private keys required to decrypt the exchanged keys as illustrated in FIG. 19.

User A 551 using User A API 552 authorizes User B 555 to have access to some portion of User A's 551 files to which User B's 555 Key Master 112 does not currently have the private key required for decryption. Such authorization may require authentication, potentially multi-factor.

User A API 552 via its associated Key Master 112 updates permissions at Registry 620 for User B 555 access to all or a designated portion of User A's 551 files, and Registry 620 returns public key of User B's 555 Key Master 112 as depicted in reference numeral 2. Such authorization may require authentication, potentially multi-factor.

Registry 620 transmits public key of User B's 555 Key Master 112 to User A's 551 Key Master 112 as depicted in reference numeral 2.

User A's 551 Key Master 112 encrypts relevant private key of User A 551 with public key of User B's 555 Key Master 112 and transmits to Registry 620 as depicted in reference numeral 2.

Registry 620 provides to User B's 555 Key Master a one-time, optionally time-restricted, download link for relevant encrypted private key of User A 551 as depicted in reference numeral 3.

User B's 555 Key Master 112 downloads the encrypted private key of User A 551 which User B's 555 Key Master 112 decrypts with own private key and adds to foreign-key key chain for later use in decrypting retrieved files of User A 551 as depicted in reference numeral 3.

This process can also be reversed to provide a mechanism for User A's 551 Key Master 112 to request deletion of a previously shared private key of User A 551 in the event that User A 551 revokes access.

Identity of User A 551 and User B 555 may remain de-identified in Key Masters.

Process facilitates key exchange in situations in which Key Masters 112 and/or the networks to which Key Masters 112 are connected, do not readily support direct Key Master 112-to-Key Master 112 communications. As such, in this scenario Key Masters 112 will need to periodically poll the Registry 620 for updates regarding permission changes, key exchanges, etc.

This approach also retains the benefit of the Registry 620 never knowing the decryption keys because the Registry 620 will not have the respective Key Masters' 112 private keys required to decrypt the exchanged keys.

Alternative Process to Deposit Files

One of ordinary skill in the art will recognize that alternative approaches to depositing files from a Cloud Lockbox 130 as depicted in FIG. 20. This alternative approach retains all features and protections of the mechanism as well as simplifies the functions of the Cloud Lockbox 130, enabling easier integration of a wide variety of file systems and storage types. The following process envisions a user employing a desktop interface, but would be the same regardless of the API employed.

User A 551 adds file to a mechanism-designated desktop folder in User API 552.

User A API 552 transfers file to User A's 551 Key Master 112 along with mechanism-designated folder metadata that may include category of file, class of access provided, group permissions, group policies, etc. as depicted in reference numeral 1.

User A's 551 Key Master 112 encrypts file and transmits to Registry 620 along with folder and file metadata as depicted in reference numeral 2.

User A's 551 Key Master 112 returns to the User A API 552 a unique file identifier for use in retrieving file as depicted in reference numeral 1, the unique file identifier having no direct mapping to User A 551 or to the original name of the file.

Registry 620 updates file list for User A 551 and associated permissions to access file for other users based on rules associated with folder metadata and file metadata.

Registry 620 writes encrypted file to Cloud Lockbox 130 as depicted in reference numeral 3.

Alternative Process to Retrieve Files

One of ordinary skill in the art will recognize that alternative approaches to retrieving files from a Cloud Lockbox 130 as depicted in FIG. 20. This example of one alternative approach of several variations that retains all features and protections of the mechanism. This particular example also simplifies the functions of the Cloud Lockbox 130, enabling easier integration of a wide variety of file systems and storage types. The following process envisions a user employing a desktop interface, but would be the same regardless of the API employed.

User A 551 selects file to retrieve via User API 552.

User API 552 transmits to User A's 551 Key Master 112 the unique file identifier of requested file and identity and other required user credentials of User A 551 as depicted in reference numeral 1.

User A's 551 Key Master 112 transmits to Registry 620 the unique file identifier of requested file and identity of User A 551 as depicted in reference numeral 2.

If authorization of User A 551 to retrieve file confirmed by Registry 620, then Registry 620 transmits to Cloud Lockbox 130 the unique file identifier of requested file as depicted in reference numeral 3.

Cloud Lockbox 130 returns to Registry 620 a one-time, optionally time-limited, access token for download of requested file from Cloud Lockbox 130 as depicted in reference numeral 3.

Registry 620 returns to User A's 551 Key Master 112 the one-time access token to download file from Cloud Lockbox 130 as depicted in reference numeral 2.

User A's 551 Key Master 112 retrieves file from Cloud Lockbox 130 using one-time access token as depicted in reference numeral 4.

User A's 551 Key Master 112 decrypts file and provides to User A's 551 User API 552 as depicted in reference numeral 1.

Alternatively, as an additional feature of the User API 552, User A 551 may view and edit the file without the file leaving the Key Master 112.

Key Master Admin API and Adding a User to an Existing Key Master

Administration of Key Masters 112 can be aided by a Key Master Admin API 510, improving convenience and security of the mechanism as depicted in FIG. 21.

New User 553 using New User API 554 establishes identity with Registry 620 which may include various forms of identity verification and may include multi-factor authentication as depicted in reference numeral 1.

New User 553 using New User API 554 requests key creation and services from an existing Key Master 112 including submission of credentials established with Registry 620 and may include multi-factor authentication as depicted in reference numeral 2.

Existing Key Master 112 and New User API 554 identify one another using unique Key Master serial number and/or other unique identifiers as depicted in reference numeral 2.

Existing Key Master 112 communicates to Registry 620 the credentials of the New User 553 and New User API 554 requesting services from existing Key Master 112 as depicted in reference numeral 3.

New User API 554 transmits Key Master's 112 serial number and/or other unique identifiers to Registry 620 along with credentials of New User 553 as depicted in reference numeral 1.

Registry 620 confirms match of information coming from New User API 554 and existing Key Master 112 regarding New User 553 as well as New User API 554. The Registry 620 may also gather additional information such as IP address of New User's API 554 to aid in detection of anomalous behavior.

If Registry 620 detects a mismatch or anomaly, then Registry 620 notifies Key Master Administrator 511 of denied request for new user creation and any other requested information regarding denied new user credentials and associated existing Key Master 112. Such notification may occur via a Key Master Admin API 510 as depicted in reference numeral 4, a text message, an e-mail or other forms of communications.

If Registry 620 detects no mismatches or anomalies, then Registry 620 notifies Key Master Admin 511 of request for new user creation. Such notification may occur via a Key Master Admin API 510 as depicted in reference numeral 4, a text message, an e-mail or other forms of communications.

Key Master Admin 511 notifies Registry 620 of approval or denial for New User 553 to be service by existing Key Master 112. Such approval or denial may occur via a Key Master Admin API 510 as depicted in reference numeral 4 or through direct communications from Key Master Admin 511 to Registry 620.

Registry 620 notifies existing Key Master 112 of approval or denial decision by Key Master Admin 511 as depicted in reference numeral 3.

If New User 554 approved and authenticated, then existing Key Master 112 generates unique key pair(s) for New User 554 and normal operations may proceed.

Key Master Admin API and User API as Distributed Tool to Improve Breach Detection The use of distributed Key Master Admin APIs 510 and User APIs such as 554 as illustrated in FIG. 21 creates a network of individuals participating in the detection of breaches, including end-point breaches. The Registry 620 operates anomaly detection and related notifications. Such behavioral anomaly detection is easier to model based on the data of specific individuals than when alerting against monolithic data stores containing the information of many people. Further individual users can set thresholds for their own notifications. This combination of notifications directly to individual users and to Key Master Admins 510 thus improves detection of breaches compared to the alert fatigue that often dampens response from central information technology staff.

Key Master Admin API and the Key Vault

To prevent loss of access to encrypted data due to loss of private keys, a Key Vault 520 may be created by the Key Master Admin API 510 to which all private keys may be automatically and securely stored as illustrated in FIG. 22.

The combination of low cost Key Masters 112 and the Key Vault 520 enables distribution of encryption functions down to individual or small groups of users such as workgroups, small offices, families, etc.

The addition of the Key Master Admin API 510 enables secure activation of New Key Masters 714.

The Key Master Admin API 510 may integrate the Key Vault 520 within itself or alternatively may elect any external storage location.

In this variation of the process the Key Master Admin API 510 does not have encryption/decryption capabilities, thus making the Key Master Admin API 510 and associated Key Vault 520 very lightweight able, for instance, to be operated on a mobile smart phone.

Upon start-up of a New Key Master 714, the New Key Master 714 will generate its own device key pair and identify itself to the Registry 620 including providing the Registry 620 with the New Key Master's 714 public key, and in return the Registry 620 will provide its own public key to the New Key Master 714 as depicted in reference numeral 1.

The Key Master Admin 511 using the Key Master Admin API 510 will authenticate to the Registry 620 as depicted in reference numeral 3. Such authentication may use multi-factor authentication including biometric measures.

Key Master Admin 511 using Key Master Admin API 510 provides New Key Master 714 device ID to Registry 620. Registry 620 acknowledges the pairing of the Key Master Admin API 510 to the New Key Master 714 as depicted in reference numeral 3.

The New Key Master 714 will send to Key Vault 520 through the Key Master Admin API 510 a portion of its private key, for instance two-of-three components, encrypted with the Registry's 120 public key, plus the remaining portion of its own private key, for instance the third of three components, which may remain unencrypted in the Key Vault 520, the transmission bypassing the Registry 620 as depicted in reference numeral 2.

Each time the New Key Master 714 generates a new key pair for a user, the New Key Master 714 may send to the Registry 620 the new public key for the user as depicted in reference numeral 1.

Each time the New Key Master 714 generates a new key pair for a user, the Key Master 112 transmits to the Key Vault 520 through the Key Master Admin API 510 the new private key of the user encrypted with the New Key Master's 714 own public key as depicted in reference numeral 2.

Alternatively, each time the New Key Master 714 generates a new key pair for a user, the Key Master 112 transmits to the Registry 620 or to some other storage location, the new private key of the user encrypted with the New Key Master's 714 own public key as depicted in reference numeral 1.

The Key Master Admin API 510 and Key Vault 520 may employ a variety of security measures to prevent unauthorized access to the data stored in the Key Vault 520, but even if breached no unencrypted data is at risk other than the third component of the New Key Master's 714 private key.

Restoration of Keys from a Key Vault after Failure of Serving Key Master

As described herein, in the event that a Key Master 112 fails or is destroyed, the users' private keys may be successfully restored through a process managed by the Registry 620 in which other Key Masters 112 with which a user's private key has been previously shared restore the private keys to the replacement Key Master 112.

The implementation of one or more Key Vaults 520 offer an additional layer of protection and to protect private keys, including those that have never been shared with another Key Master 112 as illustrated in FIG. 22.

Upon start-up of a New Key Master 714 to replace an Old Key Master 712, the New Key Master 714 will generate its own device key pair and identify itself to the Registry 620 including providing the Registry 620 with the New Key Master's 714 public key, and in return the Registry 620 will provide its own public key to the New Key Master 714 as depicted in reference numeral 1.

The Key Master Admin 511 using the Key Master Admin API 510 will authenticate to the Registry 620 as depicted in reference numeral 3. Such authentication may use multi-factor authentication including biometric measures.

Key Master Admin 511 using Key Master Admin API 510 provides New Key Master 714 device ID to Registry 620. Registry 620 acknowledges the pairing of the Key Master Admin API 510 to the New Key Master 714 as depicted in reference numeral 3.

Key Master Admin API 510 using Key Vault 520 transmits the two-of-three components of the Old Key Master's 712 private key previously encrypted with the Registry's 620 public key to the Registry 620 as depicted in reference numeral 3.

The Registry 620 decrypts the two-of-three components of the Old Key Master's 712 private key using the Registry's 620 private key, encrypts with the New Key Master's 714 public key, and transmits to the New Key Master 714 as depicted in reference numeral 1.

The New Key Master 714 decrypts the two-of-three components of the Old Key Master's 712 private key using the private key of the New Key Master 714.

The Key Master Admin APT 510 transmits from the Key Vault 520 to the New Key Master 714 the third component of old Key Master's 112 private key as depicted in reference numeral 2.

The New Key Master 714 now has the Old Key Master's 712 private key.

Registry 620 transmits a list of users served by Old Key Master 712 to the New Key Master 714 encrypted with the New Key Master's 714 public key, the list of users served may include the users' public keys as depicted in reference numeral 1.

The Key Master Admin API 510 transmits from the Key Vault 520 the private keys of the users served encrypted with the Old Key Master's 712 public key to the New Key Master 714 as depicted in reference numeral 2, a process that may require a served-user verification process that may involve the Registry 620 and/or transmission of a served-user list from the New Key Master 714 to the Key Master Admin API 510.

The New Key Master 714 can now decrypt the served-users' private keys encrypted with the Old Key Master's 712 public key, restoring the private keys for normal operations by the New Key Master 714.

The Registry 620 updates any other Key Masters 112 with association to Old Key Master 712 of the New Key Master 714 identification which may include the New Key Master's 714 public key as depicted in reference numeral 4.

The Registry 620 updates any Cloud Lockboxes 130 with association to Old Key Master 712 of the New Key Master 714 identification which may include the New Key Master's 714 public key as depicted in reference numeral 5.

As one of ordinary skill in the art will recognize, if the Registry 620 or other secure storage has been designated to serve as the Key Vault 520, then a similar process would ensue.

Hosted Key Masters

Hosted Key Masters 512 may serve users electing not to own their own Key Master 112 as depicted in FIG. 23. Hosted Key Masters 512 may be configured to support individuals, workgroups and even entire enterprises. Hosted Key Masters 512 may also be employed for large scale workloads such as massive encryption projects, decryption projects and re-keying efforts. The following description envisions support for individual users.

Hosted Key Masters 512 would engage in the same start-up process as local Key Masters 112 as described herein, including the backup of the Hosted Key Masters' 512 private key in the Key Master Admin API's 510 Key Vault 520.

User A 551 would be coupled to the Hosted Key Master 512 using the User Primary API 530 in the same manner as when adding a user to an existing Key Master 112 as described herein.

Once coupled, Hosted Key Master 512 will generate public-private key pairs for User A 551.

Operations may proceed as with an on-premise Key Master 112, with the Hosted Key Master retaining User A's 551 private keys.

Given the absence of physical control by User A 551 of the Hosted Key Master 512, User A 551 may elect to exercise increased control of his/her private keys, providing the required private key from Key Vault 520 to Hosted Key Master 512 only when needed.

In order to maintain a second copy of his/her private keys by operating two Key Vaults 520, User A may also operate a User Secondary API 531 with an additional Key Vault 520 coupled to the Hosted Key Master 512. Such User Secondary API 531 may operate on a mobile device and may be involved in the registration processes for multi-factor authentication.

Hosted Key Master 512 will transmit to both User Primary API 530 and User Secondary API 531 the private keys of User A 551 each separately encrypted with the public key of the Hosted Key Master 512 as depicted in reference numerals 1 and 2, and such transmission may include a secure relay.

User Primary API 530 and User Secondary API 531 would add User A's 551 encrypted private keys to their respective Key Vaults 520 and send acknowledgement to the Hosted Key Master 512 of the successful vault storage of the encrypted private keys as depicted in reference numerals 1 and 2.

The Hosted Key Master 512 may then delete the private keys of User A 551 either automatically or based on a key revocation request from User Primary API 530 or User Secondary API 531.

User Primary API 530 or User Secondary API 531 may encrypt data using User A's 551 public key and proceed to deposit the encrypted file in one of the same manners as deposit operations conducted by Key Master 112 as described herein.

When retrieving a file from the Cloud Lockbox 130, the Hosted Key Master 512 may not have User A's 551 private key required for decryption of the data. Thus upon origination of the request to retrieve an encrypted file, the requesting application programming interface, either User Primary API 530 or User Secondary API 531, will provide to the Hosted Key Master 512 User A's 551 necessary encrypted private key from its Key Vault 520, as depicted in reference numerals 1 and 2, a transmission that may employ a secure relay.

Hosted Key Master 512 using its own private key will decrypt User A's 551 necessary encrypted private key, employ User A's 551 decrypted private key to decrypt the requested data file, and then transmit the decrypted data file to the requesting user application programming interface, either User Primary API 530 or User Secondary API 531, as depicted in reference numerals 1 and 2, a transmission that may employ a secure relay and/or may be encrypted with a synchronous session key.

The Hosted Key Master 512 may then delete both the encrypted and decrypted the private keys of User A 551 either automatically or based on a key revocation request from User Primary API 530 or User Secondary API 531, as depicted in reference numerals 1 and 2, a transmission that may employ a secure relay.

Addition of Compression

The Key Masters 112 and Hosted Key Masters 512 and/or User APIs such as 551 may also apply compression to data files.

Addition of Malware Detection to Key Master

Malware detection software could be added to the Key Masters 112 and Hosted Key Masters 512 as an extra precaution prior to transferring decrypted files to any API.

The mechanism could easily integrate with a wide variety of commercial malware detection tools.

Use of Symmetric Encryption for Communications

In addition to using asymmetric encryption for communications, the mechanism could use symmetric encryption to secure specific communications events.

Connections Outside of Community of Interest

A community of interest establishing a SEED Protocol instance could elect to allow depositing of files without a Key Master 112 by utilizing an Encryption-Only API 701 as illustrated in FIG. 24.

In such a scenario, the Encryption-Only User 702 using the Encryption-Only API 701 would establish their identity with the Registry 620.

The Registry 620 could directly, or after authorization, allow Encryption-Only User 702 using Encryption-Only API 701 to deposit encrypted files for a member of the community of interest such as User A 551 by providing the specified member's public key to the Encryption-Only API 701.

Such deposited files may be held in a Quarantine Location 703 for review by a members such as User A 551 before being added to the member's Cloud Lockbox 130.

Such Encryption-Only API's 701 may operate in any computing environment such as on a desktop, within a server and on a mobile device.

Tokenization for Transactional Data and Databases

Given that the HIE Registries 120 and Registries 620 establishes the unique identity of individuals, the individual identification number generated by the mechanism can be used as part of a tokenization process for transactional data and databases as depicted in FIG. 9. For instance, demographic information about an individual may be removed from a database and stored as an encrypted XML file in a Cloud Lockbox 130, replaced in the database with a token generated by a De-Identification and Tokenization API 119.

Subsequent retrieval of the demographic information would be controlled and monitored by the mechanism.

Similar efforts could tokenize financial information, credit card numbers and any other sensitive data.

Integration of Registry with External Identity Management Systems

A community of interest establishing an instance of the mechanism could elect to integrate external identity management systems with the HIE Registries 120 and Registries 620.

The HIE Registries 120 and Registries 620 would function as the top of an identity management tree structure with delegations to external identity management systems.

This process is similar to other federation processes in that the community of interest would determine requirements of inclusion of an identity management system based on criteria such as identity management thresholds.

Community of interest members may also indicate levels of trust for specific users and for specific branches of the federated identity management tree.

Varied levels of trust may be established within a federated identity management tree so that users can establish in their respective APIs the level of trust minimums for their own acceptance of another party's identity veracity, thus making automated sharing decisions based on such level of trust settings.

Adaptation for Use in the Internet of Things and Industrial Control Systems

A great need has emerged for owners of intelligent embedded systems to provide real-time protection, control and assurance of data integrity of devices, vehicles, buildings and other items equipped with systems of electronics, software, sensors and network connectivity, a range of systems sometimes called the Internet of Things. The mechanism describe herein can be modified to control who from the outside talks to such intelligent embedded systems and what commands the intelligent embedded system will accept from the outside parties. From intelligent cars to home monitoring/security systems to control systems to industrial HVAC, the push forward of capabilities has not been matched by a corresponding implementation of security and control. We will use an intelligent automobile as an example as illustrated in depicted in FIG. 25.

As with other examples contained herein, the automobile Manufacturer and $3^{rd}$ Party Providers establish their identities using the Manufacturer API 861 and the $3^{rd}$ Party Provider API 872 respectively in communications with the Registry 620.

As with other examples contained herein, the Manufacturer and $3^{rd}$ Party Providers activate and couple their respective Key Masters 112 to the Manufacturer API 861 and the $3^{rd}$ Party Provider API 871 in communications with the Registry 620.

Each automobile is equipped with an Onboard Key Master 812. As with other examples contained herein, the automobile Owner 851 using the Owner's Mobile Admin API 850 establishes his/her own identity with the Registry 620 and couples to the Onboard Key Master 812.

The Onboard Key Master 812 may include a GPS chipset and/or accelerometer to determine position and motion of the car providing the ability to include additional conditions in allowing or denying commands originating from outside the automobile. For instance, the automobile may deny a request to update software when the car is in motion.

The Onboard Key Master 812 will include a two-way communications link to the outside world, for instance, via a 4G cellular data service.

The Onboard Key Master 812 may also include one or more localized communications links for communications with the driver, the owner, other cars, smart infrastructure etc. For instance the Onboard Key Master 812 may communicate via Bluetooth and/or Wifi.

The Onboard Key Master 812 may communicate within the car to any number of subsystems such as Manufacturer Subsystems 860 and $3^{rd}$ Party Subsystems 870. All such communications will pass through the respective API such as Onboard Manufacturer API 862 and Onboard $3^{rd}$ Party API 872. Ideally such communications would occur via a in-car wired network such as Ethernet to reduce the chance of external hacking.

The Onboard Key Master 812 will also communicate with an Onboard Cloud Lockbox 830 that is mirrored to a remote Cloud Lockbox 130 when able.

The highest level of owner control would include a training process in which every command or information request originating from outside the automobile would be reviewed by the Owner 851 using the Owner's Mobile Admin API 850.

During such a training process, the Manufacturer API 861, for instance, would originate a pending command to the automobile as depicted in reference numeral 1.

This pending command would be encrypted by the manufacturer's Key Master 112 with the public key of the Onboard Key Master 812 and digitally signed using the private key of the manufacturer.

The encrypted and signed pending command will be transmitted from the manufacturer Key Master 112 to the Onboard Key Master 812 as depicted in reference numeral 2, a process that may employ a secure relay.

The Onboard Key Master 812 will decrypt the pending command using its own private key and verify the digital signature with the manufacturer's public key.

The Onboard Key Master 812 will decrypt the Acceptable Commands 834 and Acceptable Sources 832 files from the Onboard Cloud Lockbox 830 using its own private key.

The Onboard Key Master 812 will then compare the pending command and the current state of the automobile to the Acceptable Commands 834 file which includes acceptable states of the automobile for execution of specific commands, and compare the source of the command to the Acceptable Sources 832 file.

If the command is allowed and from an acceptable source, then the Onboard Key Master 812 will communicate the command to the Onboard Manufacturer API 862 as depicted in reference numeral 5.

The Onboard Manufacturer API 862 will then pass the command to the Manufacturer Subsystem 860 for execution as depicted in reference numeral 6.

Acknowledgement of command execution and any pertinent data that needs to be returned to the manufacturer may follow the reverse path of Manufacturer Subsystem 860 communicating to Onboard Manufacturer API 862 as depicted in reference numeral 6; Onboard Manufacturer API 862 communicating to Onboard Key Master 812 as depicted in reference numeral 5; Onboard Key Master 812 encrypting the data with the public key of the manufacturer's Key Master 112 and transmitting it to manufacturer's Key Master 112 as depicted in reference numeral 2; manufacturer's Key Master 112 decrypting the data with its private key and transmitting to Manufacturer API 861 as depicted in reference numeral 1.

The Onboard Key Master 812 will also write event log entries to the Registry 620, a transmission that may be buffered locally until able to establish contact with the Registry 620.

If the pending command is not in the Acceptable Commands 834 file and/or the source of the pending command is not in the Acceptable Sources 832 file, then the Onboard Key Master 812 will communicate the nature of the command and the source of the command to the Owner's Mobile Admin API 850 as depicted in reference numeral 3.

The Owner 851, using the Owner's Mobile Admin API 850 will allow or deny the command and the source, and communicate the decision to the Onboard Key Master 812 as depicted in reference numeral 3. If allowing a command, the owner may also elect to limit approval to specific automobile states of operation, e.g. in motion vs. not in motion.

If the approved command is allowed, then the Onboard Key Master 812 will add the pending command to the Acceptable Commands 834 file in Onboard Cloud Lockbox 830 for future command approval including details regarding allowed states of operation for the command as depicted in reference numeral 4.

If the approved command originated from a source not in the Acceptable Sources 832 file, then the Onboard Key Master 812 will add the new source to the Acceptable Sources 832 file.

The Acceptable Sources 832 file may also include cross-references for Acceptable Commands 834 for the specific Acceptable Source 832.

The Onboard Key Master 812 may also employ integrity checks on the Acceptable Sources 832 file and the Acceptable Commands 834 file through tamper-detection approaches such as a SHA-1 hash.

Commands denied by the owner may result in a denial message back to the source.

To provide data backup, the Acceptable Commands 834 file and the Acceptable Sources 832 file may be transmitted from the Onboard Cloud Lockbox 830 to the Cloud Lockbox 130, a process that may involve a secure relay.

Anomaly alerts regarding command denials or other unusual activity may be written to command logs and/or trigger alerts to the Owner 851 through Owner's Mobile Admin API 850.

Rather than conducting command-by-command training, the system may allow the owner to allow or deny classes of commands. For instance, owner may allow the manufacturer to issue diagnostic query commands without review but never allow operational commands such as applying the brakes.

The training process for the mechanism may be conducted with the mechanism initially being transparent to the manufacturer and $3^{rd}$ party providers by simply logging received commands and the output generated by the automobile.

As contained herein, the same training process may be employed for any of a wide variety of both manufacturer and $3^{rd}$ party applications such as roadside assistance, navigation, insurance company monitoring, etc.

The process may also be modified to create a "honey pot" for detecting attempts at unauthorized access to the automobile, creating a false dialog with the intruder in order to gather additional information regarding the intruder's intent, identity, location, etc.

Those skilled in the art will see that the mechanism as described for an automobile may also protect any intelligent embedded system including "smart" homes and many other Internet of Things configurations as well as industrial control and monitoring systems from any number of manufacturers and $3^{rd}$ parties.

Internet of Things Protection without Manufacturer or $3^{rd}$ Party Cooperation The mechanism described herein could also be truncated in the event that manufacturer or $3^{rd}$ party provider elect not to participate as illustrated in FIG. 26. While the truncated mechanism lacks identity verification of the originator of the commands, the Owner 851 can continue to exert control over which commands are executed and in what state of the automobile.

The training process for the truncated mechanism may be conducted with the mechanism initially being transparent to the manufacturer and $3^{rd}$ party providers by simply logging received commands and the output generated by the automobile.

At a time of the Owner's 851 choosing, he/she may trigger the training process to allow or deny specific commands and to determine in which automobile states allowed commands could be executed. After the training is complete, then the Owner 851 may elect to have the onboard mechanism become active in filtering commands from outside the automobile, still without participation of the manufacturer or third parties.

As contained herein, the same training process may be employed for any of a wide variety of manufacturer and $3^{rd}$ party applications such as roadside assistance, navigation, insurance company monitoring, etc.

Those skilled in the art will see that the mechanism as described for an automobile may also protect any intelligent embedded system including "smart" homes and many other Internet of Things configurations as well as industrial control and monitoring systems from any number of manufacturers and 3$^{rd}$ parties.

Wide Applicability

With three examples of industries that can utilize the described systems, devices and methods, one can easily imagine other applications of this flexible system in any situation in which multiple members need to have access to confidential information regarding an individual, such as the insurance industry, social service agencies, commercial research and development, scientific research, and finance, for example.

From the information contained herein, those skilled in the art will recognize that the mechanism could be adapted to protect case-based operations such as law enforcement cases, legal cases or other case-based enterprise by deploying public-private key pairs specific to a case. Such case-based mechanism modifications could also blend with the public-private key pairs generated for an individual aspects of the mechanism described herein.

From the information contained herein, those skilled in the art will perceive improvements, changes and modifications to the systems, devices and methods disclosed herein. Such improvements, changes and modifications within the skill of the art are intended to be covered by the present application.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, devices methods, and so on have been illustrated by describing examples, and while the examples have been described in considerable detail, it is not the intention of the applicants to restrict, or in any way, limit the scope of the appended claims to such detail. It is, of course, not possible to describe every conceivable combination of components or methodologies for purposes of describing the devices, systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995)

What is claimed is:

1. A system having a plurality of participants for conducting secure exchange of encrypted data within a community of interest using a tightly-coupled, distributed three-element-core mechanism consisting of:
   one or more cloud lockboxes operating on one or more file systems, wherein a cloud lockbox is configured to receive, store and enable secure retrieval of encrypted data;
   one or more key masters, wherein a key master is configured to:
     generate a public-private key pair for the key master;
     generate one or more public-private key pairs for each participant, of the plurality of participants in the community of interest, served by the key master;
     receive data from one or more participants;
     encrypt the received data with respective participants public keys;
     transmit the encrypted data to one or more cloud lockboxes associated with the respective participants;
     maintain the participants' private keys required for decryption of the encrypted data; and
     retrieve and decrypt the encrypted data from the one or more cloud lockboxes; one or more registries, wherein a registry is configured to;
     establish unique identities for each participant and key master;
     maintain a directory of the participants, the one or more cloud lockboxes, the one or more key masters and, the one or more registries; and
     create and manage one or more granular access control lists for determining access to stored data in the one or more cloud lockboxes;
   wherein the registry is configured to update permissions for the plurality of participants to enable the plurality of participants to at least one of add and retrieve data from the one or more cloud lockboxes based on the one or more granular access control lists.

2. The system of claim 1, wherein the three-element-core mechanism is configured to be integrated with one or more applications via one or more application programming interfaces.

3. The system of claim 1, wherein the mechanism supports a case-based focus meshed with an individual-based orientation, wherein permissions and key pairs may be assigned to both individuals and cases.

4. The system of claim 1, wherein the mechanism enables full lifecycle encryption and cross-platform sharing of encrypted data within and between organizations, individuals, applications, and devices.

5. The system of claim 1, wherein the mechanism provides an interface by automating encryption, decryption, and key exchange processes.

6. The system of claim 1, wherein the mechanism provides a distributed encryption solution enabling scalability to any size organization.

7. The system of claim 1, wherein a customized community of interest is generated based on a selection of at least one of a plurality of options among built-in operating parameters, comprising:
   selecting a public key encryption algorithm;
   selecting a registry or a plurality of registries;
   establishing membership requirements and identity verification thresholds;

selecting a storage solution or solutions at which to establish the one or more cloud lockboxes;

selecting from among a plurality of optional security measures;

determining a minimum application integration level; and determining initial metadata structure, purpose, and meaning.

8. The system of claim 1, wherein the three-part-core mechanism is vendor-neutral, thereby enabling underlying software to security-enable at least one of a records management, file sharing, or document management application software.

9. The system of claim 2, wherein the three-part-core mechanism and the application programming interface operate as a standalone service.

10. The system of claim 1, wherein the plurality of participants are associated with members of the community of interest, the member of the community of interest comprises at least one of:

an individual participating directly;

an organization participating for its own purposes; and an organization participating to represent multiple individuals, whereby the multiple individuals are participating by proxy.

11. The system of claim 10, wherein the three-part-core mechanism provides the multiple individuals participating by proxy or individuals participating directly the ability to access data, to review activity logs, and to receive alerts regarding anomalous access.

12. The system of claim 1, wherein the mechanism is configured to:

enable a key master to exchange one or more private keys of a participant with another key master;

encrypt a first participant's private key with the public key of the key master serving a second participant;

decrypt the first participant's private key with the private of the key master serving the second participant.

13. The system of claim 1, wherein the mechanism is configured to:

enable a key master to exchange one or more private keys of a participant with another key master using a secure relay;

encrypt a first participant's private key with the public key of the key master serving a second participant;

decrypt the first participant's private key with the private of the key master serving the second participant.

14. The system of claim 12, wherein the key master is further configured to exchange public keys of a participant with another key master.

15. The system of claim 13, wherein the key master is further enabled to exchange public keys of a participant with another key master using the secure relay.

16. The system of claim 1, wherein the mechanism is configured to:

update permissions at the registry serving a first participant to enable a second participant to deposit encrypted data into, and/or retrieve specified subsets of the encrypted data from, the first participant's cloud lockbox.

17. The system of claim 16, wherein the second participant is designated as a deposit-only participant.

18. The system of claim 1, wherein the mechanism is configured to:

generate activity records of at least one of key creation, key sharing, file retrieval requests, and private key exchanges.

19. The system of claim 1, wherein:

the key master is configured to be managed by a key master administrative application programming interface; and the key master administrative application programming interface includes a key vault for securely storing private keys of the key master and the private keys of participants served by the key master being administered.

20. The system of claim 2, wherein the key master is configured to generate a unique file identifier when encrypting a file, the unique file identifier:

is anonymous with respect to information regarding the owner or contents of the file;

is anonymous with respect to information regarding the physical storage location of the file;

is utilized throughout the lifecycle of the file to identity the file; and is provided to the application programming interface for use in later file retrieval.

21. The system of claim 1, wherein the cloud lockbox is configured to create and provide a one-time, time-limited, download token for retrieval of the encrypted data.

22. The system of claim 2, wherein the cloud lockbox is configured to generate a unique file identifier when receiving a file, the unique file identifier:

is anonymous with respect to information regarding the owner or contents of the file;

is anonymous with respect to information regarding the physical storage location of the file;

is utilized throughout the lifecycle of the file to identity the file; and is provided to the application programming interface for use in later file retrieval.

23. The system of claim 1, wherein the mechanism is configured to enable push notifications, indicative of new file availability, to members.

24. The system of claim 2, wherein the registry is configured to serve as a secure relay to:

receive encrypted data from a key master;

update access permissions to retrieve the encrypted data based on access policy and/or metadata appended to the encrypted data by the application programming interface;

transfer the encrypted data to a cloud lockbox; and facilitate retrieval of the encrypted data by requesting a time limited download token from the cloud lockbox to retrieve the encrypted data.

25. The system of claim 1, wherein the registry is configured to receive one or more activity logs from the key masters, the application program interfaces, and the cloud lockboxes to:

analyze the one or more activity logs to detect and halt anomalous access; and provide alerts regarding anomalous access and with routine access to activity logs.

26. The system of claim 2, wherein the registry is configured to conduct routine polling of the one or more key masters, the one or more application programming interfaces, the one or more cloud lockboxes, and other registries to verify accessibility of activity reporting.

27. The system of claim 1, wherein the key master is operated by or on behalf of a participant of the plurality of participants of the community of interest, wherein the key master is configured to:

receive a participant's related metadata;

encrypt the related metadata with the participant's public key;

create non-sensitive transactional metadata and associate the non-sensitive transactional metadata with the participant's data and related metadata;
transmit the encrypted metadata, and transactional metadata to a cloud lockbox associated with the participant, a process which employs a secure relay; and
retrieve the encrypted metadata from the cloud lockbox, a process which employs a secure relay.

28. The system of claim 1, wherein a registry remotely coupled to the cloud lockbox and the key master is configured to:
communicate with additional registries if more than one registry is operational for the community of interest; and
record the IP address of the key master, the cloud lockbox and the registry for selectively restricting communications.

29. The system of claim 1, wherein the registry is configured to conduct routing polling of the plurality of key masters to establish and maintain routine contact to:
provide awareness by the registry of key master status;
provide notification to key masters of pending secure relay actions;
download tokens to key masters to authorize retrieval of encrypted data; and
provide opportunity for security triggers related to changes of key master operational environment.

30. The system of claim 1, wherein the key master is configured to issue, honor and confirm requests from other key masters to revoke and erase their local copy of the private key of an individual participant that had been previously shared.

31. The system of claim 1, wherein the cloud lockbox is configured to employ a file system including at least one of public cloud services, private cloud environments, local or remote servers, and local device storage.

32. The system of claim 1, wherein an individual's cloud lockbox is split with an individual's files stored across a plurality of the file systems.

33. The system of claim 2, wherein an application programming interface is configured to at least one of:
convert data between a plurality of formats;
convert data between a key-value data store and a relational database;
generate metadata specific to an application, wherein the metadata is one of:
appended to data and encrypted with the data;
encrypted separately from the data; and
left unencrypted and added to the transactional metadata created by the key master by:
using unencrypted metadata as indexing elements, information about the source of the data; and
using unencrypted metadata to enable granular access control;
map a participant device's identification numbers in an application to community of interest identification numbers for the same participant device;
enable the creation of a hybrid cloud and an on-premise storage solution; and
transmit activity records of file retrieval requests and access revocations to the registries.

34. The system of claim 2, wherein an application programming interface is configured to:
facilitate multi-factor authentication in a key master or registry;
conduct administration of the key master;
host a vault for securely storing and backing up private keys of individuals and key masters;
receive alerts from the key masters, registries, cloud lockboxes or other application programming interfaces; and
respond to alerts from the key masters, registries, cloud lockboxes or other application programming interfaces transmitted to the application programming interface, texted to a device or transmitted as a voice call to the device.

35. The system of claim 1, where in a key master administration application programming interface enables a key master administrator to:
conduct routine maintenance of key master functions;
allow new users to associate to key master;
facilitate multi-factor authentication to a key master or registry;
receive alerts from the key masters, registries, cloud lockboxes or other application programming interfaces; and
respond to alerts from the key masters, registries, cloud lockboxes or other application programming interfaces transmitted to the key master administrative application programming interface, texted to a device or transmitted as a voice call to the device.

36. The system of claim 1, wherein a key master operates within an elastic compute environment to provide scalable hosted key master services.

37. The system of claim 2, wherein an application programming interface hosts a key vault to securely backup the private keys of participant.

38. The system of claim 1, wherein a user fully control access to his/her own private keys using an application programming interface and associated key vault.

39. The system of claim 2, wherein an application programming interface appends metadata to an encrypted file to indicate permissions inherited based on selections by the users.

40. The system of claim 2, wherein the application programming interfaces distribute and thus improve breach detection, including the breach of end-points.

41. The system of claim 2, wherein the key masters operate malware detection functions to:
scan files after decryption, before being provided to an application programming interface; and
scan files after being provided from the application programming interface, before encryption.

42. The system of claim 2, wherein individuals or companies outside a community of interest may operate the application programming interfaces to:
establish their identity at the registry;
obtain public key of an individual or organization;
encrypt data with the public key of an individual or organization;
transmit the encrypted data files to one of:
the recipient's cloud lockbox, a process that may include a secure relay; and
a quarantine location, a process that includes a secure relay; and
receive acknowledgement that a member of the community of interest received the encrypted data file.

43. The system of claim 1, wherein a member of a community of interest may receive data from individuals or companies outside the community of interest in which:
a notification is provided to the member that a file from an outside source is awaiting review in the quarantine location;

the member may review metadata and other information regarding sender of data;

the member may elect to accept data into their cloud lockbox; and the member's key master may decrypt and may scan the external file for malware.

44. The system of claim 1, wherein a registry may be integrated with an external identity management system to delegate an identity verification and/or access permissions processes to the external identity management systems.

45. The system of claim 1, wherein the three-part-core mechanism is configured to use unencrypted transaction metadata as indexing elements to provide information representative of transactional information as defined by the community of interest, including information about data source and date of storage.

46. The system of claim 1, wherein the three-part-core mechanism is configured to enable:
changing keys;
revoking access;
recovering keys;
recovering files;
de-identifying files;
tokenizing sensitive data; and
providing emergency access.

47. The system of claim 1, wherein the three-part-core mechanism is configured to offer a plurality of security levels by:
deploying the one or more key masters as one or more appliances;
integrating one or more applications with the mechanism to provide additional information, including an internal application username of a person requesting data;
requiring multi-factor authentication;
using messaging to/from mobile devices;
using a key master operational status; and
applying IP address communications restrictions based on information gathered by the registry.

48. The system of claim 1, wherein the key master is configured to compresses and decompresses data and to encrypt and decrypt data.

49. The system of claim 1, wherein the mechanism is configured to provide real-time protection, data integrity and control of intelligent embedded systems of electronics, software, sensors and network connectivity.

50. The system of claim 49, wherein the mechanism is configured to provide real-time protection for the intelligent embedded system by verifying the identity of entity issuing a remote command by:
verifying the identity of the entity using a digital signature, verification of which involves the registry, one of allowing or denying the remotely issued command based on a list of approved entities.

51. The system of claim 49, wherein a remote entity issuing commands to intelligent embedded systems may operate its own key master and related application programming interfaces to advance identity verification by an onboard key master.

52. The system of claim 49, wherein the mechanism is configured to provides real-time protection for the intelligent embedded system by:
one of allowing or denying remotely issued commands based on a list of accepted commands; and
one of allowing or denying remotely issued commands based on the operating state of the intelligent embedded system.

53. The system of claim 49, wherein the owner of the intelligent embedded system trains the mechanism regarding the identity of entities approved for issuing remote commands, the specific commands allowed, and the related state of the intelligent embedded system during which approved commands are allowed.

54. The system of claim 49, wherein the mechanism is configured to operate transparently for some period of time, cataloging all commands issued by remote entities and providing to the owner of intelligent embedded system opportunity to one of accept or deny commands and establish an intelligent embedded system state in which commands may be executed.

55. The system of claim 49, wherein onboard data is synchronized to a location remote from the embedded system to provide backup of the approved identities, commands, and related embedded system states.

56. The system of claim 49, wherein the mechanism is configured to determine the integrity of the approved list of identities to issue remote commands and the integrity of the list of approved remote commands using an file integrity checking solution.

57. The system of claim 49, wherein remotely issued commands and related actions by the mechanism are logged and transmitted to a location remote from the embedded system.

58. The system of claim 1, wherein the registry is further configured to maintain a directory for lookup and delivery of public keys of participants, organizations, and devices.

59. The system of claim 1, wherein the mechanism is configured to support secure sharing without the exchange of participant's private keys through use of deposit-only permissions supporting participant-to-participant exchange.

* * * * *